(12) United States Patent
Ruppersberg et al.

(10) Patent No.: US 10,004,386 B2
(45) Date of Patent: Jun. 26, 2018

(54) OTOSCOPE

(71) Applicant: Helen of Troy Limited, Belleville (BB)

(72) Inventors: Peter Ruppersberg, Blonay (CH);
Albrecht Lepple-Wienhues, Pontarlier (FR)

(73) Assignee: Helen of Troy Limited, Belleville (BB)

( * ) Notice: Subject to any disclaimer, the term of this patent is extended or adjusted under 35 U.S.C. 154(b) by 186 days.

(21) Appl. No.: 14/762,427

(22) PCT Filed: Feb. 4, 2014

(86) PCT No.: PCT/EP2014/000296
§ 371 (c)(1),
(2) Date: Jul. 21, 2015

(87) PCT Pub. No.: WO2014/117957
PCT Pub. Date: Aug. 7, 2014

(65) Prior Publication Data
US 2015/0351620 A1    Dec. 10, 2015

Related U.S. Application Data

(60) Provisional application No. 61/809,048, filed on Apr. 5, 2013, provisional application No. 61/760,511, filed
(Continued)

(30) Foreign Application Priority Data

Feb. 4, 2013   (EP) ..................... 13000552
Feb. 4, 2013   (EP) ..................... 13000553
Apr. 5, 2013   (EP) ..................... 13001748

(51) Int. Cl.
*A61B 1/267*   (2006.01)
*A61B 1/00*    (2006.01)
(Continued)

(52) U.S. Cl.
CPC ...... *A61B 1/00142* (2013.01); *A61B 1/00009* (2013.01); *A61B 1/00057* (2013.01);
(Continued)

(58) Field of Classification Search
CPC ......... A61B 1/227; A61B 1/06; A61B 1/0623; A61B 1/0615
(Continued)

(56) References Cited

U.S. PATENT DOCUMENTS 4,366,811 A    1/1983   Riester
4,380,998 A    4/1983   Kieffer, III et al.
(Continued)

FOREIGN PATENT DOCUMENTS

CN       1829468 A     9/2006
CN     102026574 A     4/2011
(Continued)

OTHER PUBLICATIONS

Salvinelli, F., et al., "The External Ear and the Tympanic Membrane—A Three-Dimensional Study," *Scandinavian Audiology* 20(4):253-256, 1991.
(Continued)

*Primary Examiner* — Ellen C Hammond
*Assistant Examiner* — Christina Negrellirodrigue
(74) *Attorney, Agent, or Firm* — Seed Intellectual Property Law Group LLP

(57) ABSTRACT

An otoscope comprising a handle portion and a head portion substantially tapering along its longitudinal axis, wherein the head portion has a proximal end adjacent to the handle portion and a smaller distal end configured to be introduced in an outer ear canal. The otoscope comprises an optical electronic imaging unit at the distal end of the head portion, especially at a distal tip of the head portion, wherein the electronic imaging unit exhibits at least one optical axis
(Continued)

which is radially offset from the longitudinal axis, and wherein the distal end is configured for accommodating the electronic imaging unit in such a way that the radial offset can be maximum with respect to the diameter of the distal end.

44 Claims, 23 Drawing Sheets

Related U.S. Application Data on Feb. 4, 2013, provisional application No. 61/760,507, filed on Feb. 4, 2013.

(51) Int. Cl.
| | |
|---|---|
| *A61B 1/07* | (2006.01) |
| *A61B 1/06* | (2006.01) |
| *A61B 5/01* | (2006.01) |
| *A61B 5/00* | (2006.01) |
| *A61B 1/227* | (2006.01) |
| *A61B 5/11* | (2006.01) |
| *A61B 1/05* | (2006.01) |
| *A61B 5/107* | (2006.01) |

(52) U.S. Cl.
CPC ...... *A61B 1/00066* (2013.01); *A61B 1/00101* (2013.01); *A61B 1/00179* (2013.01); *A61B 1/05* (2013.01); *A61B 1/051* (2013.01); *A61B 1/0623* (2013.01); *A61B 1/0638* (2013.01); *A61B 1/0676* (2013.01); *A61B 1/0684* (2013.01); *A61B 1/07* (2013.01); *A61B 1/227* (2013.01); *A61B 1/2275* (2013.01); *A61B 5/0075* (2013.01); *A61B 5/0086* (2013.01); *A61B 5/01* (2013.01); *A61B 5/1077* (2013.01); *A61B 5/11* (2013.01); *A61B 5/6817* (2013.01); *A61B 5/7203* (2013.01); *A61B 5/7221* (2013.01); *A61B 5/7246* (2013.01); *A61B 5/7264* (2013.01); *A61B 5/7275* (2013.01); *A61B 5/74* (2013.01); *A61B 2562/0242* (2013.01)

(58) Field of Classification Search
USPC .................................................. 600/199, 200
See application file for complete search history.

(56) References Cited

U.S. PATENT DOCUMENTS

| | | | |
|---|---|---|---|
| 4,685,452 | A | 8/1987 | Riester |
| 4,766,886 | A | 8/1988 | Juhn |
| 5,363,839 | A | 11/1994 | Lankford |
| 5,868,682 | A | 2/1999 | Combs et al. |
| 5,919,130 | A | 7/1999 | Monroe et al. |
| 5,935,058 | A | 8/1999 | Makita et al. |
| 5,951,486 | A | 9/1999 | Jenkins et al. |
| 6,165,035 | A | 12/2000 | Avner |
| 6,898,457 | B1 | 5/2005 | Kraus et al. |
| 7,529,577 | B2 | 5/2009 | Jensen et al. |
| 2002/0087084 | A1 | 7/2002 | Shahar et al. |
| 2003/0108083 | A1 | 6/2003 | Seitz |
| 2003/0139672 | A1 | 7/2003 | Cane et al. |
| 2004/0136010 | A1 | 7/2004 | Jensen et al. |
| 2005/0027168 | A1 | 2/2005 | Strom et al. |
| 2005/0192482 | A1 | 9/2005 | Carpenter et al. |
| 2005/0228231 | A1 | 10/2005 | MacKinnon et al. |
| 2008/0249369 | A1 | 10/2008 | Seibel et al. |
| 2009/0030295 | A1 | 1/2009 | Shioi et al. |
| 2009/0182526 | A1 | 7/2009 | Quinn et al. |
| 2010/0060718 | A1 | 3/2010 | Forster et al. |
| 2011/0063428 | A1 | 3/2011 | Sonnenschein et al. |
| 2011/0112791 | A1* | 5/2011 | Pak ..................... A61B 1/227 |
| | | | 702/131 |
| 2011/0137118 | A1 | 6/2011 | Huang |
| 2011/0257481 | A1 | 10/2011 | Ogawa et al. |
| 2012/0059224 | A1* | 3/2012 | Wellen ................ A61B 1/2275 |
| | | | 600/200 |
| 2012/0130168 | A1 | 5/2012 | Konomura |
| 2012/0179187 | A1 | 7/2012 | Loushin et al. |
| 2012/0253166 | A1 | 10/2012 | Ahn et al. |
| 2012/0327426 | A1 | 12/2012 | Hart et al. |
| 2013/0027515 | A1 | 1/2013 | Vinther et al. |
| 2013/0083823 | A1 | 4/2013 | Harr et al. |
| 2013/0237754 | A1 | 9/2013 | Berglund et al. |
| 2013/0296685 | A1 | 11/2013 | Tsuboi et al. |
| 2015/0351606 | A1 | 12/2015 | Ruppersberg et al. |
| 2015/0351607 | A1 | 12/2015 | Ruppersberg et al. |
| 2015/0351616 | A1 | 12/2015 | Ruppersberg et al. |
| 2015/0351637 | A1 | 12/2015 | Ruppersberg et al. |
| 2015/0374208 | A1 | 12/2015 | Ruppersberg et al. |

FOREIGN PATENT DOCUMENTS

| | | |
|---|---|---|
| EP | 0 472 490 B1 | 2/1992 |
| EP | 1 134 565 A1 | 9/2001 |
| EP | 1 477 107 A1 | 11/2004 |
| EP | 2 014 220 A1 | 1/2009 |
| EP | 2 289 391 A1 | 3/2011 |
| EP | 2 277 439 A2 | 1/2012 |
| JP | 63-40117 A | 2/1988 |
| JP | 5-253184 A | 10/1993 |
| JP | 7-111987 A | 5/1995 |
| JP | 9-19403 A | 1/1997 |
| JP | 11-28194 A | 2/1999 |
| JP | 11-113841 A | 4/1999 |
| JP | 11-316157 A | 11/1999 |
| JP | 2000-30063 A | 1/2000 |
| JP | 2001-517105 A | 10/2001 |
| JP | 2002-135887 A | 5/2002 |
| JP | 2002-528158 A | 9/2002 |
| JP | 2004-535834 A | 12/2004 |
| JP | 2005-519666 A | 7/2005 |
| JP | 2007-130084 A | 5/2007 |
| JP | 2007-144103 A | 6/2007 |
| JP | 2007-236734 A | 9/2007 |
| JP | 2009-153664 A | 7/2009 |
| JP | 2009-178482 A | 8/2009 |
| JP | 2009-201853 A | 9/2009 |
| JP | 2011-62370 A | 3/2011 |
| JP | 2011-72638 A | 4/2011 |
| JP | 2011-104333 A | 6/2011 |
| JP | 2011-520501 A | 7/2011 |
| JP | 2012-514200 A | 6/2012 |
| JP | 3178405 U | 8/2012 |
| JP | 2013-202260 A | 10/2013 |
| JP | 2014-525774 A | 10/2014 |
| JP | 2015-530886 A | 10/2015 |
| KR | 10-2006-0122567 A | 11/2006 |
| TW | 201225896 A1 | 7/2012 |
| WO | 02/39874 A2 | 5/2002 |
| WO | 2007/049562 A1 | 5/2007 |
| WO | 2009/139548 A2 | 11/2009 |
| WO | 2009/157825 A1 | 12/2009 |
| WO | 2012/061697 A1 | 5/2012 |
| WO | 2013/002935 A1 | 1/2013 |
| WO | 2013/016651 A1 | 1/2013 |

OTHER PUBLICATIONS

Wäny, M., et al., "Utrasmall Digital Image Sensor for Endoscopic Applications," in *Proc. of 2009 International Image Sensor Workshop*, Bergen, Norway, Jun. 22-28, 2009, 4 pages.

Wilke, M., et al., "Prospects and Limits in Wafer-Level-Packaging of Image Sensors," Electronic Components and Technology Conference (ECTC), 2011 IEEE 61st, Lake Buena Vista, Florida, May 31-Jun. 3, 2011, pp. 1901-1907.

* cited by examiner

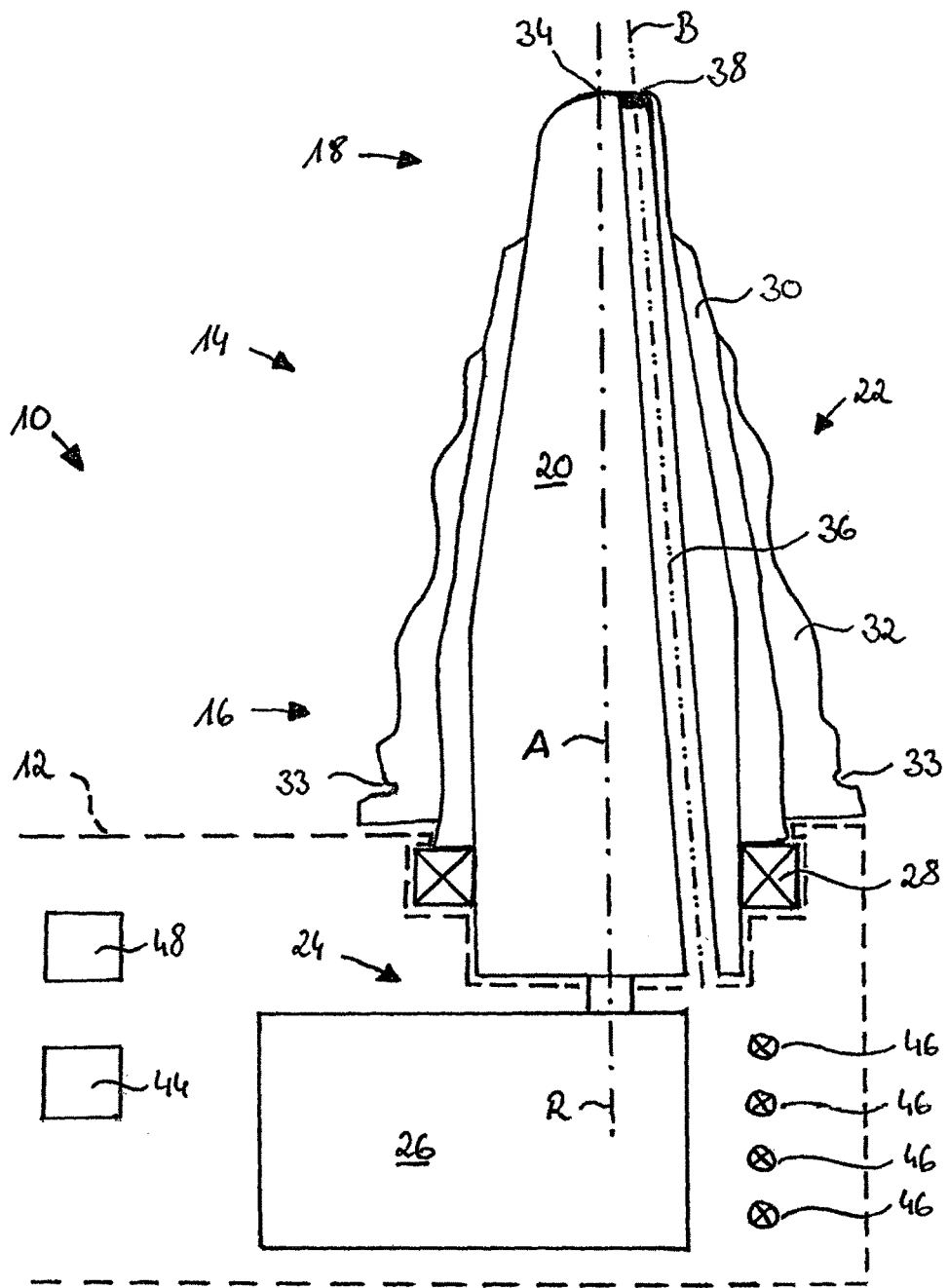
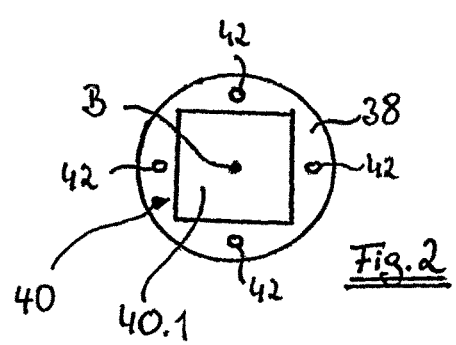
Fig. 1
Fig. 2

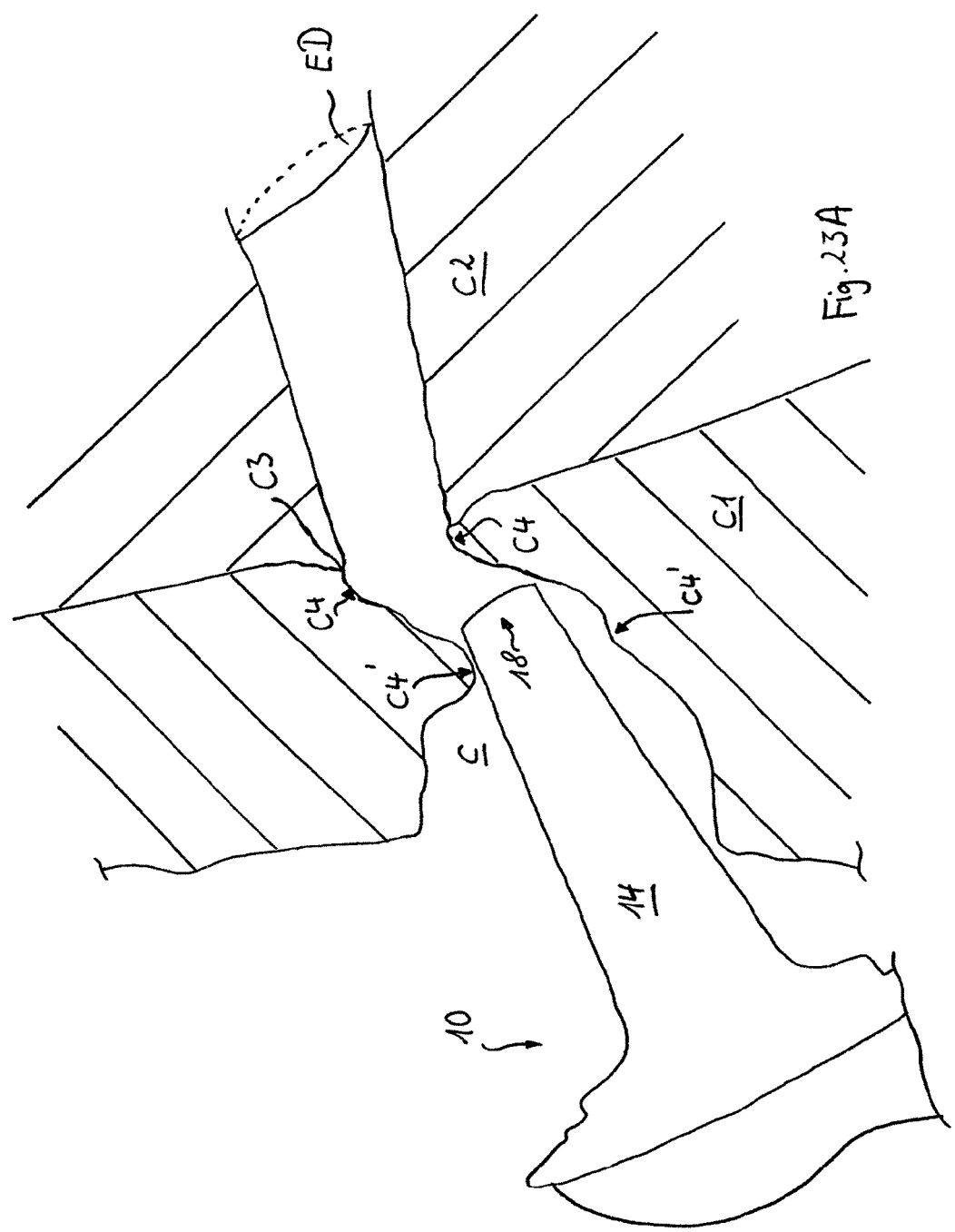

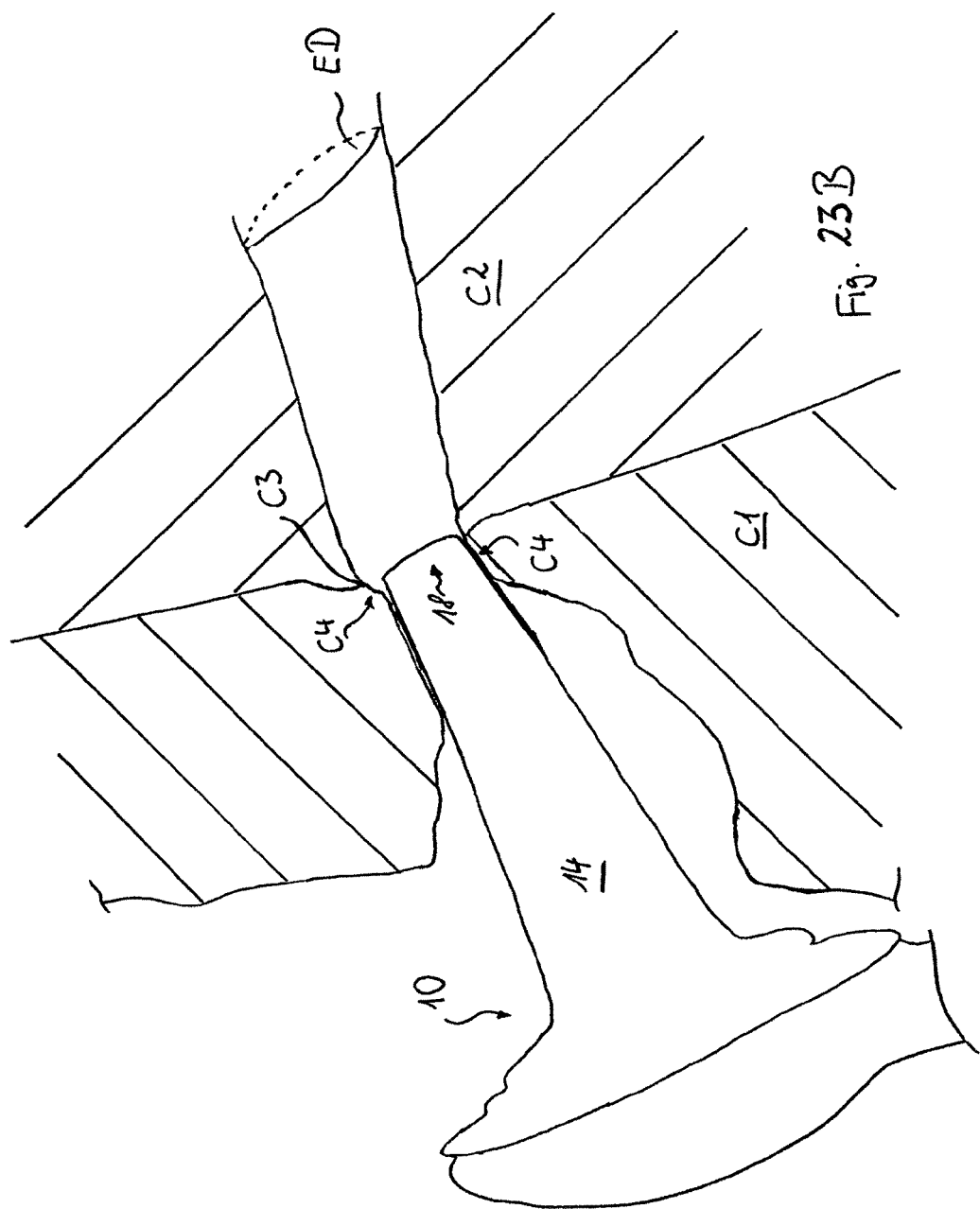

OTOSCOPE

FIELD OF THE INVENTION

The invention refers to an otoscope comprising a handle portion allowing a user to manipulate the otoscope during its application, and further comprising a head portion exhibiting a substantially tapering form extending along a longitudinal axis of the head portion, wherein the head portion has a proximal end adjacent to the handle portion and a smaller distal end configured to be introduced in an ear canal of a patient's outer ear.

An otoscope (sometimes also called "auriscope") is a medical device which is used to look into ears. The corresponding method of doing so is called "otoscopy". Otoscopy is a standard medical examination technique established more than 100 years ago. Medical students learn otoscopy early in their studies during the practical course in physiology. Typical diagnoses based on otoscopic examination are: otitis media (OM), otitis media with effusion (OME), otitis externa, and eardrum perforation. OME is defined by the presence of middle ear effusion, i.e. a liquid behind an intact tympanic membrane without signs or symptoms of acute infection. OME is one of the most frequent pediatric diagnoses. However, otoscopy is also used to generally identify and observe object's in the ear, such as earwax, hair and the eardrum.

A typical otoscope 10' as used for decades in otoscopy is shown in FIG. 3. The otoscope 10' comprises a handle portion 12' allowing the user to manipulate the otoscope during its application. The term "to manipulate" in this context refers to different kinds of manipulation, such as—but not limited to—holding the otoscope, aligning the otoscope with respect to the patient's ear, and turning on or off a light. The otoscope 10' further comprises a head portion 14' connected to the handle portion 12'. The head portion 14' exhibits a substantially tapering form—usually a conical form—extending along a longitudinal axis A' of the head portion 14'. The head portion 14' is substantially comprised of an empty funnel, wherein the tip of the funnel typically has a relatively small diameter, e.g. about 3 millimeters for children. Furthermore, the head portion 14' has a proximal end 16' adjacent to the handle portion 12' and a smaller distal end 18' configured to be introduced in an ear canal C of a patient's outer ear. The term "end" in this context does not mean a single point but rather refers to a region or section of the head portion 14', wherein the proximal end 16' is located opposite to the distal end 18' with respect to the longitudinal axis A'. The ear canal C is partly surrounded by soft connective tissue C1 and—further down towards the middle ear—partly by hard bone C2.

The working principle of the known otoscope is typically to observe and simultaneously illuminate the patient's eardrum ED through the empty funnel with the 3 mm tip pushed deeply into the ear canal C. Normally, the eardrum ED is not visible from outside the ear, due to the natural curvature of the ear canal C. In order to overcome the natural curvature of the ear canal C, the skilled physician has to carefully pull the outer ear upward and to the back while carefully pushing the tip of the funnel as deeply as necessary to observe the eardrum. The ear canal C has to be deformed (especially straightened) in such a way that the physician has a free view onto the eardrum ED along the optical axis of the otoscope 10', wherein the optical axis corresponds to the longitudinal axis A' of the head portion 14'. The optics of an otoscope is situated only at the wider end of the funnel at its proximal end 16' and essentially consists of a lamp and a lens (not shown) to magnify the image of the eardrum ED.

The otoscopy procedure needs manual skills and significant training to make it possible to carefully push the funnel into the ear canal C while looking inside and manipulating the curvature of the ear canal C by pulling the ear. For example, it is very important for the trained physician to brace the hand holding the otoscope against the patient's head to avoid injury to the ear canal C by placing the index finger or little finger against the head. In particular in young children—where the inner part of the ear canal is relatively short and sudden head movement during the examination may occur—there is a risk of penetration of the very sensitive ear canal skin or even of the eardrum ED. Besides pain and handicapped hearing, such an injury may even induce cardiovascular complications through a vagal overstimulation and therefore has to be avoided by all means.

Furthermore, especially in an inflamed ear, the mechanical manipulation of "straightening" the ear canal C typically causes considerable discomfort or even pain, rendering the examination of an infant even more difficult.

FIG. 4 illustrates that with a distal tip of the otoscope 10' being positioned far within the bony part C2, the ear canal C has to be "straightened" considerably in such a way that the longitudinal axis A is directed onto the eardrum ED, at least approximately. The distal tip of the head portion 14' is supported within the bony part C2, such that a proximal end of the head portion 14' contacting the soft connective tissue C1 can push the soft connective tissue C1 downwards. The head portion 14' is shaped such that there remains the danger of touching the eardrum ED.

BACKGROUND OF THE INVENTION

For the above reasons, reliably and securely handling an otoscope of the art is currently subject to only well trained physicians and not amenable to the larger community of practitioners. A study recently published in the US as a result of a survey has shown that even physicians often fail to (correctly) determine the status of e.g. the subject's eardrum or fail to correctly interpret the image provided by the otoscope (i.e. correct and meaningful object recognition). Such failures result in misinterpretation of the status of the inner ear canal or the eardrum. As a consequence, e.g. over-medication with antibiotics for treating supposed inflammations of the eardrum occurs, because physicians tend to err on the side of caution, or meaningless image interpretation occurs.

Notably, there also exist other otoscopic devices, as e.g. video otoscopes, allowing a skilled expert to capture images of the subject's eardrum and the ear canal. Such video otoscopes comprise a bundle of light guides extending from the distal end of the head portion to a CCD-chip located remote from the distal end. The achievable resolution of the images depends on the number of light guides. In order to obtain images having a satisfying resolution, a significant number of individual light guides must be provided rendering devices by far too expensive for routine care. Moreover, all of the known video otoscopes having the CCD-chip located remote from the distal end of the head portion require superior handling skills by the physician. For the above reasons, they are not configured and suitable for domestic use by a larger community of practitioners, nor use by laypersons.

All otoscopes currently on the market—including video otoscopes—generally are based on the following fundamental design: a relatively thin open funnel. Length, angle, field of vision and size of the funnels are essentially similar for all marketed otoscopes. As a result of these common characteristics, ease of use (due to safety issues) is limited for such devices. Methods for reliable detection of objects in the ear canal, including the eardrum, are remarkably intricate with such known otoscopes.

Consequently, until today otoscopy has almost been exclusively applied by medical doctors. And even among medical doctors, only a minor percentage is sufficiently trained to carry out otoscopy in a reliable and appropriate way. However, since otitis media is the most frequent disease causing high fever in young children, and to exclude otitis media, especially OME, is a major reason for seeing a pediatrician, there is an urgent need for a parental check of the ear. Parents may also benefit from an otoscope that can be securely used by laypersons at home in order to check whether an ear canal of their child is blocked by massive earwax and/or foreign objects.

Prior art document U.S. Pat. No. 5,910,130 A describes an otoscope with a miniature video camera or a solid-state imager, e.g. a CCD or CMOS. A light source can be provided in the form of a continuous ring of light emitting fibres. The head portion of the otoscope has to be introduced far into a straightened ear canal in order to observe the eardrum.

Prior art document US2013/027515 A1 describes an ear canal side scanner with a small diameter comprising a camera including e.g. a CCD or CMOS chip. The camera can be arranged at a tip of a probe of the side scanner. The scanner allows for side scans of lateral surfaces of the ear canal. The tip of the side scanner is positioned close to the eardrum before scanning.

Prior art document US 2011/063428 A1 describes a medical device (an endoscope) comprising illumination means and a video camera based on wafer level optics, e.g. a solid state imager, and having a maximum outer diameter of less than 3.2 mm.

Prior art document EP 2 289 391 A1 describes an otoscope with a head portion and a fastening ring for reversibly mounting the head portion to a display portion.

Prior art document EP 2 277 439 A2 describes a clinical ear thermometer including an image sensor which is positioned radially offset, especially in order to provide a cavity in which a temperature sensor can be arranged at a distal end.

It is therefore an object of the present invention to provide an otoscope that allows for domestic application by laypersons and medical doctors without extensive otoscopy training and without any—or at least with a significantly reduced—risk of causing injuries to the patient. In particular, it is an object of the present invention to provide an otoscope that allows for automatically identifying objects within the ear canal, e.g. the eardrum, substantially irrespective of the relative position of a head portion of the otoscope within the ear canal. The object of the present invention can also be describes as to provide an otoscope that allows for identifying objects with high reliability, even if the otoscope is applied by laypersons.

This object is achieved according to the present invention by an otoscope exhibiting the features of claim 1 or claim 19 or claim 20. Preferred embodiments represent the subject-matter of the dependent claims.

In particular, this object is achieved by an otoscope of the generic type as described above, wherein the otoscope further comprises an optical electronic imaging unit positioned at the distal end of the head portion, especially at a distal tip of the head portion, wherein the electronic imaging unit exhibits at least one optical axis which is positioned radially offset from the longitudinal axis, and wherein the distal end is configured for accommodating the electronic imaging unit in such a way that the radial offset can be maximum with respect to the diameter of the distal end. The larger the radial offset, the better the view onto the eardrum, even in case the distal end is positioned only in a transition area between soft connective tissue and hard bone confining the ear canal. The electronic imaging unit may be arranged such that the radial offset is maximum with respect to the diameter of the distal end, in order to allow the otoscope for effectively looking around a curvature of the ear canal.

Providing a small electronic imaging unit at the distal end of the head portion exhibiting at least one optical axis which is radially offset allows to "see" the patient's eardrum without the need to deform the patient's ear canal, or at least without having to deform the ear canal to such an extent as with the above described conventional otoscope. The reason for this is that there is no need for the "viewing direction" of the electronic imaging unit to correspond to the longitudinal axis of the head portion of the otoscope. Rather, the radial offset can ensure that there is a line of sight onto the eardrum even if the ear canal is not straightened, allowing the device to "look around the corner". In particular, in many cases, the ear canal of the outer ear is not straight-lined, but exhibits at least one curvature, especially at a transition area or transition point between soft connective tissue and hard bone confining the ear canal. The "corner" is provided by this curvature. In particular, virtually almost always, the ear canal has an S-shaped (sigmoid) form with a first curvature and a second curvature, the second curvature being closer to the eardrum than the first curvature. Particularly, the second curvature of the ear canal obstructs any optical line of sight or visual communication of an otoscope which is not introduced as far as at least some millimeters within the bony part of the ear canal. The "corner" can be defined as the second curvature of the ear canal. In particular, in a distal direction, the second curvature leads to the bony part of the ear canal. A transition point or area between soft connective tissue and hard bone is arranged at this second curvature. The second curvature leads into the section of the ear canal which is exclusively confined by hard bone. Preferably, the transition area can be defined as an area of about a few millimeters distal to (behind) and about a few millimeters proximal to (in front of) a curvature, especially 0 mm to 5 mm or 1 mm to 3 mm.

Such an electronic imaging unit can provide an otoscope which can be used by laypersons, without extensive otoscopy training and with a significantly reduced risk of causing injuries, especially with a significantly reduced risk of irritation of the patient's tissue, e.g. the tissue within the hard bone section of the ear canal. Such an electronic imaging unit allows for observing the eardrum substantially irrespective of the relative position of a head portion of the otoscope within the ear canal, especially irrespective of any specific insertion depth into the bony part of the ear canal, i.e. the section confined by hard bone. As the otoscope is arranged for "looking around the corner or curvature", the layperson does not have to introduce the head portion as far as a section of the ear canal which is confined by hard bone. While in traditional otoscopy, the physician has to introduce the otoscope at least as far as some millimeters within the bony part of the ear canal, i.e. considerably further inwards than the second curvature, an otoscope according to the present invention can be positioned adjacent to the second curvature. In traditional otoscopy, the otoscope is necessarily introduced far into the bony part of the ear canal, especially in order to provide a kind of support or rest or anchoring point at the distal tip of the otoscope. Once the distal tip of the otoscope is supported within the bony part, the physician can apply a leverage on the handle portion of the otoscope, in order to straighten the ear canal and in order to ensure an optical line of sight onto the eardrum. But, this kind of "alignment" of the otoscope or this kind of straightening out the ear canal is painful. In contrast, the otoscope according to the invention does not require such an "alignment" or straightening.

According to one specific embodiment, the electronic imaging unit may also exhibit a field of vision with a wide angle, such that the eardrum is visible even in case the longitudinal axis is inclined with a large angle with respect to an longitudinal axis of the ear canal. According to another embodiment, the optical axis of the electronic imaging unit may also be arranged at an angle with respect to the longitudinal axis, allowing the device to "look around the corner" more effectively. An additional or alternative reason is that the field of vision of an electronic imaging unit provided at the distal end of the head portion can be much greater than the field of vision achievable with the relatively acute empty funnel of the otoscope according to the prior art.

Furthermore, in contrast to conventional otoscopes, the distal end of the head portion of the otoscope according to the present invention does not need to have a conical shape with a relatively thin open funnel, which shape bears the risk of introducing the distal end of the head portion too far into the ear canal, so as to cause serious injuries to the patient. Instead, the outer shape of the distal end of the head portion can be designed in such a way that it is practically impossible to introduce it too far into the ear canal. Thus, the otoscope according to the present invention can be securely and reliably operated even by laypersons without the risk of causing injuries to the patient. In particular, the otoscope according to the present invention allows for observing the eardrum substantially irrespective of the relative position of a head portion of the otoscope within the ear canal, especially irrespective of any specific insertion depth into the bony part of the ear canal, i.e. the section confined by hard bone. The distal end can be provided with a shape which allows for mechanically preventing any contact with the eardrum. In particular, the distal end can be provided with a relatively large diameter, which allows for both a large radial offset and a mechanical stop within the ear canal at a position relatively far away from the eardrum.

The distal end may exhibit a cavity for at least partially accommodating the electronic imaging unit such that the radial offset can be maximum within the lateral walls or lateral surface of the distal end, preferably at least half the radius (half of half the radial dimension) of the distal tip, more preferable at least ⅔ of the radius (or ⅔ of half the radial dimension) of the distal tip.

According to one embodiment, the radial offset is at least factor 0.25 of the radial dimension of the distal end, preferably at least factor 0.3, more preferable at least factor 0.35. Such a relatively large radial offset can ensure positioning the optical axis in a favorable eccentric observation point within the ear canal, even in case the distal tip in introduced only as deep as a transition point between soft connective tissue and hard bone.

According to one specific embodiment, the at least one miniature camera and/or the infrared sensor unit are positioned at a distance of less than 3 mm, preferably less than 2 mm, more preferable less than 1 mm, from the distal tip. Such an arrangement, especially as close as possible to the distal tip, allows for providing the maximum eccentricity within the ear canal, allowing for effectively "looking around the corner".

According to one embodiment, adjacent to an inner lateral surface of the distal end, the head portion exhibits a cavity for accommodating an optical component (e.g. a camera, a lens or an image sensor) of the electronic imaging unit defining the at least one optical axis, such that the optical axis can be arranged as close as possible to the inner lateral surface of the distal end. Such a cavity ensures maximum radial offset. Preferably, the cavity at least partially is confined by the inner lateral surface of the distal end.

Preferably, the electronic imaging unit or at least an optical component thereof, e.g. a lens, is positioned at the most distal part of the head portion. In particular, the electronic imaging unit can be in contact with a front side or front face of the head portion, or the electronic imaging unit can provide a front side or front face of the head portion. This enables positioning the electronic imaging unit most distal within the ear canal without the need of introducing the head portion deep into the ear canal.

The otoscope according to the present invention may comprise further features that are provided, for example, by modern digital photo cameras. For example, the otoscope may comprise visual output means, such as a display, and/or acoustic output means, such as a loudspeaker, and/or a storage card slot for inserting a storage card to store the acquired images, and/or a cable connection port, such as an USB-port, and/or a wireless connection, such as Bluetooth®, WIFI®, and/or an energy supply, such as a battery.

Preferably, an "optical axis of the electronic imaging unit" is an axis which extends from a most distal point of the electronic imaging unit in a distal direction, especially towards the eardrum, wherein its orientation is not modified any more by any optical components. The "optical axis of the electronic imaging unit" of an electronic imaging unit preferably is the optical axis with the largest radial offset.

Preferably, the at least one optical axis is arranged as close as possible to an inner lateral surface of the distal end. Thereby, the radial offset can be maximized.

The electronic imaging unit may comprise a video camera defining an optical axis, preferable a wide angle color video camera. The term "wide angle" in this context refers to angels of at least 80°, preferably of at least 110°, e.g. 120°. Such wide angle cameras allow detection of the patient's eardrum, even if the optical axis of the camera is not directly centered to the eardrum and even if the eardrum is relatively remote from the camera, compared to the distance between the eardrum and the tip end of a conventional otoscope head during application. Using a color video camera is advantageous, allowing determination of the color of the eardrum and/or of the inner portion of the ear canal. Thus, inflammations can be detected by the degree of reddishness.

The electronic imaging unit may comprise a miniature camera, in particular a wafer-level camera of a substantially flat configuration, having dimensions of less than 3 mm×3 mm, preferably less than 2 mm×2 mm, especially 1.2 mm×1.2 mm, even more preferable of about 1 mm×1 mm or even less than 1 mm×1 mm. Wafer-level cameras refer to a relatively new technology. They can be produced small in size with only about 3 microns per pixel. Therefore, wafer-level imaging technology allows obtaining images of "sufficient" resolution of the eardrum, e.g. images of 250 pixels× 250 pixels, with a footprint of the camera including lens of only about 1 mm×1 mm or even smaller.

The term "miniature camera" refers to cameras having minimum dimensions with respect to the required method of capturing images, preferably lateral or radial dimensions in the range of 0.5 mm to 2.5 mm, more preferably in the range of 0.5 mm to 1.5 mm, or 1 mm. A "miniature camera" may exhibit a diameter in the range of e.g. 0.5 mm to 1.5 mm. The dimensions of the camera in an axial direction (parallel to the longitudinal axis) is circumstantial, i.e. only of minor importance. Radial dimensions of less than 2 mm×2 mm, even more preferable of about 1 mm×1 mm provide the advantage that an optical axis of the electronic imaging unit or camera can be arranged very close to an inner or outer lateral surface of the head portion, thereby enabling the otoscope to "look around the corner" with a relatively big angle, e.g. an angle in the range of 10° to 60°, preferably in the range of 15° to 40°, more preferable in the range of 20° to 30°.

A camera based on wafer technology provides a good compromise between light sensitivity and space requirements. The light sensitivity depends on the dimensions of an aperture or lens of the camera. The bigger the aperture, the higher the light sensitivity.

A wide angle camera may enable the otoscope to "look around the corner", in particular in conjunction with a radial offset and/or an optical axis which is tilted against the longitudinal axis of the head portion. A radial offset in conjunction with the ability of a "wide angle" may provide the advantage of "looking around the corner" without the need of an optical axis which is tilted. Nonetheless, the ability of "looking around the corner" can be ensured also by a camera being positioned radially offset and having an optical axis which is tilted. Most effectively, the ability of "looking around the corner" can be ensured by a wide angle camera which is positioned radially offset and which also has an optical axis which is tilted.

According to one specific embodiment, in addition to a radial offset, the electronic imaging unit exhibits a field of vision with a wide angle and/or at least one optical axis which is tilted against the longitudinal axis. Such an electronic imaging unit can provide an otoscope which is arranged for effectively "looking around the corner", as the optical axis is positioned radially offset in conjunction with an optical axis which is tilted against the longitudinal axis and/or in conjunction with a field of vision with a wide angle.

According to one embodiment, the electronic imaging unit comprises at least one miniature camera, preferably at least three to six miniature cameras, especially four cameras, which respectively exhibits dimensions such that it can be arranged radially offset from the longitudinal axis of the head portion, wherein a radial offset with respect to an optical axis or a middle axis of the camera is in the range of 1 mm to 2.5 mm, preferably 1.5 mm to 2 mm, especially at least 1.8 mm. In other words: The type of imaging unit or the components of the imaging unit are chosen such that an imaging unit having at least one optical axis with a relatively large radial offset (especially with a maximum radial offset) with respect to the diameter of the head portion can be realized. A radial offset in these ranges may preferably be realized in conjunction with a relatively large diameter of the distal tip. Providing a radial offset of at least 1.8 mm facilitates "looking around a curvature", even if the distal tip introduced only as deep as a transition area, and even in case an optical axis of the electronic imaging unit is positioned unfavorably.

In case the optical axes are provided by several cameras, preferably, the electronic imaging unit comprises at least three or four cameras, in particular miniature cameras, e.g. wafer-level cameras, which have dimensions such that all cameras can be arranged radially offset (with a maximum radial offset) from the longitudinal axis of the head portion. In particular, the electronic imaging unit comprises three or four miniature cameras, e.g. wafer-level cameras, each having dimensions of about 1 mm×1 mm. The present invention is based on the finding that such small cameras can be arranged with a radial offset which is large enough for enabling the otoscope to "look around the corner", even if the distal tip of the head portion has a (relatively large) diameter in the range of e.g. 4.8 to 5.5 mm, mechanically stopping the head portion at a curvature or transition area between the two types of tissue within the ear canal.

In particular, especially with miniature cameras each having dimensions of about or even less than 1 mm×1 mm, a number of three cameras could be sufficient, as such small cameras can be positioned with a relatively high radial offset. The smaller the camera, the larger the realizable radial offset of an optical axis of the camera. A number of only three cameras also provides the advantage of reduced costs. In case the cameras have dimensions of e.g. about 1.2 mm×1.2 mm or 1.5 mm×1.5 mm, a number of four cameras is preferred. The higher the number of the cameras or optical axes, the higher the likelihood that at least one optical axis is positioned at a favorable eccentric position within the ear canal in order to entirely observe the eardrum. According to one embodiment, the electronic imaging unit comprises four cameras arranged at the same radial offset and having the same distance to each other in a circumferential direction.

A number of three, four, five or six miniature cameras or optical axes can eliminate any need for displacement or rotation of the head portion for positioning a camera in a preferred eccentric observation point. For example, with such an arrangement, it can be ensured that the head portion of the otoscope or the handle portion of the otoscope does not have to be rotated at all. In other words: The layperson only has to introduce the otoscope in an axial direction. It is not required to rotate any part of the otoscope. This reduced the probability of any irritations of the layperson's tissue. Preferably, the electronic imaging unit exhibits a plurality of optical axes which are arranged concentrically, especially rotationally symmetrically with respect to the longitudinal axis of the head portion. According to one embodiment, each optical axis may be provided by one camera.

Nonetheless, irrespective of the number of optical axes, additionally, a motion mechanism can be provided. Providing several cameras, e.g. two or three cameras, in conjunction with a motion mechanism provides the advantage that, if at all, the head portion or the otoscope only has to be rotated by a maximum angle of about 20° to 50°, in order to displace at least one of the cameras in a preferred position for "looking around the corner". A rotating movement of maximum 40° or 50° can position at least one of the cameras in a position in which the eardrum is best visible. Thereby, the present invention is based on the finding that an angle of 40° or 50° can be handled or operated without any problems, especially in an ergonomic way by laypersons, even in context with an application by the layperson. Thus, providing at least two or three, especially four, optical axes may eliminate the need of any motion mechanism. It has been found that more than four cameras or optical axes are not necessarily required. Even, three cameras may be sufficient, in case each optical axis is positioned with a relatively large optical axis. Nonetheless, a number of four cameras seems to be preferred for most applications.

According to one specific embodiment, the electronic imaging unit comprises at least two cameras which exhibit radial dimensions such that they be arranged radially offset from the longitudinal axis of the head portion, wherein a radial offset with respect to an optical axis or a middle axis of the cameras is bigger than a quarter of the diameter of a distal tip of the head portion, preferably bigger than one third of the diameter of a distal tip of the head portion. Providing a camera with such small dimensions can facilitate the otoscope to "look around the corner". The smaller the dimensions of the camera, the larger the radial offset which can be realized. Cameras with such radial dimensions can be arranged very close to the outer lateral surface of the head portion, i.e. very close to an inner lateral surface of the ear canal.

According to one embodiment, the electronic imaging unit comprises at least one camera or optical component like a lens which has radial dimensions which are smaller than ⅓, preferably smaller than ¼, more preferable smaller than ⅕ or ⅙ of a diameter of the distal end or distal tip of the head portion. Such relatively small radial dimensions can ensure that the radial offset is relatively large. Also, such relatively small radial dimensions can ensure that optionally, a plurality of cameras can be arranged on the same pitch circle, the pitch circle having a relatively large diameter.

According to one embodiment, the electronic imaging unit exhibits beam splitter optics defining at least two optical axes which are arranged radially offset from the longitudinal axis. Beam splitter optics provide the advantage that the eardrum can be observed from different points of the distal tip of the head portion, without the need of a plurality of cameras. With beam splitter optics, a relatively large radial offset of each optical axis can be realized, especially a radial offset which can be even larger than the radial offset of an optical axis defined by a camera (even in case a relatively small miniature camera is used). In particular, optical components of the beam splitter optics, such as lenses, mirrors or prisms, can be provided with relatively small radial dimensions. In particular, the optical components can be provided with a radial dimension or diameter smaller than 1 mm, preferably smaller than 0.9 mm, even smaller than 0.8 mm or 0.7 mm.

Also, beam splitter optics can provide an aperture which exhibits relatively large radial dimensions. A large aperture provides for good optical characteristics, especially good light sensitivity and/or a high dynamic range. Also, beam splitter optics can provide an arrangement for "looking around the corner" which is cost-effective.

According to one specific embodiment, the beam splitter optics define a plurality of optical axes which are arranged concentrically, especially rotationally symmetrically with respect to the longitudinal axis of the head portion. Such a design can ensure that the orientation of the head portion within the ear canal can be chosen freely by the user. The user does not have to orientate the handle portion of the otoscope in a specific direction.

Alternatively or in addition, the at least one of the optical axes may be tilted against the longitudinal axis so as to be directed to a predetermined point on the longitudinal axis. Beam splitter optics can provide an arrangement with optical axes with a relatively large tilt angle against the longitudinal axis of the head portion, allowing for "looking around the corner" more effectively than any arrangement with parallel optical axes or with relatively small tilt angles.

Preferably, the electronic imaging unit exhibits an image sensor which is optically coupled with the beam splitter optics, especially with at least two of the optical axes, and which is positioned centrically on the longitudinal axis. An image sensor which is positioned centrically can provide a symmetric design of the imaging unit, which can be favorable also in view of constructing or manufacturing aspects. An image sensor which is arranged centrically can exhibit large radial dimensions, especially as the image sensor can be arranged more proximal in a section of the head portion which exhibits larger radial dimensions than the distal tip. Preferably, the image sensor is provided in conjunction with a plurality of optical axes, e.g. in conjunction with beam splitter optics. In other words: The electronic imaging unit is configured for providing an arrangement with a single image sensor and multiple optical axes. Reducing the number of image sensors can provide an otoscope with a straightforward design, which is cost-effective.

The image sensor may exhibit radial dimensions which are larger than the radial dimensions of any optical component arranged at a distal tip of the otoscope, preferably at least 0.7 mm, more preferable at least 1 mm, further preferred at least 1.5 mm, especially between 1.5 mm and 3 mm. An image sensor which is spaced apart from the distal tip and which is arranged separately from any optical component at the distal tip can be provided with larger (radial, i.e. lateral) dimensions than the optical component, especially any aperture. In particular in conjunction with a conical shape of the head portion, arranging the image sensor proximal to the optical component at the distal tip provided more lateral space (in the radial direction) within the head portion. The larger the image sensor, the better the optical characteristics. In particular, a large image sensor is advantageous for light sensitivity, dynamic range and/or resolution.

The beam splitter optics may comprise at least one mirror and/or prisms and/or at least one lens. These components can provide a high flexibility with respect to the design of the electronic imaging unit. Also, these components allow for large radial offsets, especially as its radial dimensions can be relatively small, e.g. even smaller than the radial dimensions of a miniature camera. For example, the beam splitter optics may comprise at least one prism which exhibits an integral lens. A prism directly including a lens, especially a prism with an integral lens which is made of the same material as the prism, can provide an otoscope with a straightforward design, wherein restricted space conditions within the distal end of the head portion can be exploited. Preferably, an integral lens is a lens which is formed by the prism.

Alternatively or in addition, for each optical axis, the beam splitter optics may comprise concave mirrors, especially two concave mirrors which preferably are provided as aspherical surfaces, wherein a radial offset of the respective optical axis is defined by the two concave mirrors. The relatively low number of only two mirrors for each optical axis can provide an otoscope with a straightforward design, wherein restricted space conditions within the distal end of the head portion can be exploited.

Also, for each optical axis, the beam splitter optics may comprise a plurality of lenses or surfaces, especially two refractive and reflective surfaces and two refractive surfaces, wherein the respective optical axis is defined by the plurality of surfaces. A plurality of optical surfaces can provide high optical fidelity. A suitable combination of refractive and/or reflective aspherical surfaces allows for realization of the desired optical characteristics in a single optical element or block, which can e.g. be a single injection molded PMMA part. The single injection molded part can provide both a support or housing and optical components like lenses.

In particular, for each optical axis, the beam splitter optics can be provided with two refracting lenses and with two both refracting and reflecting lenses. Preferably, the reflecting lenses are tilted with respect to the optical axis, such that a radial offset can be realized.

Alternatively or in addition, for at least one optical axis, the beam splitter optics comprise an optical fibre, especially a gradient index fibre, wherein the respective optical axis is defined by the optical fibre, wherein the respective optical fibre preferably extends between an image sensor of the electronic imaging unit and a distal tip of the head portion. An optical fibre allows for different arrangements of the components of the beam splitter optics with respect to each other. An optical fibre allows for tilting the optical axis. There is no need for any complex arrangement consisting of a plurality of optical components. An optical fibre allows for maximum radial offset irrespective of the space conditions within the distal end or irrespective of any geometrical constraints within the distal end. Also, an optical fibre allows for arranging an image sensor at a relatively large distance from the distal tip, in order to allow for large radial dimensions of the image sensor. Also, an optical fibre allows for minimized use of optical parts or surfaces, i.e. for reduced complexity.

As described above, the specific features of the beam splitter optics may be combined with each other, in order to provide a specific (optimized) electronic imaging unit with respect to specific applications or groups of people.

According to one embodiment, the electronic imaging unit comprises a support or housing defining the radial offset of at least one optical axis and/or accommodating at least one camera and/or beam splitter optics, wherein the support preferably is in contact with an inner lateral surface of the distal end. The support enables exactly positioning or orientating at least one camera, especially a wafer camera, or at least one optical axis of beam splitter optics within the head portion, especially with respect to the longitudinal axis of the head portion. In particular, the support enables concentric arrangement of the optical axes. Concentric arrangement may ensure maximum radial offset irrespective of the rotational position of the head portion within the ear canal.

Preferably, the beam splitter optics are arranged such that the optical axes are positioned with a radial offset which is maximum with respect to the radial dimensions of the distal end. The beam splitter optics can provide an optical path which is directed in the radial direction for an amount or distance which is maximum with respect to the diameter of the head portion. The beam splitter optics can provide a relatively large radial offset. In particular, at least two optical surfaces of an optical path are arranged in a tilt angle with respect to the longitudinal axis such that a maximum radial offset can be realized. Alternatively, two concave mirrors are provided with a surface which is shaped such that a maximum radial offset can be realized.

According to one specific embodiment, the support or housing exhibits an outer lateral surface with a convex shape, at least in sections. A convex shape can ensure that a respective optical axis can be positioned as close as possible to an inner lateral surface of the distal end or tip, adjacent to the inner lateral surface, in order to provide a maximum radial offset with respect to the diameter of the distal end or tip. Preferably, the support encircles the electronic imaging unit, at least its distal end. Also, optionally, a component of the electronic imaging unit, e.g. a camera, can be fixed and/or centered directly at the inner lateral surface, at least partially.

One optical axis of the electronic imaging unit may be positioned substantially centrically with respect to the longitudinal axis of the head portion. If one optical axis of the electronic imaging unit is positioned on the longitudinal axis of the head portion, a substantially flat optical component of the electronic imaging unit is preferable inclined or inclinable with respect to the longitudinal axis of the head portion, so that the one optical axis (or a "viewing direction") of the electronic imaging unit is angled with respect to the longitudinal axis (tilted against the longitudinal axis) of the head portion, allowing the otoscope to "look around the corner" even from a central observation point.

As describes above, the electronic imaging unit may comprise at least one optical axis, e.g. provided by a camera, preferably at least three or four optical axes provided by at least three or four wafer-level cameras which is/are positioned radially offset from the longitudinal axis of the head portion. Such a configuration also allows obtaining a free view onto the eardrum without having to introduce the electronic imaging unit as deeply as it would be necessary if the electronic imaging unit only had one optical axis placed just centrally on the longitudinal axis of the head portion. The offset of all three or four optical axes may be at least 1 mm, preferably at least 1.7 mm, more preferably at least 1.8 mm or at least 1.9 mm, or even (if possible) at least 2.2 mm or 2.5 mm from the longitudinal axis. Preferably, the maximum radial offset is within the limits of the outer diameter of a distal tip of the head portion. The radial offset is in the range of 1 mm to 2.5 mm, preferably 1.5 mm to 2 mm, especially at least 1.8 mm, especially with respect to an optical axis or a middle axis of the at least one camera. An arrangement with a large radial offset, especially in conjunction with a large diameter of the distal tip of the head portion, enables positioning of the camera or an optical axis as close as possible adjacent to an inner wall of the ear canal such that the eardrum can be observed from a preferred position within the ear canal, without the need of introducing the distal tip as far as to the hard bone section of the ear canal.

Preferably, the at least one camera is arranged adjacent to an inner lateral surface of the head portion in such a way that the radial offset is maximum with respect to the radial dimensions of the head portion. Thereby, the radial offset can be maximized.

The optical axis of the at least one camera may be tilted against the longitudinal axis so as to be directed to a predetermined point on the longitudinal axis, the predetermined point having a fixed distance to the at least one camera. A tilted optical axis provides the advantage that, substantially irrespective of the relative position of a head portion of the otoscope within the ear canal, it is more likely that the entire eardrum can be observed.

According to one specific embodiment, the head portion exhibits a supporting structure for fixing a camera of the electronic imaging unit, wherein the supporting structure at least partially radially extends from the longitudinal axis to an inner lateral surface of the head portion, such that the camera can be supported in a position with maximum radial offset.

The head portion is preferably shaped such that (and exhibits radial dimensions such that) its distal end comprising the electronic imaging unit can be introduced only as deep into the ear canal as not to touch the eardrum, especially only as deep as not to touch the hard bone, or at most only as far as some millimeters within the section confined by hard bone. The ear canal of the patient's outer ear is limited by the eardrum. Notably, the ear canal of the patient's outer ear comprises an outer part which refers to a portion of the patient's outer ear (i.e. the patient's external auditory canal) that is surrounded by soft connective tissue and that usually comprises hair and earwax. The outer part comprises approximately the outer half of the ear canal of the patient's outer ear. Furthermore, the ear canal of the patient's outer ear also comprises an inner part which refers to a portion of the patient's outer ear (i.e. the patient's external auditory canal) that is surrounded by hard skull bone and that is usually free from any hair and earwax. This portion extends from the proximal end the outer part of the ear canal of the patient's outer ear to the eardrum. The inner part of the ear canal is very sensitive to pain in case of injury by mechanical friction. Injuring the inner part of the ear canal even bears the risk of cardiovascular complications through vagal overstimulation.

Preferably, the head portion is shaped in such a way that its distal end comprising the electronic imaging unit can be introduced only in an area of the ear canal which is confined by soft connective tissue, but not in an area of the ear canal which is confined by hard bone. On the one hand, such a shape can ensure that the distal end does not touch the eardrum, even if the otoscope is applied by laypersons. On the other hand, the otoscope can be applied by layperson without the need of correcting the position of the head portion within the ear canal. Rather, the head portion only has to be positioned "somehow" within the ear canal, which even can be made by the same person. In other words: There is no need of any assistance at all, which is favorable e.g. for an application by older people living on one's own. The otoscope according to the present invention even can enable an application by the layperson. In particular, the otoscope is arranged to "look around the corner" such that it is sufficient to introduce the head portion only in an area of the ear canal which is confined by soft connective tissue.

Preferably, a tip portion of the distal end can be introduced into the ear canal of the patient's outer ear no further than to a distance from the eardrum of at least a few millimeters, preferably of at least 3 mm, more preferable of at least 10 mm, further preferred of at least 15 mm.

As already mentioned above, the tapering head portion of the otoscope according to the present invention can be shaped with a blunt, rounded tip end, as compared to a conventionally known otoscope, thereby reducing the risk of introducing injury or discomfort to the patient. Thus, the device can be securely handled by laypersons. The otoscope according to the present invention, nevertheless, allows detecting the eardrum, since the electronic imaging unit is provided at the distal end of the head portion, exhibiting at least one optical axis which is radially offset.

Preferably, the distal end of the head portion is provided with a round and smooth shape. Moreover, the distal end may be made from a relatively soft material, such as silicone, or it may comprise an outer surface made of such a soft material. Furthermore, the longitudinal force upon introduction into the ear canal can be limited by a telescoping mechanism or the use of an elastic element.

The functional concept of a conventional otoscope as described above, however, requires the tip end of the head portion to be relatively small and acute (sharp), usually having a diameter of only about 3 mm. It is noted that the diameter of the inner part of the outer ear canal of an adult is about 4 mm. Therefore, if the user (untrained) does not pay attention, the tip portion might be introduced deeply into the inner part of the outer ear canal causing serious injuries to the patient. To substantially avoid this risk, the head portion of the otoscope according to the present invention (also having a tapered shape) preferably exhibits a diameter of at least 4 mm, preferably of more than 5 mm, more preferably of more than 6 mm, at a position along the longitudinal axis of the head portion of no more than 4 mm from a distal end point of the head portion. Thus, it is geometrically excluded to introduce the distal end of the head portion too far into the subject's ear canal. Different geometries of tapers may preferably be used according to the age group of the subject. For children, for example, the head portion of the otoscope adapted to carry out the method according to the present invention may exhibit a diameter of about 5 mm at a position along the longitudinal axis of the head portion of no more than 4 mm away from a distal end point of the head portion. For example, the head portion can be provided with a first specific shape for children at the age of 0 to 2 years and with a second specific shape for any patient at the age of more than 2 years. But, it is not necessarily required to use different geometries of tapers according to the age group of the subject. Rather, the inventive shape of the head portion can be used by all age groups, as it is not required to introduce the head portion far into the subject's ear canal. Thus, the inventive shape of the head portion can provide a universal speculum.

According to one embodiment, the distal tip of the head portion exhibits a diameter, especially an outer diameter, of at least 4.0 mm, at least 4.7 mm, preferably of more than 4.8 mm, more preferably about 4.9 mm. A head portion with a distal tip having a diameter of about 4.7 mm, 4.8 mm or 4.9 mm is not adequate or appropriate for classical otoscopy, especially for observing the eardrum of a child. Such a relatively large tip could not be inserted into the ear canal as far as considerably within the bony part, especially in childrens' ears. The head portion would be blocked at a position too far away from the eardrum, at least within ears of children. It would not be possible to observe the eardrum. There would not be any line of sight onto the eardrum. It would not be possible to align the otoscope within the ear canal such that the eardrum is visible. The head portion would not be introduced far enough for aligning the entire ear canal.

In contrast, according to the present invention, a distal tip with a diameter of about 4.7 mm, 4.8 mm or 4.9 mm can ensure that the distal tip cannot be inserted further into the ear canal than a position within the part of the ear canal which corresponds to a transition area between soft connective tissue and hard bone surrounding the ear canal. In particular, at most, the distal tip of the head portion is docked to or coupled to a proximal end of the bony part. At most, the distal tip of the head portion is positioned at the outer end of the bony part of the ear canal, but not further inwards. In other words: The head portion of the otoscope is preferably shaped in such a way that its distal end comprising the electronic imaging unit or optical component (e.g. camera) can be introduced only as deep into the ear canal as a transition area between soft connective tissue and hard bone confining the ear canal. Preferably, a diameter of an inner lateral surface of the distal end is in the range between at least 4.2 mm, preferably more than 4.4 mm, more preferably about at least 4.5 mm or 4.6 mm, in order to allow maximum radial offset.

The present invention is based on the finding that it is not required to introduce the distal end as far as considerably within the part of the ear canal which is confined by hard bone. Rather, the electronic imaging unit allows for "looking around the corner" even in case the distal tip is introduced only as deep as a transition area between the two types of tissue. Therefore, the electronic imaging unit arranged at the distal tip comprises a camera which preferably exhibits a wide angle, and/or at least one optical axis which is arranged radially offset adjacent to and as close as possible to an inner lateral surface of the distal tip, and/or which has an optical axis which is tilted against the longitudinal axis of the head portion.

In other words: Due to the ability of "looking around the corner", it is possible to shape the head portion such that any contact of the distal tip with the eardrum or even with the bony part of the ear canal can be prevented, especially mechanically. In particular, the present invention is also based on the finding that the ability of "looking around the corner" may permit to provide only one single shape of a head portion, i.e. a kind of "one size fits all" ages or people head portion.

According to one specific embodiment, the head portion exhibits a conical portion with an opening angle α in the range of 3° to 10°, preferably 4° to 8°, especially 5° or 6°. Such opening angles can ensure that, in case the layperson tries to introduce the head portion as far as a section of the ear canal which is confined by hard bone, further insertion of the head portion is blocked within the ear canal well before reaching the eardrum.

According to one specific embodiment, the head portion exhibits a distal tip with a first diameter (d1) in the range of 4 mm to 6 mm, preferably 4.5 mm to 5.3 mm, further preferred 4.7 mm to 5.1 mm, especially 4.9 mm. At a longitudinal position defined by a specific length, the head portion preferably exhibits a second diameter (d2) in the range of 7.5 mm to 9.5 mm, preferably 8 mm to 9 mm, further preferred 8.3 mm to 8.8 mm especially 8.5 mm. Preferably, the ratio of these diameters (d1:d2) is in the range of 0.57 to 0.65, especially about 0.58 or about 0.63. Such a shape can ensure that the head portion is blocked well before reaching the eardrum. Preferably, the specific length is in the range of 18 mm to 22 mm, more preferable 19 mm to 21 mm, especially 20 mm. These diameters or ratios can ensure that the head portion, especially the distal end, exhibits geometrical dimensions ensuring that the head portion can be introduced only in the area of soft connective tissue confining an outer ear canal of the patient's outer ear, but not in the area of hard bone confining the outer ear canal. Such a shape can ensure that the otoscope can be applied by laypersons without the risk of irritations of the tissue.

According to one specific embodiment, the electronic imaging unit exhibits at least one camera with an optical axis which is tilted against the longitudinal axis, wherein the distal end exhibits a conical shape, preferably with a tilt angle (β1) between the longitudinal axis and a lateral surface of the distal end which at least approximately corresponds to the tilt angle of the optical axis. Such a design facilitates an arrangement of the camera with a maximum radial offset. Also, a conical shape of the distal end can facilitate mechanically blocking the head portion within a transition area between the two types of tissue. Preferably, the tilt angle is variable and can be increased.

According to one specific embodiment, at the distal end, the head portion exhibits a maximum wall thickness in the range of 0.1 mm to 0.5 mm, preferably 0.12 mm to 0.3 mm, more preferably 0.13 mm to 0.2 mm, especially 0.15 mm at the maximum. Such a relatively low wall thickness enables positioning the (respective) optical axis with a maximum eccentricity with respect to the radial dimensions of the distal tip. The lower the wall thickness, the larger the radial offset which can be realized.

According to one specific embodiment, the head portion and/or the handle portion exhibits fixation means for fixing a probe cover at the otoscope. Thereby, a probe cover can be fixed at the head portion or handle portion such that relative motion can be prevented. Such fixations means can prevent premature unfolding of the probe cover, as relative motion between the head portion and a probe cover is only enabled at a time when the distal tip is introduced far enough. The risk of ear wax obstructing visual communication can be minimized.

The features relating to the shape of the head portion, as described above, may be combined with each other, in order to make the concept of "looking around the corner" more practicable, even in context with an application by laypersons.

When introducing the tip end of the head portion no deeper into the ear canal than to the border between the outer part and the inner part of the outer ear canal of the patient's outer ear, i.e. to a transition area between the two types of tissue, there is the risk that artifacts, such as earwax, hair and other kind of dirt from the outer part of the outer ear canal obstruct the view of the small electronic imaging unit onto the patient's eardrum. Therefore, it is advantageous to take several images from different positions within the ear canal. For doing so, the otoscope according to the present invention may comprise more than one optical axis or cameras at the distal end of its head portion, e.g. two optical axis or cameras, located at different positions on the head portion, wherein the otoscope comprises a logic unit which is configured for controlling each camera or beam splitter optics for capturing a plurality of different images, especially from eccentric observation points which are arranged on the same semi circle of an at least approximately circular cross section of the ear canal.

In another preferred embodiment, the otoscope according to the present invention further comprises a motion mechanism configured to allow displacement of the electronic imaging unit or the at least one optical axis of the electronic imaging unit or at least one camera of the electronic imaging unit relative to the handle portion. With such a motion mechanism, it is possible to position the at least one optical axis in a favorable eccentric observation point, substantially irrespective of the position of the head portion within the ear canal. Also, with such a motion mechanism, it is possible to capture a plurality of images from different positions from one optical axis within the patient's ear canal, thereby avoiding the need for two or more cameras. If, for example, a hair—at least partially—obstructs the view of the electronic imaging unit at a certain position within the ear canal onto the eardrum, the electronic imaging unit may have a free view onto the eardrum at another position in the ear canal or may at least have a free view onto the part of the eardrum that was partially obstructed by the hair before.

It has been found that positioning the at least one optical axis radially offset induces or brings about that the eccentric observation point positioned at the distal tip on this least one optical axis may be positioned at an unfavorable position, e.g. adjacent to a section of the ear canal having a minimal radius of curvature. Therefore, departing from at least one a radially offset optical axis, the motion mechanism may facilitate to make the concept of "looking around the corner" more practicable.

Moreover, providing such a motion mechanism also allows for automatic identification of different objects in the patient's ear. Usually, in otoscopy, the eardrum represents the object of primary interest. In contrast, artifacts, such as earwax, hair and other kind of dirt, are usually of no particular interest. Such artifacts rather represent a problem when obstructing the view onto the patient's eardrum.

However, since artifacts are relatively close in front of the electronic imaging unit in the ear canal, compared to the eardrum, the artifacts can be distinguished from the eardrum when displacing the electronic imaging unit within the ear canal. That is, artifacts are depicted at distinct positions, if two images are captured from different positions/perspectives within the ear canal (due to their short distance to the electronic imaging unit), whereas the eardrum is shown substantially at the same position (due to the relatively large distance to the electronic imaging unit). According to the principle of stereoscopic viewing, the inventive device enables to determine the distance of different objects with respect to the electronic imaging unit. This determination can be automatically calculated by means of a logic unit, such as a microprocessor, preferably forming part of the otoscope. Furthermore, objects that have been identified as artifacts (due to their close distance to the electronic imaging unit) may be (automatically) eliminated by the image processing unit by comparing two or more images captured from different positions within the patient's ear canal. Consequently, a superimposed image may be generated or calculated by image processing means eliminating the artifacts. The image processing means may be implemented in form of a logic unit, such as a microprocessor provided in the otoscope. Thus, an image clearly depicting the eardrum can be obtained, even if the tip end of the head portion is introduced into the ear canal to the border between the outer part and the inner part of the outer ear canal (and not deeper into the ear canal).

The motion mechanism may be arranged within the handle portion, wherein the motion mechanism preferably includes a drive shaft which is preferably arranged on the longitudinal axis. Preferably, the motion mechanism is arranged completely separate from the head portion. Such an arrangement can provide a straightforward design with low acoustic emission into the ear.

Preferably, the motion mechanism includes a motor. A motor allows for automatically position the optical axis. The motor can be provided e.g. in the form of a brushless motor, especially in order to minimize any noise evoked or generated by the motor. Brushless motors can be accelerated softly by ramp up of angular speed of the rotating magnetic field. Rotational vibration can be minimized. A noise reduced brushless motor provides the advantage that any noise or acoustic emission of the motor does not trouble or confuse the patient during the application of the otoscope. Preferably, the motion mechanism, especially the motor is configured for rotating the electronic imaging unit by an angle of about 180°.

The motion mechanism is preferably configured to allow at least partial rotation of the electronic imaging unit or the at least one optical axis or the at least one camera about an axis of rotation. The axis of rotation may correspond to the longitudinal axis of the head portion. By displacing the electronic imaging unit along a predefined motion path, it is possible to automatically calculate the distance of the electronic imaging unit to the detected objects, as described above. In view of the typical size of the artifacts found in the ear canal, such as hair and earwax particles, the motion mechanism preferably allows for displacement of the optical axis of at least 1 mm, more preferable at least 2 mm, further preferred at least 3 mm, within the patient's ear canal. For example, in case a radial offset of 1.8 mm or 2 mm is realized, a rotation of 90° evokes a displacement of about 3 mm. A rotation of at least 90°, more preferably of at least 120°, even more preferably of 180° or even more degrees around the axis may be realized. In conjunction with an electronic imaging unit exhibiting two optical axes or comprising two cameras, a rotation of maximum 90° may be adequate in order to find the most favorable eccentric observation point. In conjunction with an electronic imaging unit exhibiting three optical axes or comprising three cameras, a rotation of maximum 60° or 70° may be adequate. Preferably, the motion mechanism allows for rotation in both directions, i.e. clockwise and counter-clockwise. The motion mechanism may also allow for rotational displacement about more than one axis. The motion mechanism may comprise at least one motor and one or more gears and/or bearings. The electronic imaging unit may be connected to a flexible cable, e.g. a flexible ribbon cable, to allow for such a movement.

An axis of rotation corresponding to the longitudinal axis of the head portion allows for displacing the at least one optical axis concentrically around the longitudinal axis. Thus, irrespective of the relative position of the optical axis, a maximum radial offset can be ensured.

Preferably, an optical component of the electronic imaging unit or at least one optical axis of the electronic imaging unit or at least one camera is tilted against the axis of rotation so as to be continuously directed to a predetermined point on the axis of rotation, especially during a rotation by the motion mechanism, the predetermined point having a fixed distance to the electronic imaging unit or to the camera. In view of the typical length of the inner part of the outer ear canal of the patient's outer ear, the distance may be between 3 mm and 20 mm, preferably between 10 mm and 15 mm. Thus, the "viewing direction" of the electronic imaging unit is optimized for centering on the eardrum, which usually represents the object of primary interest within the patient's ear. Also, the "viewing direction" remains directed onto the central point of interest, even in case there is relative rotation induced by the motion mechanism. In conjunction with a specific shape of the head portion ensuring that the distal tip is mechanically blocked at a transition area between the two types of tissue, a fixed distance to the most distal component of the electronic imaging unit may be fixed with respect to the respective length of the section of the ear canal between the transition area and the eardrum. Such an arrangement may facilitate application by laypersons.

In addition, the otoscope may further comprising at least one mechanism configured to allow displacement of the electronic imaging unit or the at least one optical axis or at least one camera of the electronic imaging unit relative to the handle portion in conjunction with tilting it against the longitudinal axis. Such a combined mechanism, or two motion mechanisms combined with each other, especially two motion mechanisms which are controllable in dependence on each other, allow for "looking around the corner" more effectively. In particular, axially displacing or rotating an optical axis in conjunction with tilting the optical axis can enable observation of the entire eardrum, even from an observation point with a relatively small radial offset, or positioned unfavorably within the ear canal.

For hygienic reasons, the otoscope preferably further comprises an at least partially transparent probe cover configured to be put over the head portion. The probe cover may be made from a plastic material, preferably from a transparent plastic material. Such a probe cover may be designed as a single-use product that can be produced in larger numbers with low costs. The probe cover shall be transparent, at least at the locations where it covers an eccentric observation point, i.e. where it intersects an optical axis of the electronic imaging unit, so as to allow the electronic imaging unit to have a clear view onto the eardrum. The probe cover also inhibits contamination of the head portion of the otoscope comprising the electronic imaging unit, in particular when introducing the head portion into the patient's ear canal.

Preferably, the probe cover is adapted to be fixed to at least one section of either the head portion and/or the handle portion in such a way that the probe cover does not move relative to the handle portion during displacement of the electronic imaging unit or at least one optical axis or at least one camera by the motion mechanism. Otherwise, artifacts, such as earwax particles, adhering to the probe cover will depicted by the electronic imaging unit, even if the electronic imaging unit is displaced by the motion mechanism. This, however, would interfere with object identification and elimination of artifacts from the captured images.

The otoscope may further comprise a probe cover moving mechanism adapted to move at least a portion of the probe cover with respect to the electronic imaging unit or at least one optical axis or at least one camera. Thus, artifacts, such as earwax particles, adhering to the probe cover and obstructing the view of the electronic imaging unit or camera onto the eardrum can be moved away from the electronic imaging unit by the probe cover moving mechanism.

In particular, the probe cover moving mechanism can ensure that an optical axis of the electronic imaging unit can be arranged with a relatively large radial offset, especially without evoking the problem of any earwax particles obstructing visibility or with reduced probability of such earwax particles. Earwax particles are often arranged at an inner surface surrounding the ear canal. Thus, for an optical axis being arranged with a high radial offset, i.e. close to an inner lateral surface of the ear canal, there may be an increased likelihood of earwax particles adhering to the probe cover at a section covering the optical axis, thereby obstructing the view onto the eardrum. In other words: There may be an increased likelihood of earwax particles obstructing the view from an optical axis which is radially offset than from an optical axis which is arranged at least approximately centrically. The probe cover moving mechanism can ensure that the view onto the eardrum is not obstructed, even in case the optical axis is arranged with a maximum radial offset close to an inner lateral surface of the ear canal. Thus, the present invention is based on the finding that by providing a probe cover moving mechanism, observation of the eardrum from an eccentric observation point with a relatively large radial offset can be made more practicable and more reliable. A probe cover moving mechanism can ensure that the concept of "looking around the corner" is feasible and can be realized in a convenient way, even in case the ear canal is obstructed by several objects.

The probe cover moving mechanism can be provided e.g. in the form of a latch mechanism or an automatized mechanism which is driven by a motor. The probe cover moving mechanism allows for controlled, predefined relative displacement, especially in an axial direction, i.e. parallel to the longitudinal axis of the head portion. Preferably, the probe cover moving mechanism interact with a proximal portion of the probe cover and is configured for an axial motion or displacement of the probe cover or a portion of the probe cover, be it in a distal and/or in a proximal direction. As an alternative or in addition, the probe cover moving mechanism can be configured for rotating the probe cover.

Preferably, the probe cover is designed in a way that allows unfolding or peeling of portions of the probe cover in order to move portions of the probe cover contaminated e.g. with earwax away from the electronic imaging unit. The otoscope preferably contains mechanical means to move the probe cover against the electronic imaging unit or vice versa.

To illuminate the patient's ear canal and eardrum, the otoscope may further comprise at least one light source typically positioned at the distal end of the head portion, especially at the distal tip of the head portion. The term "light source" is understood to apply to any source emitting photons. A light source positioned at the distal end or tip ensures illumination of the ear canal, even in case the distal tip is only introduced as deep as a transition area between the two types of tissue. Distal light sources facilitate realization of the concept of "looking around the corner".

Since geometrical restrictions limit the space at the distal end of the head portion, the light source is preferably formed by the distal end of a light guide. For example, the light guide may exhibit a diameter of less than 1 mm, preferably of less than 0.5 mm, more preferably of about 0.2 mm. The light guide may be connected to an LED located remote from the distal end of the head portion. The light guide may be e.g. a nylon light guide, preferably having a diameter of only about 0.2 mm to 1 mm. Alternatively, a light source may be formed e.g. by a small light emitting diode (LED) that is placed directly at the distal end of the head portion. The LED can ensure illumination with low energy consumption and minimum generation of heat.

The light guide can be made of polymethyl methacrylate (PMMA) or polyamide, especially polyamide 6.6. PMMA provides the advantage of good optical characteristics. Polyamide 6.6 provides the advantage of high flexibility. The light guide may allow placement of the light source at a distance from the distal end with less spatial constrains and space for means (e.g. a printed circuit board) for effective heat dissipation. Such an arrangement facilitates realization of the concept of "looking around the corner", especially as the light guides may be arranged with a maximum radial offset without any risk of thermally damaging tissue. Effective heat dissipation reduces the impact of the otoscope on the tissue confining the ear canal, avoiding thermal irritation of the tissue.

It is advantageous, if the otoscope comprises a plurality of light sources at the distal end of the head portion, preferably with each light source being separately controllable. Thereby, the ear canal can be illuminated from a favorable eccentric illumination point, reducing e.g. shadowing. Also, by illuminating objects in the patient's ear canal from different positions, e.g. by sequentially switching on and off the individual light sources, it may also be envisaged to distinguish different objects in the ear, without necessarily having to displace the electronic imaging unit by a motion mechanism within the ear canal. An object relatively far away from the electronic imaging unit, such as the eardrum, will change its appearance only slightly when being illuminated from different positions at the distal end of the head portion. However, artifacts that are relatively close to the electronic imaging unit (such as hair and earwax) will change their appearance (position) drastically. The otoscope therefore preferably comprises means, in particular a logic unit, such as a microprocessor, adapted to distinguish different objects in the patient's ear based on images taken with the objects being illuminated from different positions.

Preferably, a logic unit is coupled with at least two of the light sources and is arranged for individually switching on and off the light sources and/or for individually varying the light intensity.

Additionally or alternatively, the at least one light source may be controllable in view of the color, so that it is possible to change the color of the light emitted by the light source.

For example red color may be preferred to recognize an inflamed eardrum, wherein green color may be preferred to recognize earwax.

According to one specific embodiment, the otoscope comprises the logic unit, wherein the logic unit is coupled with at least two of the light sources and is arranged for individually switching on and off the light sources and/or for individually varying the light intensity. Individually switching on and off enables stereoscopic viewing, especially depth analysis along the optical axes due to changes in reflected light patterns. Also, segmented lighting of the ear canal can be carried out. For example, three light sources each illuminate a specific portion of the ear canal. Feedback regulation of each of the light sources allows for homogeneous illumination of the ear canal, especially based on different illumination levels. Preferably, a logic unit is coupled to each of the light sources, the logic unit allowing for feedback regulation and/or adjustment of illumination levels.

According to one specific embodiment, the otoscope comprises the logic unit, wherein the logic unit is arranged for adjusting an intensity of illumination provided by the least one light source, wherein the least one light source preferably is dimmable, especially continuously dimmable. Adjusting the illumination level facilitates identification of the eardrum, in particular in dependence on the degree of reddishness of the eardrum with respect to surrounding tissue and with respect to a specific intensity of illumination. Preferably, the logic unit comprises at least one dimmer switch.

Like the electronic imaging unit, the at least one light source is preferably positioned radially offset from the longitudinal axis of the head portion. Such a configuration allows illumination of the eardrum without the need to introduce the light source as deeply into the ear canal as it would be necessary, if the light source were placed centrally on the longitudinal axis of the head portion. The offset may be at least 1 mm, preferably at least 1.5 mm, more preferably at least 2 mm from the longitudinal axis. Preferably, the offset is maximum with respect to the confines of the outer diameter of the head portion. According to one embodiment, the offset is in the same range as a radial offset of the at least one optical axis. According to one embodiment, the radial offset of the at least one light source is as large as a radial offset of a camera of the electronic imaging unit. Such an arrangement is favorable in order to observe the entire eardrum or in order to reduce shadowing.

The radial offset preferably is in the range of 1.8 mm to 2.5 mm, more preferable 1.9 mm to 2.3 mm, further preferable 2.0 mm to 2.1 mm. Such a radial offset can ensure that light is effectively emitted onto the eardrum, irrespective of the relative position of a head portion of the otoscope within the ear canal, especially irrespective of any specific insertion depth into the bony part of the ear canal, i.e. the section confined by hard bone. According to one embodiment, the radial offset is not larger than the radial offset of the at least one optical axis. This arrangement can ensure that light is emitted within the ear canal, reflections from inner lateral surfaces of the ear canal being minimized.

Preferably, the at least one light source is positioned adjacent to the at least one optical axis, preferably in a distance (b) smaller than 2 mm, more preferable smaller than 1.5 mm, further preferable smaller than 1.3 mm, especially between 1 mm and 1.3 mm or between 0.6 mm and 0.8 mm. Such an arrangement can enable emission of light with respect to one specific camera or optical axis. In particular, shadowing can be reduced. Light can be emitted onto the eardrum from a favorable position, especially e.g. in a direction which is at least approximately parallel to the ear canal. Also, an arrangement close to the optical axis can ensure that the light source can easily be displaced in conjunction with the optical axis in order to position the light source at a favorable eccentric illumination point.

According to one embodiment, the otoscope exhibits at least two light sources or light guides which are arranged in a maximum distance (d) apart from each other, wherein the maximum distance (d) is at least 3.5 mm, more preferable at least 4 mm, further preferred in a range between 4.2 mm and 4.6 mm. Such an arrangement is favorable in order to observe the entire eardrum, especially without the need of rotating the camera or light source in a specific position. The relatively large distance can ensure that it is likely that one of the at least two, three or four light sources is arranged in a favorable eccentric illumination point.

Preferably, the at least one light source is arranged so as to maintain a predetermined distance with respect to the electronic imaging unit or the at least one optical axis, even when the electronic imaging unit or the at least one optical axis is displaced by the motion mechanism. Such a configuration is advantageous, because the predetermined distal relationship between the at least one light source and the optical axis allows for improved (automatic) image analysis. If a motion mechanism is provided, the motion mechanism preferably also displaces the at least one light source. If the light source is provided in the form of a light guide, the light guide should be sufficiently flexible to allow for such a displacement of the at least one light source. Preferably, the light guide is fixed distally within the head portion, wherein the light guide is elastic, the elasticity allowing for bending and/or twisting. Alternatively, the light guide may be rigid, wherein the entire lightning apparatus may be displaced in conjunction with the head portion.

According to one embodiment, the at least one light source is coupled with the motion mechanism, especially directly or via the electronic imaging unit, such that the motion mechanism allows for at least partial rotation of the at least one light source about an axis of rotation, wherein the axis of rotation preferably corresponds to the longitudinal axis. Rotating the light source in a favorable position can allow for observing the entire eardrum with a high reliability.

The at least one light source may be fixed at the electronic imaging unit, in particular laterally fixed at a camera of the electronic imaging unit or at a support accommodating at least one optical component of the electronic imaging unit or defining the least one optical axis. With such an arrangement, rotation of both the electronic imaging unit and the light source can be realized quite easily. Thereby, the motion mechanism only has to be coupled with one of these components.

According to one embodiment, the otoscope further comprises an infrared sensor unit positioned at the distal end of the head portion, especially centrically. Providing an otoscope comprising an infrared sensor unit for temperature detection in conjunction with an optical identification of objects allows for more reliable identification of the objects, e.g. of the eardrum. Providing an otoscope additionally with an infrared sensor unit allows for minimizing any risk of misdiagnosis. Pre-diagnosis may be facilitated. Temperature detection may assist a physician in carrying out diagnosis. End diagnosis will be carried out by the physician. Any more advanced or final disease diagnosis has to be carried out by the physician on the basis of other symptoms exhibited by the subject, which are observed by the physician, or by the physician's further examination.

The infrared sensor unit may be provided as a component of the electronic imaging unit, or as a separate sensor unit. The infrared sensor unit can be connected to a logic unit, the logic unit being configured for processing data from both the infrared sensor unit and the electronic imaging unit, especially simultaneously. Data acquired by the infrared sensor unit can be verified based on data acquired by the electronic imaging unit, and vice versa. The infrared sensor unit can be provided at same positions like positions discussed in context with the electronic imaging unit or the light sources. Likewise, the infrared sensor unit can be displaced in the same manner as discussed in context with the electronic imaging unit or the light sources.

As described above, the otoscope may further comprise a logic unit, such as a microprocessor. The logic unit may be adapted to control the electronic imaging unit and/or the at least one light source and/or an infrared sensor unit and/or any one of the motion mechanisms or moving mechanism. Also, the logic unit may analyze the images obtained by the electronic imaging unit e.g. in order to detect an inflammation of the eardrum and/or the inner part of the outer ear canal, and/or in order to compare two images obtained with the electronic imaging unit located at different positions within the ear and/or with the object illuminated from different positions, so as to identify and discriminate different objects in the patient's ear. The logic unit may further be adapted to generate or calculate a new image wherein predetermined objects that have been previously identified are eliminated.

According to one particular embodiment, the above mentioned object is achieved according to the present invention by an otoscope comprising: a handle portion allowing a user to manipulate the otoscope during its application; and a head portion exhibiting a substantially tapering form extending along a longitudinal axis of the head portion, wherein the head portion has a proximal end adjacent to the handle portion and a smaller distal end configured to be introduced in an ear canal of a patient's outer ear, wherein the otoscope further comprises an optical electronic imaging unit positioned at the distal end of the head portion, especially at a distal tip of the head portion, wherein the electronic imaging unit exhibits at least two, especially three or four, optical axis which are positioned radially offset from the longitudinal axis, wherein the distal end is configured for accommodating the electronic imaging unit in such a way that the radial offset can be maximum with respect to the diameter of the distal end, and wherein the electronic imaging unit exhibits beam splitter optics, especially provided as single injection molded part, or one part for each light path or optical axis, defining at least two of the optical axes, the at least two of the optical axes being arranged concentrically, especially rotationally symmetrically with respect to the longitudinal axis of the head portion. Such an otoscope provides the advantages as discussed above in context with the respective features.

According to one particular embodiment, the above mentioned object is achieved according to the present invention by an otoscope comprising: a handle portion allowing a user to manipulate the otoscope during its application; and a head portion exhibiting a substantially tapering form extending along a longitudinal axis of the head portion, wherein the head portion has a proximal end adjacent to the handle portion and a smaller distal end configured to be introduced in an ear canal of a patient's outer ear, wherein the otoscope further comprises an optical electronic imaging unit positioned at the distal end of the head portion, especially at a distal tip of the head portion, wherein the electronic imaging unit exhibits one optical axis which is positioned radially offset from the longitudinal axis, wherein the distal end is configured for accommodating the electronic imaging unit in such a way that the radial offset can be maximum with respect to the diameter of the distal end, wherein the electronic imaging unit comprises a miniature camera, the radial offset with respect to the optical axis or a middle axis of the camera being in the range of 1 mm to 2.5 mm, preferably 1.5 mm to 2 mm, especially at least 1.8 mm, and wherein the otoscope comprises a motion mechanism configured to allow displacement, especially rotation, of the camera relative to the handle portion. Such an otoscope provides the advantages as discussed above in context with the respective features.

The above mentioned object is achieved according to the present invention by an otoscope comprising: a handle portion allowing a user to manipulate the otoscope during its application; and a head portion exhibiting a substantially tapering form extending along a longitudinal axis of the head portion, wherein the head portion has a proximal end adjacent to the handle portion and a smaller distal end configured to be introduced in an ear canal of a patient's outer ear, wherein the otoscope further comprises an optical electronic imaging unit positioned at the distal end of the head portion, especially at a distal tip of the head portion, wherein the electronic imaging unit exhibits at least two, especially three or four, optical axis which are positioned radially offset from the longitudinal axis, wherein the distal end is configured for accommodating the electronic imaging unit in such a way that the radial offset can be maximum with respect to the diameter of the distal end, wherein the electronic imaging unit comprises at least two, especially three or four, miniature cameras, the radial offset with respect to the optical axis or a middle axis of the cameras preferably respectively being in the range of 1 mm to 3 mm, preferably 1.5 mm to 2.5 mm. A plurality of eccentric cameras provide favorable eccentric observation points, especially without the need for any motion mechanism.

According to the present invention, the above mentioned object is also achieved by an otoscope comprising: a handle portion allowing a user to manipulate the otoscope during its application; and a head portion exhibiting a substantially tapering form extending along a longitudinal axis of the head portion, wherein the head portion has a proximal end adjacent to the handle portion and a smaller distal end configured to be introduced in an ear canal of a patient's outer ear, wherein the otoscope further comprises an optical electronic imaging unit positioned at the distal end of the head portion, especially at a distal tip of the head portion, wherein the electronic imaging unit exhibits four optical axes which are positioned radially offset from the longitudinal axis, wherein the distal end is configured for accommodating the electronic imaging unit in such a way that the radial offset can be maximum with respect to the diameter of the distal end, wherein the electronic imaging unit further comprises a number of four to eight, especially four, light sources positioned radially offset from the longitudinal axis at the distal end, wherein at least one light source is correlated or allocated or attributed to a respective optical axis, and wherein the radial offset of the light sources is in the range of 1 mm to 2.5 mm. Correlating at least one light source with each optical axis, especially correlating four light source or five, six, seven or eight light sources with four optical axes, provides the advantage that the ear canal can be illuminated and analyzed from favorable eccentric illumination points as well as from favorable eccentric observation points, substantially irrespective of the relative position of a head portion of the otoscope within the ear canal, or substantially irrespective of the relative (rotational) orientation position of the head portion within the ear canal.

DESCRIPTION OF THE FIGURES

Exemplary embodiments of the present invention will be described in more detail in the following with respect to the drawings, wherein:

FIG. 1 schematically shows a cross-sectional view of a head portion and of a part of a handle portion of an embodiment of an otoscope according to the present invention;

FIG. 2 shows an enlarged view of a plate covering a bore provided in the head portion illustrated in FIG. 1;

FIG. 23A schematically shows an otoscope according to the present invention, with its head portion partially introduced into the patient's ear canal;

FIG. 23B schematically shows the otoscope shown in FIG. 23A with its head portion introduced into the patient's ear canal as far as to an end position from which the eardrum can be observed;

In case any reference sign is not explicitly described in a respective figure, it is referred to the other figures. In other words: Like reference characters refer to the same parts or the same type or group of device throughout the different views.

DESCRIPTION OF PREFERRED EMBODIMENTS

Figure 3:
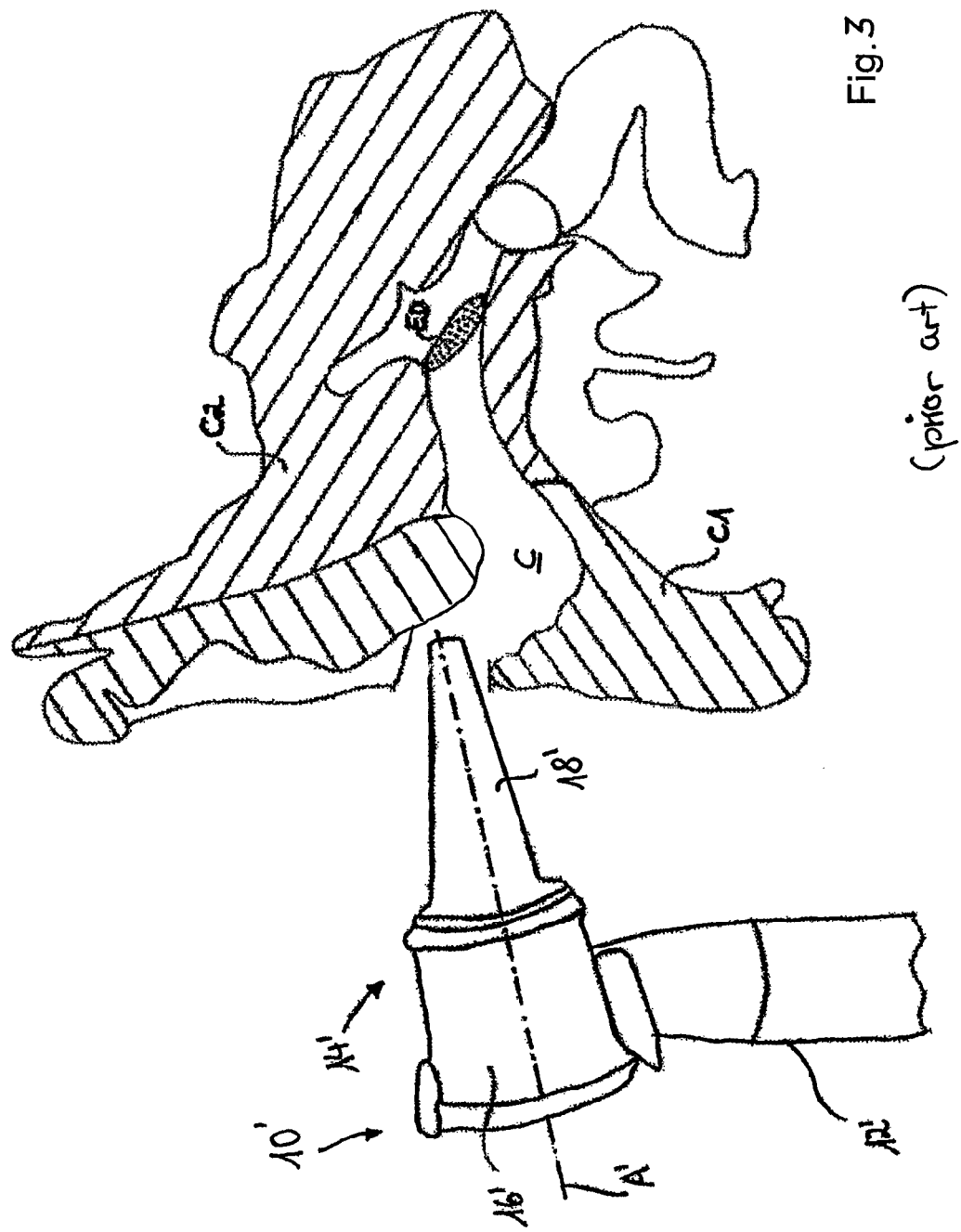
FIG. 3 shows an otoscope of the prior art, with its head portion partially introduced into the patient's ear canal.
Figure 4:
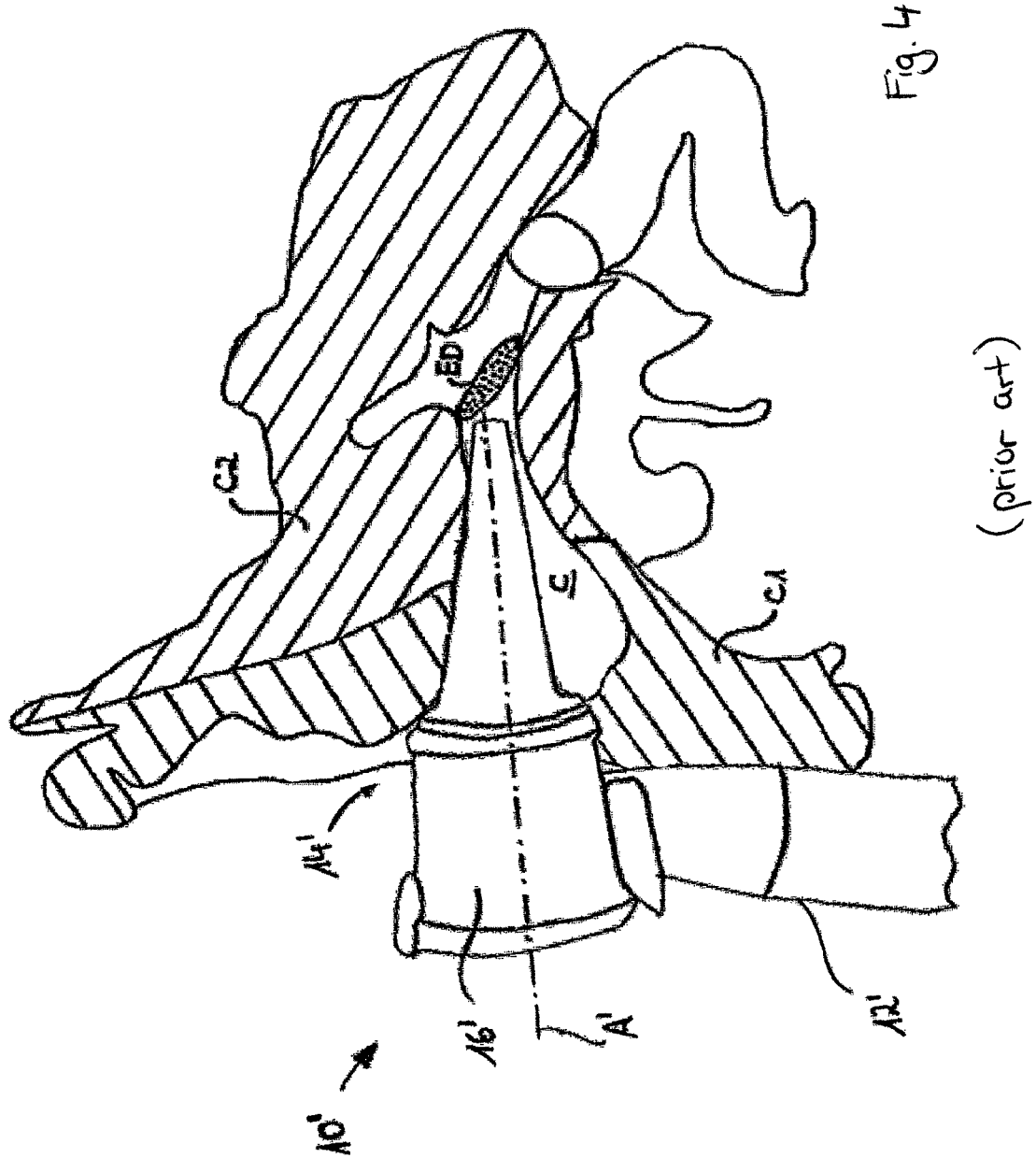
FIG. 4 shows the otoscope of FIG. 3 with its head portion fully introduced into the subject's ear canal.

FIG. 1 schematically shows a cross-sectional view of a head portion 14 and a part of a handle portion 12 (only shown in phantom lines) of an embodiment of an otoscope 10 according to the present invention. As can be seen from FIG. 1, the head portion 14 has a substantially tapering form extending along a longitudinal axis A of the head portion 14. The head portion 14 comprises a relatively large proximal end 16 adjacent to the handle portion 12 and a smaller distal end 18. The distal end 18 of the head portion 14 is adapted to be introduced into a patient's ear canal.

Furthermore, the head portion 14 comprises a rotatable, radial inner portion 20 and a fixed, radial exterior portion 22. The rotatable portion 20 is rotatable about an axis of rotation R which—in the shown exemplary embodiment—corresponds to the longitudinal axis A of the head portion 14. A motion mechanism 24 comprising a servo motor 26 is positioned within the handle portion 12 and is coupled to the rotatable portion 20 of the head portion 14, so as to rotate the rotatable portion 20 about its axis of rotation R relative to the fixed portion 22 of the head portion and relative to the handle portion 12 of the otoscope 10. The rotatable portion 20 is supported by a radial bearing 28 (also only schematically shown).

In the shown exemplary embodiment, the exterior portion 22 of the head portion 14 comprises a support structure 30 providing the required stability to the head portion 14. The support structure is at least partially covered by an outer cladding 32 formed from a relatively soft material, such as silicone. The cladding 32 makes it more comfortable for the patient to introduce the distal end 18 of the head portion 14 into his ear canal. The cladding may comprise a circular slot-like recess 33 adapted to engage with a complementarily formed circular tongue of a (not shown) probe cover. The probe cover may be formed from a plastic material and may be adapted to be put over the head portion 14. Preferably, the probe cover is formed from a transparent material. Its wall may be relatively thin, thereby making the probe cover relatively flexible. At least a portion of the probe cover covering the distal end 18 of the head portion 14 should be transparent, so as to allow an electronic imaging unit (described in the following) which is located at the distal end 18 of the head portion 14 to have a free view through the probe cover. For hygienic reasons, the probe cover is preferably designed as a single-use product. The probe cover also reliably inhibits contamination of the distal end 18 comprising the electronic imaging unit. Without such a probe cover there is a high risk that e.g. earwax particles may adhere to the electronic imaging unit (thereby deteriorating the image quality thereof) when introducing the distal end 18 into the outer part of the outer ear canal of the patient.

The head portion 14 comprises a distal end point 34 which, in the shown exemplary embodiment, is located substantially on the longitudinal axis A of the head portion 14. However, the head portion 14 might alternatively have a tapering shape that is not substantially symmetrical to its longitudinal axis A (as shown in FIG. 1) but is more adapted to the anatomy of the human ear canal.

Irrespective of the precise shape of the head portion 14, the head portion 14 is preferably dimensioned in such a way that it cannot be introduced into the inner part of the outer ear canal of the patient's outer ear. In the shown exemplary embodiment, the distal end 18 of the head portion 14 has a substantially round shape. Only a few millimeters (less than 4 mm) away from the distal end point 34 in the direction of the longitudinal axis A, the head portion 14 exhibits a diameter of more than 5 mm. Since the inner part of the outer ear canal of an adult usually exhibits a diameter of 4 mm, there is no risk that the distal end 18 of the head portion 14 is inadvertently introduced too deeply into the patient's ear canal. Therefore, injuries to the sensitive skin of the inner part of the outer ear canal and/or to the eardrum can be reliably avoided.

The movable portion 20 comprises a bore 36 or a tubing extending substantially along the axial direction A of the head portion 14, but not exactly parallel thereto. The distal end of the bore 36 is located in proximity to the distal end point 34, but offset with its bore axis B by at least 2 mm from the longitudinal axis A. Furthermore, the distal end of the bore 36 is closed by a plate 38. An enlarged top view of the plate 38 is shown in FIG. 2. Since the bore 36 is cylindrical in shape, the plate 38 has a generally circular appearance in FIG. 2 with the bore axis B forming the center thereof. However, the bore 30 and/or the plate 38 may equally exhibit other shapes.

The plate 38 supports an electronic imaging unit 40 comprising a wide-angle color video camera 40.1 and distal ends of four light guides 42. In the exemplary embodiment, the light guides 42 are located around the electronic imaging unit 40 or camera 40.1, such that one light guide 42 is associated to each of the four lateral sides of the substantially rectangular electronic imaging unit 40 or camera 40.1. However, this is not a prerequisite for the present invention. Instead of four light guides 42, for example, only two or three light guides 42 may be provided in the otoscope 10. The electronic imaging unit 40 comprises advantageously a wafer-level camera of dimensions in the 1 to 2 mm range having a substantially flat configuration. The wafer-level camera advantageously exhibits dimensions of only about 1 mm×1 mm providing a resolution of about 250 pixels of 250 pixels. The plate 38 has a diameter between 1.5 mm and 2.0 mm and the light guides 42 have a diameter of only about 0.2 mm.

The video camera 40.1 of the electronic imaging unit 40 is connected to a distal end of a cable (not shown). The cable, e.g. a ribbon cable, extends through the bore 36 and into the handle portion 12 of the otoscope 10. A distal end of the cable is connected to a logic unit 44, such as a microprocessor, which is schematically illustrated in FIG. 1. Similarly, the light guides 42 (not shown in FIG. 1) extend through the bore 36 and into the handle portion 12 of the otoscope 10. Proximal ends of the light guides 42 are connected to four LEDs 46, respectively. The LEDs 46 are positioned—like the logic unit 44—within the handle portion 12 of the otoscope 10. The LEDs 46 can be individually switched on and off. Furthermore, the handle portion 12 preferably comprises a memory 48 for storing images captured by the electronic imaging unit 40 or camera 40.1. The memory may be formed e.g. by a storage card slot and a corresponding storage card inserted in the slot. The handle portion 12 may further comprise a display (not shown) for displaying the images taken by the electronic imaging unit 40 or camera 40.1 to the user. Additionally or alternatively, the handle portion 12 may comprise a cable connection port, such as an USB-port, and/or a wireless connection, such as Bluetooth®, WIFI® and/or an energy supply, such as a (rechargeable) battery. These additional (optional) components of the handle portion 12 are known e.g. from digital cameras.

For capturing images of a patient's inner part of the outer ear canal, and in particular of a patient's eardrum, the distal end 18 of the head portion 14 has to be introduced into the patient's ear canal. Due to the shape of the head portion 14 there is no risk to insert the distal end 18 too deeply into the ear canal. That is, the shape and geometry of the distal end 18 does not allow significantly introducing the distal end point 34 into the patient's inner part of the outer ear canal which is pain sensitive. Therefore, injuries to the skin of the inner part of the outer ear canal and/or the eardrum can be reliably avoided. The geometry and the technology of the inventive otoscope do not require deforming the patient's ear as with a classic otoscope, as described above. Consequently, the otoscope according to the present invention can also be securely applied by laypersons.

Even though the distal end 18 of the head portion 14 will not be inserted into the inner part of the outer ear canal, the otoscope according to the present invention, nevertheless, allows for capturing images from the inner part of the outer ear canal and the eardrum, because of the electronic imaging unit 40 comprising a wide angle camera being provided at the distal end 18 of the head portion 14. In order to improve the ability of the electronic imaging unit 40 to "see" the eardrum, the camera of the electronic imaging unit 40 is placed offset from the longitudinal axis A of the head portion 14. Furthermore, the main "viewing direction" of the camera of the electronic imaging unit 40, corresponding to the bore axis B, is angled or tilted with respect to the longitudinal axis A of the head portion 14. The bore axis B and the longitudinal axis A intersect at a point having a predetermined distance from the distal end point 34, wherein the predetermined distance corresponds to the typical length of a patient's inner part of the outer ear canal, so that the camera of the electronic imaging unit 40 is directed to the eardrum.

When the distal end 18 of the head portion is introduced in the patient's ear canal, it may happen that artifacts, such as earwax particles or hair, in front of the electronic imaging unit 40, e.g. adhering to the probe cover, partially or even fully obstruct the view onto to eardrum. Therefore, the motion mechanism 24 may turn the rotatable portion 20 of the head portion 14 with respect to the remaining otoscope 10 about its axis of rotation R. For example, the motion mechanism 24 may rotate the rotatable portion 20 from an initial position by about 120° in clockwise direction, then from the initial position by about 120 in counter-clockwise direction, and finally return to the initial position. The camera 40.1 may capture one or more images from each of these equally spaced three positions. The logic unit 44 may identify different objects in the patient's ear by comparing the images received from the camera 40.1. In particular, the logic unit 44 may discriminate artifacts from the eardrum by determining their distance to the camera 40.1 according to the principle of stereoscopic viewing, as described in more detail above.

In order to further improve the identification process more than one image may preferably be taken from each of the three positions of the camera 40.1, with different LEDs 46 switched on and off for each captured image. Illumination of the artifacts and the eardrum from different positions also assists to discriminate these objects, as described in more detail above.

Finally, a new image may be generated (preferably by the logic unit 44) in which the identified artifacts are eliminated, so as to clearly show the eardrum. The degree of reddishness of the eardrum can then be easily determined. The user may be provided with corresponding information, such as to see the physician because of the risk of otitis media, or not. Also if the otoscope failed to detect the eardrum because of massive earwax in the patient's ear canal, corresponding information may be provided to the user. The user may then decide to visit a physician for having his or her ear canal cleaned.

Figure 5:
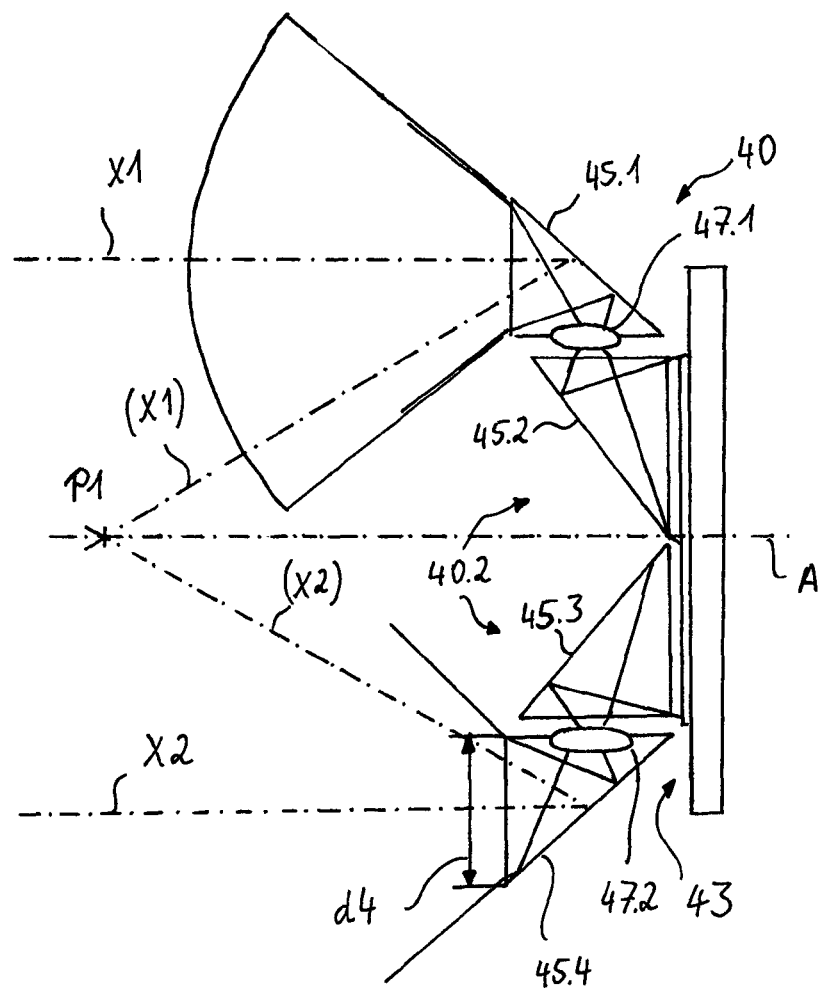
FIG. 5 schematically shows a cross-sectional side view of an electronic imaging unit according to one embodiment of an otoscope according to the present invention.

FIG. 5 shows an electronic imaging unit 40 exhibiting beam splitter optics 40.2 with at least two optical axes X1, X2 which are arranged radially offset with respect to a longitudinal axis A of a head portion (not shown) in which the electronic imaging unit 40 can be arranged. FIG. 5 shows an arrangement of an image sensor 43 with respect to several mirrors or prisms 45.1, 45.2, 45.3, 45.4 and lenses 47.1, 47.2. The image sensor 43 is, e.g., a VGA standard CMOS (dimension e.g. ⅛", i.e. 2.82 mm, or ⅒", i.e. 2.54 mm, and resolution e.g. 640×480) which is divided in several quadrants, e.g. four quadrants. Each of the quadrants can be partitioned off, e.g. by any opaque wall (not shown) or by appropriate equivalent aperture properties of the optics. In other words, each of the quadrants can be surrounded at least partially by a protruding wall or separator. Optical separators may ensure that light reflected on one of the quadrants is not reflected or scattered on one of the adjacent quadrants. According to a preferred embodiment, two of the mirrors 45.1, 45.2, 45.3, 45.4 are provided in the form of reflective coatings on molded prisms (e.g. PMMA prisms). The lenses 47.1, 47.2 can be part of the prisms, or can be provided separately, respectively. The molded prisms and the lens can provide an electronic imaging unit 40 with beam splitter optics 40.2. The schematic FIG. 5 shows a 2-in1-optic. Nonetheless, also a 3-in-1-optic or a 4-in-1-optic can be realized, wherein four of the lenses 47.1, 47.2 are provided, respectively in conjunction with two respective prisms. The arrangement shown in FIG. 5 can be described as a multi lens single sensor arrangement. In other words: Beam splitter optics 40.2 provide an alternative to a multi camera arrangement. The present invention is based on the finding that either four individual miniature cameras or a 4-in-1-optic with a single (relatively larger) image sensor chip is most favorable. Nonetheless, these two concepts may be combined, i.e. beam splitter optics 40.2 can be combined with one or more cameras.

For reasons of lucidity, the optical axes X1, X2 are shown in an orientation which is at least approximately parallel to the longitudinal axis A of the head portion (not shown). Nonetheless, the optical axes X1, X2 can be tilted against the longitudinal axis A, especially by a tilt angle in the range of 10° to 60°, preferably 15° to 40°, further preferred 20° to 30°, so as to be directed to a predetermined point P1 on the longitudinal axis A, as indicated by the broken lines intersecting the longitudinal axis A in point P1. Preferably, the tilt angle is variable.

The mirror or prism 45.1, 45.4 exhibits a radial dimension or diameter d4 which is relatively small, especially smaller than 1 mm, preferably smaller than 0.9 mm, even smaller than 0.8 mm or 0.7 mm, such that a relatively large radial offset of each optical axis can be realized.

Figure 6:
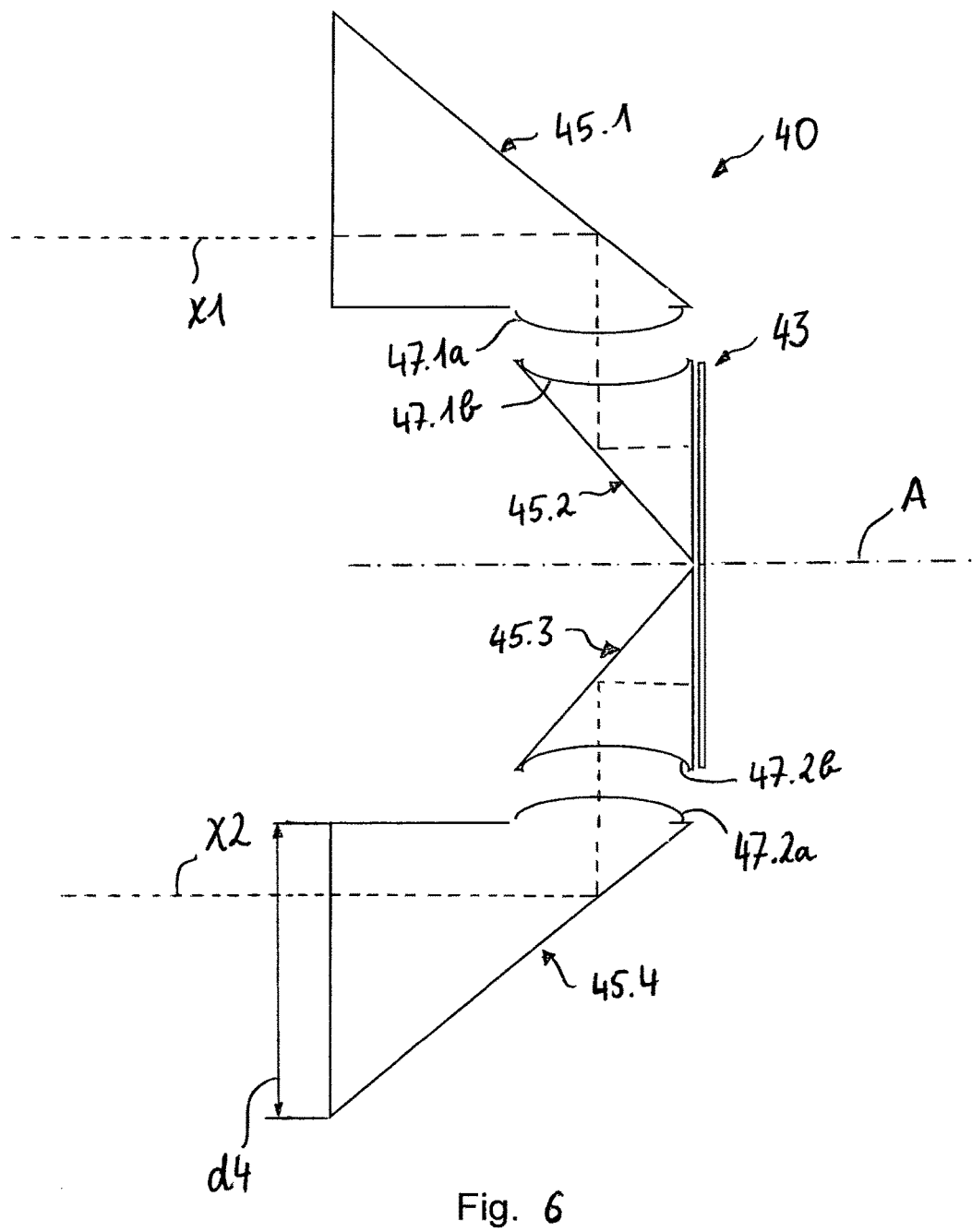
FIG. 6 schematically shows a cross-sectional side view of a further electronic imaging unit according to one embodiment of an otoscope according to the present invention.

FIG. 6 shows an electronic imaging unit 40 exhibiting beam splitter optics 40.2 with at least two optical axes X1, X2 which are arranged radially offset with respect to a longitudinal axis A of a head portion (not shown) in which the electronic imaging unit 40 can be arranged. FIG. 6 shows an arrangement of an image sensor 43 with respect to several mirrors or prisms (e.g. PMMA prisms) 45.1, 45.2, 45.3, 45.4 and lenses 47.1a, 47.1b, 47.22, 47.2b. The image sensor 43 is, e.g., a VGA standard CMOS (dimension e.g. ⅛", i.e. 2.82 mm, or ⅒", i.e. 2.54 mm, and resolution e.g. 640×480) which is divided in several quadrants, e.g. four quadrants. The prisms 45.1, 45.2, 45.3, 45.4 include the lenses 47.1a, 47.1b, 47.2a, 47.2b. The prism 45.2, 45.3 includes a concave lens 47.1b, 47.2b, respectively. The prism 45.1, 45.4 includes a convex lens 47.1a, 47.2a, respectively. As mentioned in context with FIG. 5, the beam splitter optics 40.2 can provide e.g. a 3-in-1-optic or a 4-in-1-optic.

The mirror or prism 45.1, 45.4 exhibits a radial dimension or diameter d4 which is relatively small, as describes in conjunction with FIG. 5.

Figure 7:
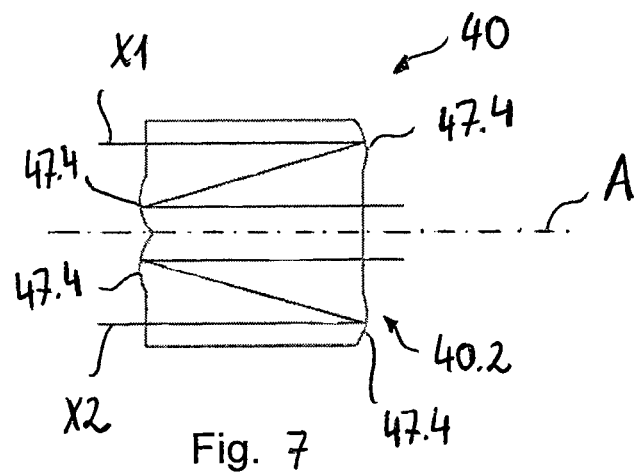
FIG. 7 schematically shows a cross-sectional side view of beam splitter optics for an electronic imaging unit according to one embodiment of an otoscope according to the present invention.

FIG. 7 shows an electronic imaging unit 40 which exhibits beam splitter optics 40.2 in the form of a mirror arrangement including two concave mirrors 47.4 for a respective optical path. Two optical axes X1, X2 are radially offset with respect to a longitudinal axis A of a head portion (not shown). Preferably, the two concave mirrors 47.4 are provided in the form of aspherical surfaces and are tilted against the respective optical axis X1, X2 or the longitudinal axis A. The beam splitter optics 40.2 shown in FIG. 7 only feature two concave mirrors 47.4 for each optical path. Thus, a simple, straightforward arrangement can be realized, especially a low-cost arrangement using a single or a few molded optical parts or components. The reflective surfaces or mirrors can be realized e.g. by depositing a metal coating on an optically transparent surface.

The respective concave mirror 47.4 exhibits a radial dimension or diameter d4 which is relatively small, especially smaller than 1 mm, preferably smaller than 0.9 mm, even smaller than 0.8 mm or 0.7 mm, such that a relatively large radial offset of each optical axis X1, X2 can be realized.

Figure 8:
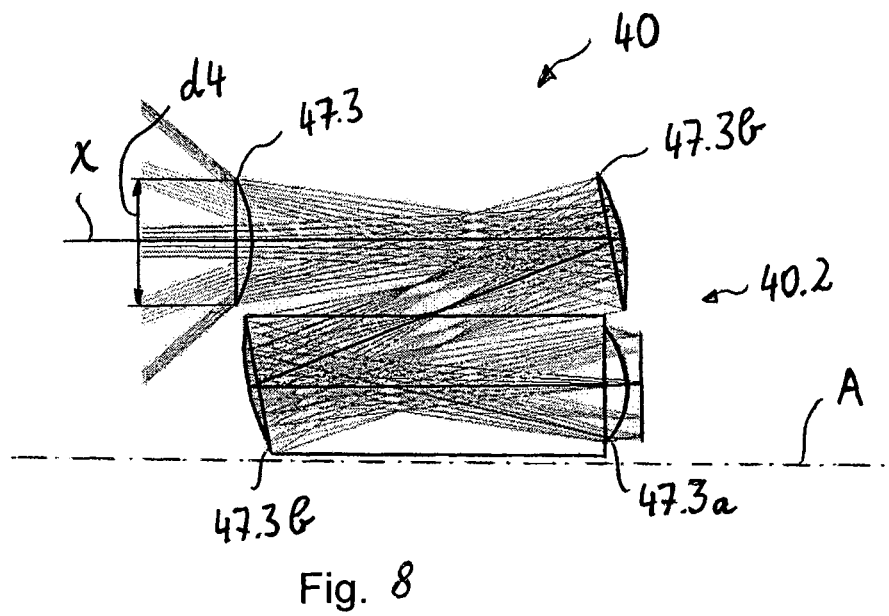
FIG. 8 schematically shows a cross-sectional side view of further beam splitter optics for an electronic imaging unit according to one embodiment of an otoscope according to the present invention.

FIG. 8 shows an electronic imaging unit 40 exhibiting beam splitter optics 40.2 in the form of a plurality of refractive lenses 47.3, 47.3a, 47.3b, the beam splitter optics 40.2 including two refractive and reflective surfaces 47.3b (especially aspherical mirrors) as well as one concave refractive surface 47.3 and one convex refractive surface 47.3a for a respective optical path. An optical axis X is radially offset with respect to a longitudinal axis A of a head portion (not shown).

A respective lens, especially the concave refractive lens 47.3 which is arranged radially outwards, exhibits a radial dimension or diameter d4 which is relatively small, especially smaller than 1 mm, preferably smaller than 0.9 mm, even smaller than 0.8 mm or 0.7 mm, such that a relatively large radial offset of the optical axis X can be realized.

FIGS. 7 and 8 may refer to the same embodiment, depending on the kind of optical components which do not exhibit any mirror or reflecting surface.

Figure 9:
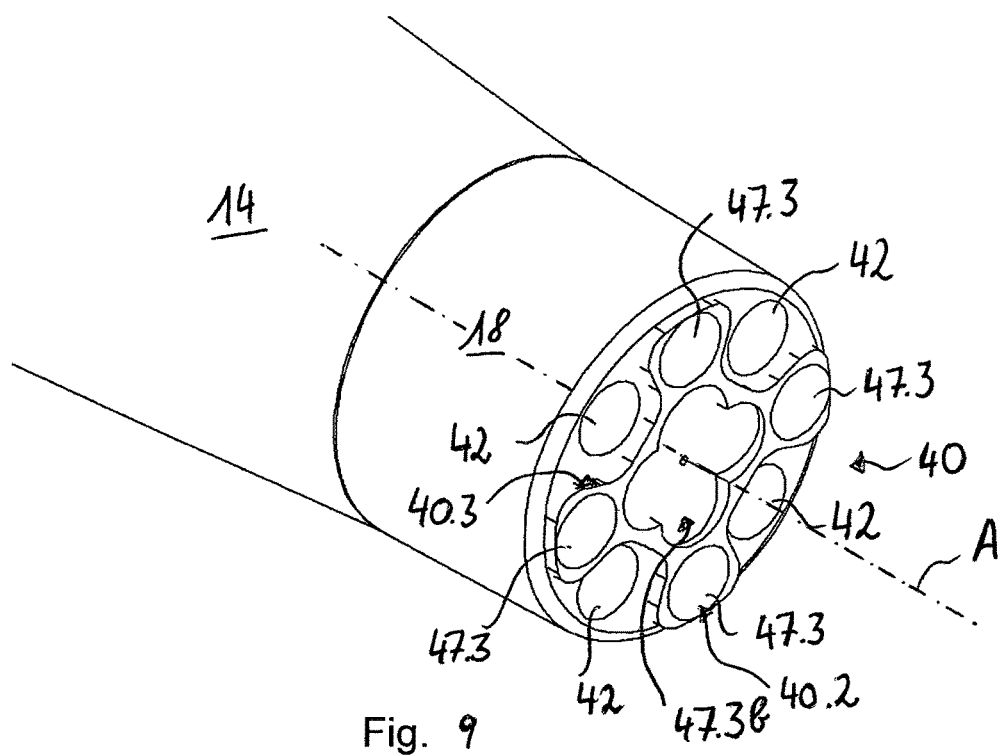
FIG. 9 schematically shows a perspective side view of a head portion with an electronic imaging unit which is arranged for accommodating the beam splitter optics shown in FIG. 8.

FIG. 9 shows a head portion 14 with a distal end 18 in which an electronic imaging unit 40 is positioned. The electronic imaging unit 40 comprises the beam splitter optics 40.2 shown in FIG. 8. The electronic imaging unit 40 comprises sixteen (16) refractive and/or reflective surfaces, wherein four outer lenses 47.3 are arranged adjacent to an inner lateral surface of the distal end 18, i.e. with a maximum radial offset. Four further reflective surfaces 47.3b are arranged concentrically around a longitudinal axis A of the head portion 14, the radial offset being smaller. For each of four different light paths, two further surfaces (namely aspherical mirrors; not shown) are arranged behind (proximal to) the distal end 18. The electronic imaging unit 40 comprises a housing or support 40.3 for accommodating the lenses. In particular, the support 40.3 can be provided in the form of an injection-molded part, especially a single part, or one part for each light path. The support 40.3 can be made of e.g. PMMA (polymethyl methacrylate). The support 40.3 is arranged for accommodating four light guides 42 or light sources and at least four lenses or lens surfaces, preferably sixteen refractive and/or reflective surfaces, wherein four lenses are provided for each of the four light paths, respectively. The support 40.3 is arranged for accommodating, for each of the lenses 47.3 with the largest radial offset, two light guides 42 adjacent to each of the lenses 47.3 with the largest radial offset. The support 40.3 is arranged for accommodating the light guides 42 on the same pitch circle as the lenses 47.3 with the largest radial offset.

Figure 10:
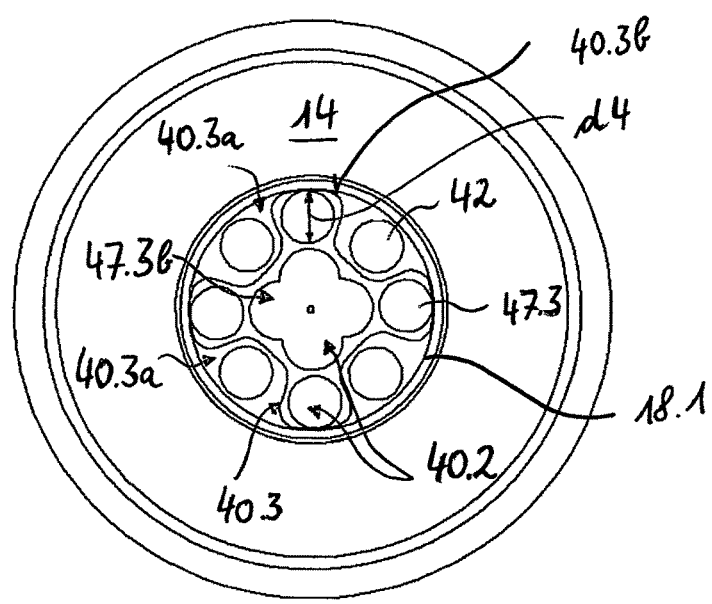
FIG. 10 schematically shows a top view of the head portion shown in FIG. 9.

In order to provide optical components, especially reflective surfaces, in conjunction with the support 43, specific surfaces of the support 40.3 can be coated, especially metal-coated, e.g. by vapour deposition or sputtering technique. The support 40.3 exhibits four recesses 40.3a for accommodating a plurality of light guides 42. FIG. 10 shows the support 40.3 from a front side. It can be seen that the light guides 42 are arranged on the same pitch circle as the lenses 47.3 with the largest radial offset adjacent to the lenses 47.3. The light guides 42 can be fixed at the outer lateral surface of the support 40.3, and/or at the inner lateral surface 18.1, e.g. by an adhesive bond, or by pressing into an appropriate contour or form. The support 40.3 exhibits a convex outer lateral surface 40.3b, at least in sections. This convex surface 40.3b can ensure that the electronic imaging unit 40 can be positioned as close as possible adjacent to a (cylindrical) inner lateral surface 18.1 of the distal end 18 or distal tip, in order to provide a maximum radial offset with respect to the diameter of the distal end or tip.

According to a further embodiment (not shown), the lens surfaces 40.3 and the mirrors 47.3b could be shaped not as a circular, but a semicircular form. A semicircular form allows for further increase of the radial offset of the respective optical axis.

The lenses 47.3 exhibit a radial dimension or diameter d4 which is relatively small, especially smaller than 1 mm, preferably smaller than 0.9 mm, even smaller than 0.8 mm or 0.7 mm, such that a relatively large radial offset of the optical axes can be realized.

Figure 11:
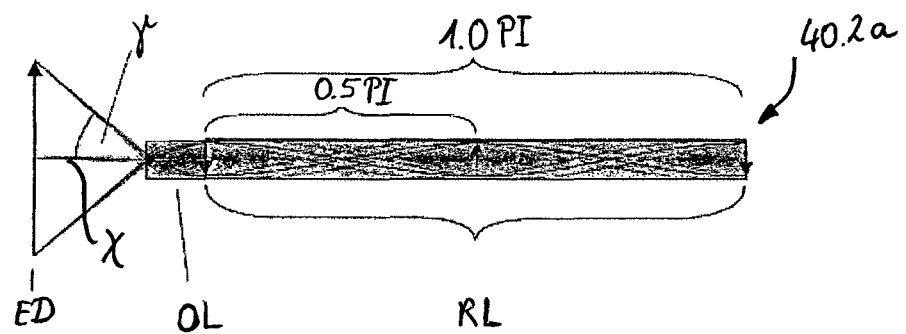
FIG. 11 schematically shows a specific fibre which can be used as a component of beam splitter optics for an electronic imaging unit according to a further embodiment of an otoscope according to the present invention.

FIG. 11 shows an optical fibre 40.2a which can be used as a component of beam splitter optics providing a plurality of optical axes. The optical fibre can be provided in the form of so called gradient index (GRIN) fibre. Such a GRIN fibre can be characterized by having a relay lens RL with a specific pitch PI and an objective lens OL, the objective lens OL being arranged at a distal end of the fibre 40.2a. The relay lens RL has a length corresponding to the length of the pitch, i.e. a length of 1.0PI. An object ED, e.g. an eardrum, is observed, and the light or radiation emitted by the object ED is reflected within the fibre 40.2a. In particular, the radiation is reflected at an inner wall of the fibre 40.2a at a linear section of 0.5PI. The GRIN fibre can be conceived as an optical lens or a plurality of lenses. Such a GRIN fibre can ensure a wide angle of vision γ. The angle of vision γ corresponds to an angle between an optical axis X and an outer border of the field of vision of the fibre. The angle of vision γ preferably is in a range between 30° and 60°, more preferably between 45° and 60°, such that a field of vision with a wide angle (90° to 110° or 120°) can be ensured.

Figure 12:
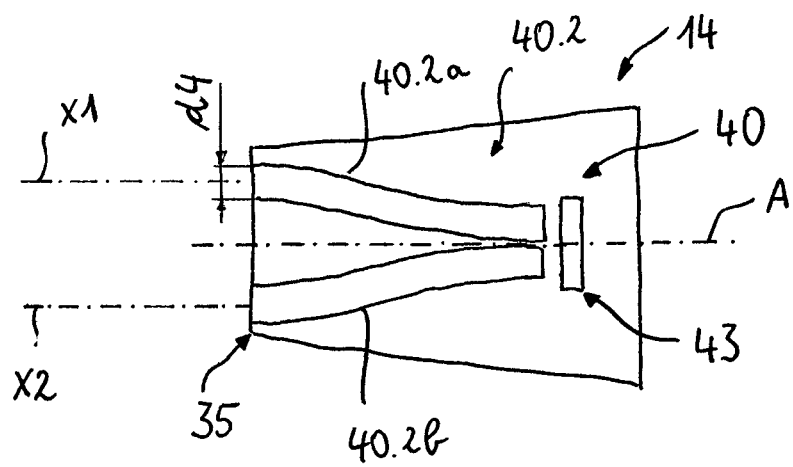
FIG. 12 schematically shows beam splitter optics including several fibres as shown in FIG. 11.

FIG. 12 shows a head portion 14 accommodating an electronic imaging unit 40 which comprises beam splitter optics 40.2 and an image sensor 43. The beam splitter optics 40.2 comprise several GRIN fibres 40.2a, 40.2b which are arranged between a distal tip 35 of the head portion 14 and the image sensor 43. Each fibres 40.2a, 40.2b is in visual communication with a specific quadrant or surface section of the image sensor 43. The image sensor 43 is arranged concentrically with respect to a longitudinal axis A of the head portion 14. The beam splitter optics 40.2 provide several optical axes X1, X2.

The GRIN fibres 40.2a, 40.2b exhibit a diameter d4 which is relatively small, especially smaller than 1 mm, preferably smaller than 0.9 mm, even smaller than 0.8 mm or 0.7 mm, such that a relatively large radial offset of the optical axes can be realized. In particular, the diameter d4 may be considerably smaller than the radial dimensions of a miniature camera.

FIGS. 11, 12, 13, 14, 15 and 18 show embodiments of the electronic imaging unit 40 which can be accommodated within a head portion 14 as shown in FIG. 1, respectively. A respective image sensor 43 of the imaging unit 40 can be provided with relatively large radial dimensions, especially as the image sensor 43 can be arranged separate from the distal tip, i.e. more proximal than the distal tip. At such a position, the head portion 14 usually exhibits a larger diameter, providing more space in the lateral (radial) direction.

Figure 13:
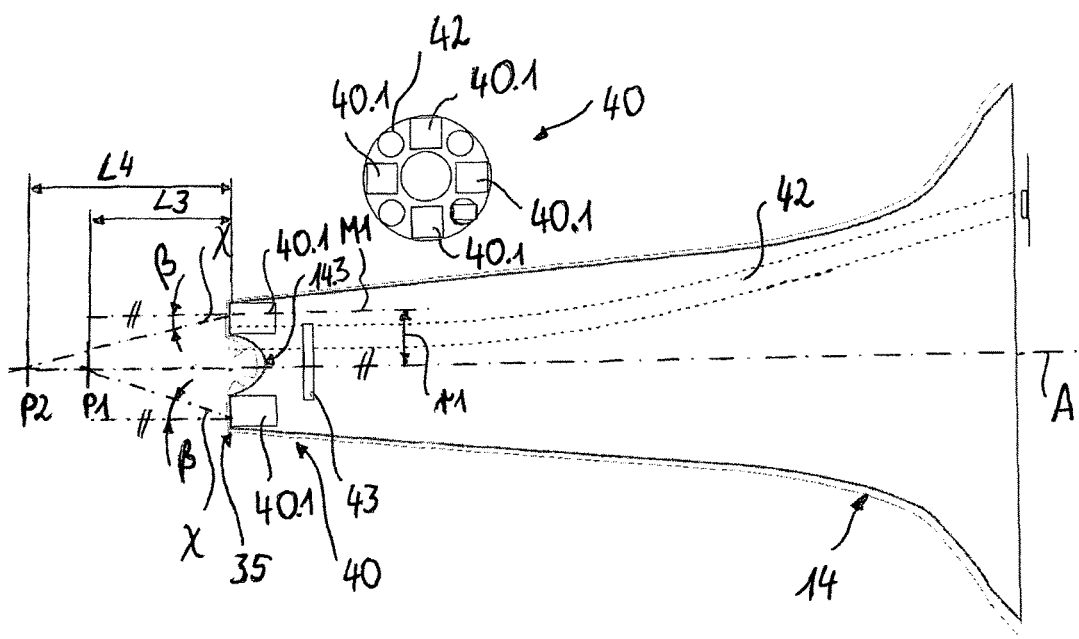
FIG. 13 schematically shows a cross-sectional side view of the head portion of an embodiment of an otoscope according to the present invention as well as a front view on the distal end of the head portion.

FIG. 13 shows a head portion 14 accommodating several light guides or light sources 42 and an electronic imaging unit 40 comprising several eccentrically arranged, i.e. radially offset cameras 40.1. The electronic imaging unit 40 is positioned substantially centrically with respect to the longitudinal axis A of the head portion 14. Light is guided from one or more light sources via the light guides 42 to the distal tip 35. Optionally, more than four light guides may be provided. In particular, for each camera 40.1, two light guides or light sources 42 can be provided.

The cameras 40.1 are arranged in a radial distance r1 to the longitudinal axis A, the distance r1 being measured between the longitudinal axis A and a middle axis M1 of the respective camera 40.1. The (eccentric) distance r1, i.e. the radial offset is in the range of 1 mm to 2.8 mm or 1.3 mm to 2.5 mm, preferably 1.7 mm to 2.2 mm, especially about 1.8 mm, 1.9 mm or 2.0 mm. The ratio r1:d1 is preferably in the range of 0.35 to 0.55, especially 0.4, 0.45 or 0.5.

An optical axis X of at least two of the cameras 40.1 is arranged at an angle β with respect to the longitudinal axis A, allowing the cameras 40.1 to "look around the corner". The angle β preferably is in the range of 10° to 30°.

A distance L3 or L4 between the distal tip 35 or a distal end point of the head portion 14 and a predetermined point P1 or P2 on the longitudinal axis A is preferably in the range of 10 mm to 25 mm, especially 16 mm, 18 mm or 20 mm.

In addition to the cameras 40.1, the electronic imaging unit 40 can be provided with an image sensor 43, especially a CMOS devided in several quadrants, preferably four quadrants. Beam splitter optics (not shown) can be provided in conjunction with the image sensor 43, the beam splitter optics providing a plurality of optical axes, preferably a number of optical axes corresponding to the number of quadrants.

Preferably, either the concept of several cameras each provided with an image sensor or chip or the concept of beam splitter optics in conjunction with one single image sensor may be realized. Nonetheless, a combination of these concept may be realized, as suggested by the image sensor 43.

Preferably, the electronic imaging unit 40 is provided with a plurality of optical axes (not shown) which are arranged radially offset with respect to a longitudinal axis A of the head portion 14. The optical axes can be tilted against the longitudinal axis A.

The image sensor 43 can provide the advantage that the number of cameras 40.1 can be reduced, or that at least one of the cameras 40.1 can be replaced by an optical system, e.g. comprising one or more lenses and/or mirrors and/or prisms. Preferably, the number of quadrants of the image sensor 43 corresponds to the number of optical axes provided independently from or in addition to the cameras 40.1.

In the embodiment shown in FIG. 13, the cameras 40.1 are arranged with a radial offset r1 such that the head portion 14 can be provided with a groove or indentation 14.3 which can be arranged concentrically with respect to the longitudinal axis A. In particular, the indentation 14.3 can provide a cavity for accommodating a portion of a probe cover.

As an alternative to the embodiment shown in FIG. 13, the electronic imaging unit 40 can comprise one single camera which is positioned substantially centrically with respect to the longitudinal axis A of the head portion 14, the optical axis of the camera being tilted.

Figure 14:
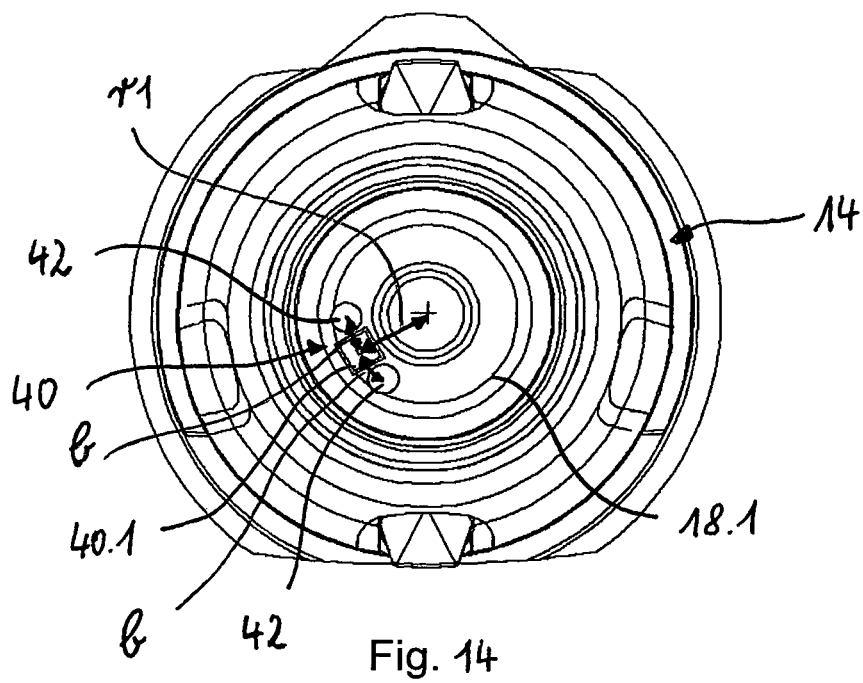
FIG. 14 schematically shows a top view of a head portion accommodating an electronic imaging unit comprising a camera, according to one embodiment of an otoscope according to the present invention.

FIG. 14 shows a head portion 14 accommodating an electronic imaging unit 40 which comprises one single camera 40.1. The camera 40.1 is positioned radially offset with a maximum radial offset r1. The camera 40.1 is positioned adjacent to a cylindrical inner lateral surface 18.1 of a distal tip of the head portion 14. Two light guides or light sources 42 are arranged adjacent to the camera 40.1, especially on the same pitch circle as the camera 40.1. Preferably, the camera 40.1 can be rotated by a motion mechanism (not shown), especially together with the light guides 42 or at least the distal ends of the light guides 42. The light guides 42 can be made of a flexible material, such as nylon, and the light guides 42 can be twisted or bent in case a proximal end of the light guides 42 is not rotated. As an alternative, light sources (not shown) can be rotated together with the camera 40.1 and the light guides 42, also. The diameter of the light guides 42 is in a range between 0.2 and 1.5 mm, preferably 0.7 mm and 1.2 mm, especially 1.0 mm.

The camera 40.1 is arranged in a radial distance r1 to the longitudinal axis A, the distance r1 being measured between the longitudinal axis A and a middle axis of the camera 40.1. The (eccentric) radial distance r1 is in the range of 1.8 mm to 2 mm. The two light guides 42 are arranged adjacent to the camera 40.1 in a distance b which corresponds to the length of (a part of) a circular arc of the pitch circle on which the camera 40.1 and the two light guides 42 are arranged. The distance b is measured between a middle axis of the camera 40.1 and a middle axis of the respective light guide 42. Preferably, the distance b is in the range of 0.5 mm to 2 mm, more preferable 0.8 mm to 1.8 mm, especially 1.5 mm.

In the embodiments shown in FIGS. 13 and 14, the (respective) camera is arranged with a radial offset which can be defined such that an infrared sensor (not shown) can be positioned on the longitudinal axis A or concentrically with the longitudinal axis A.

Figure 15:
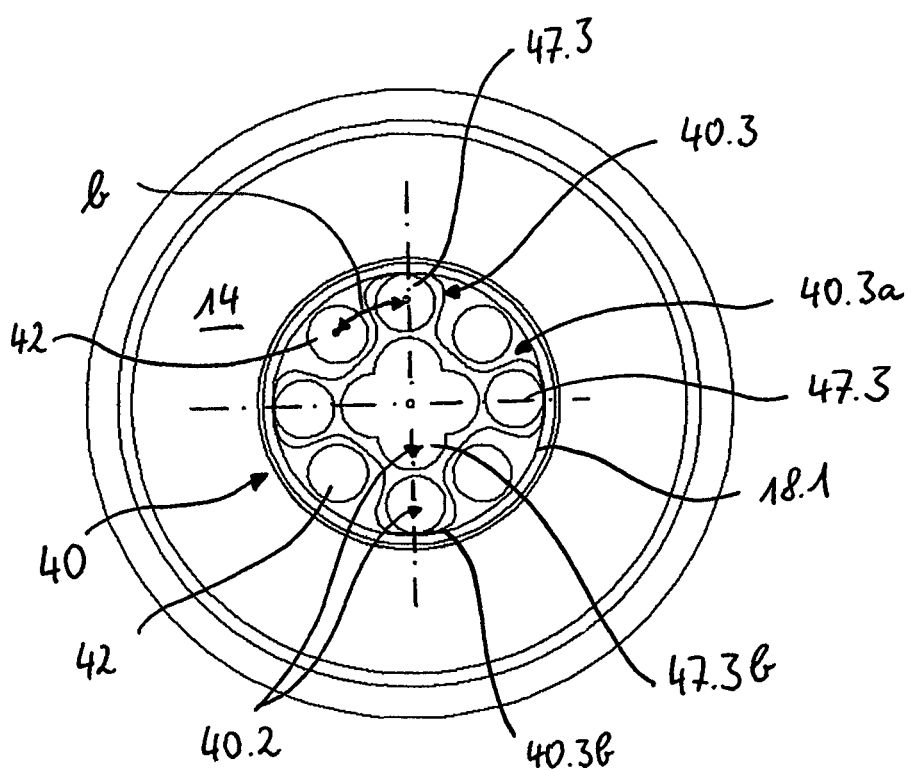
FIG. 15 schematically shows a top view of a head portion accommodating an electronic imaging unit with beam splitter optics comprising four optical axes, according to one embodiment of an otoscope according to the present invention.

FIG. 15 shows a head portion 14 with a distal end having a cylindrical inner lateral surface 18.1. An electronic imaging unit 40 is positioned at the distal end within the inner lateral surface 18.1. The electronic imaging unit 40 comprises a support 40.3 for accommodating beam splitter optics 40.2. The beam splitter optics 40.2 comprise a plurality of lenses 47.3 (especially eight lenses) and reflective surfaces 47.3b (especially eight reflective surfaces), some of which are shown in FIG. 15. In FIG. 15, four lenses are shown. The beam splitter optics 40.2 provide four different optical paths. Each optical path is defined by two lenses and two reflective surfaces. Those lenses which define an optical path are arranged in the same plane, respectively, as indicated by the dot-dash lines.

Four light guides or light sources 42 are arranged between the lenses 47.3, respectively. Preferably, the light guides 42 are made of PMMA which provides good optical characteristics. The light guides 42 are arranged adjacent to the lenses 47.3 (with the largest radial offset) and in a distance b to each lens 47.3 which corresponds to the length of a circular arc of a pitch circle on which the lenses 47.3 and the light guides 42 are arranged. The distance b is measured between a middle axis of the respective to the lens 47.3 and a middle axis of the respective light guide 42. Preferably, the distance b is in the range of 0.8 mm to 1.6 mm, more preferable 0.9 mm to 1.5 mm, further preferable close to 1.3 mm, especially between 1 mm and 1.3 mm, depending on the diameter of the light guides 42.

An outer lateral surface of the support 40.3 is arranged adjacent to the inner lateral surface 18.1. The outer lateral surface of the support 40.3 touches the inner lateral surface 18.1. The support 40.3 exhibits a convex outer lateral surface 40.3b, at least in sections. This convex surface 40.3b can ensure that the electronic imaging unit 40 can be positioned as close as possible adjacent to a (cylindrical) inner lateral surface of the distal end or distal tip of the head portion 14, in order to provide a maximum radial offset with respect to the diameter of the distal end or tip. With such an arrangement, the four lenses 47.3 shown in FIG. 15 can be positioned with a maximum radial offset and with a maximum distance from each other.

In the embodiments shown in FIGS. 13 and 15, a respective image sensor of the imaging unit 40 can be provided with relatively large radial dimensions, especially as the image sensor 43 can be arranged separate from the distal tip, i.e. more proximal than the distal tip. At such a position, the head portion 14 usually exhibits a larger diameter, providing more space in the lateral (radial) direction.

Figure 16:
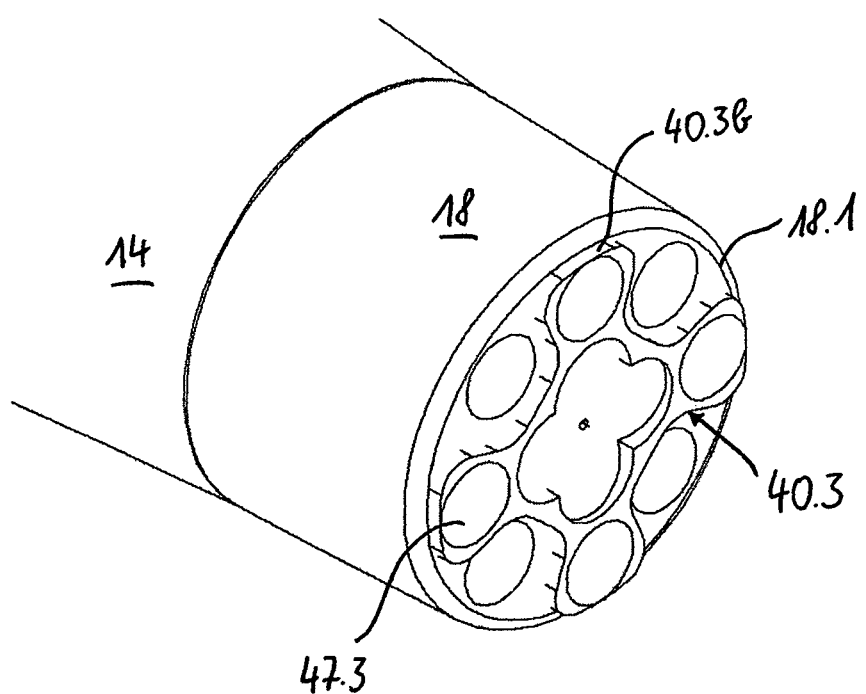
FIG. 16 schematically shows a perspective side view of the head portion shown in FIG. 15.

FIG. 16 shows the support 40.3 being arranged at the inner lateral surface 18.1 of the distal end 18. The distal end 18 exhibits a cavity for accommodating the support 40.3. The cavity is arranged adjacent to the inner lateral surface 18.1. The cavity is confined by the inner lateral surface 18.1. The four lenses 47.3 being positioned with the maximum radial offset are arranged adjacent to the inner lateral surface 18.1, too. In other words: At a lateral section of the respective lens 47.3 facing radially outwards, the support 40.3 has reduced a wall thickness, in order to enable a maximum radial offset of the lenses 47.3. Preferably, at the portions of the support 40.3 arranged most outwardly (i.e., the portions with the largest radial extension), the wall has a thickness which converges to zero, such that the respective lens 47.3 is arranged directly adjacent to the inner lateral surface 18.1 or touches the inner lateral surface 18.1.

Figure 17A:
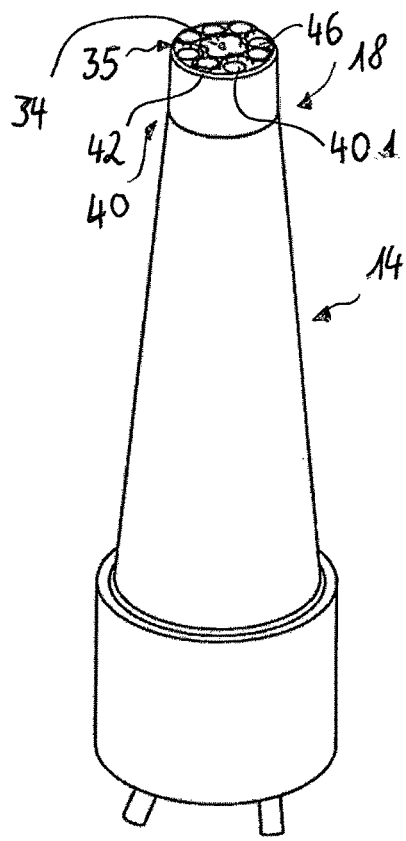
FIG. 17A schematically shows a perspective side view of a head portion of an embodiment of an otoscope according to the present invention.
Figure 17B:
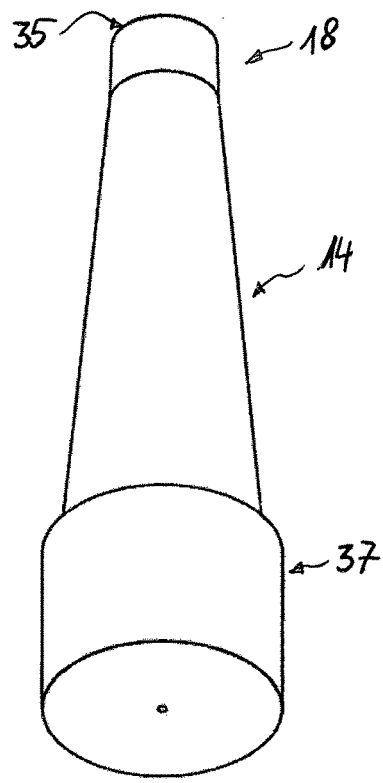
FIG. 17B schematically shows another perspective side view of the head portion shown in FIG. 17A.

In FIG. 17A, a head portion 14 with a distal end 18 is shown. At a distal tip 35 of the head portion 14, an electronic imaging unit 40 is arranged which includes a plurality of cameras 40.1 arranged eccentrically, i.e. positioned radially offset. Further, a plurality of light sources 46 or light guides 42 are positioned radially offset. At a distal tip 35, a distal end point 34 is arranged, which is the most distal point of the head portion 14. In FIG. 17B, a proximal portion 37 of the head portion 14 is shown from the bottom side which can be coupled with or connected to a handle portion (not shown).

Figure 17C:
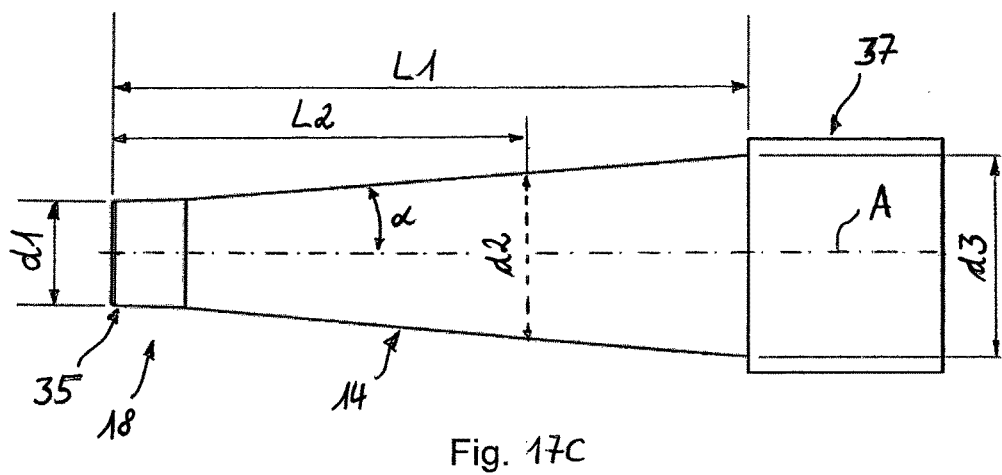
FIG. 17C schematically shows a side view of the head portion shown in FIG. 17A.

In FIG. 17C, the shape of the head portion 14 is described in detail. The distal tip 35 of the head portion 14 has a diameter d1. Along a length L1, in the proximal direction, the diameter of the head portion 14 gets wider, i.e. becomes bigger. The distal end 18 can be provided with a cylindrical or conical shape. As shown, the shape between the distal end 18 and the proximal portion 37 can be strictly conical. But, the shape can also be conical only in one or more sections, and can be e.g. parabolic in one or more further sections. Preferably, a parabolic section is provided at a proximal section of the head portion 14, in order to provide a kind of collar or transition area leading to a handle portion. At an intersection between the widening portion (the conical portion) and the proximal portion 37, the head portion 14 has a diameter d3. In a central section of the widening portion, the head portion 14 has a diameter d2, especially at an axial position defined by a specific length L2 which is preferably in the range of 28 mm to 32 mm, especially 20 mm.

The length L1 (which corresponds to a distance from the distal tip to the proximal portion) is preferably in the range of 25 mm to 30 mm, especially 28 mm. The diameter d1 of the distal tip 35 is preferably in the range of 4.5 mm to 5.1 mm, more preferable 4.6 mm to 4.8 mm, especially 4.7 mm. The diameter d3 is preferably in the range of 8 mm to 10 mm, especially 9 mm. The ratio of d1:d3 is preferably in the range of 0.5.

The ratio of d1:d2 is preferably in the range of 0.57 to 0.65, especially about 0.58 or about 0.63. Such a ratio can ensure that the head portion can be introduced only as deep as not to touch the hard bone, or at most only as far as some millimeters within the section confined by hard bone. In particular, such a ratio can ensure that the head portion can be introduced only in the area of the soft connective tissue confining the outer ear canal, but not in the area of the hard bone.

Figure 18:
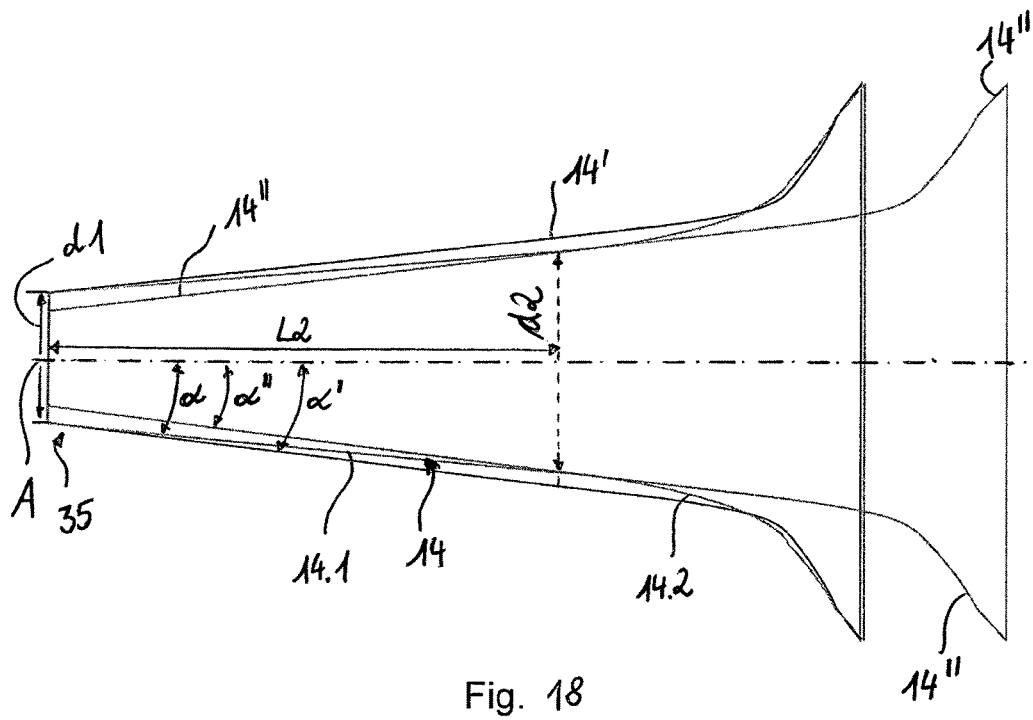
FIG. 18 schematically shows a side view of the head portion of an embodiment of an otoscope according to the present invention in comparison with two head portions of an otoscope of the prior art.

In FIG. 18, the shape of a head portion 14 according to one embodiment of the present invention is shown in comparison with the shape of a first head portion 14' according to prior art and a second head portion 14" according to prior art. It can be seen that the head portion 14 has a conical section 14.1 and a parabolic section 14.2. The conical section 14.1 can also be described as an insertion section which is provided for getting in contact with soft connective tissue. At a transition area between the conical section 14.1 and the parabolic section 14.2, the head portion 14 has a diameter d2. The conical section 14.1 is provided along a specific length L2.

As compared with the first head portion 14', which is preferably provided for children older than 12 month or for adults, the shape of the head portion 14 is more slender, and an opening angle α of the conus of the conical section 14.1 is smaller, i.e. more obtuse. As compared with the second head portion 14", which is preferably provided for infants younger than 12 month, a distal tip 35 of the head portion 14 has a larger diameter d1. Also, the opening angle α of the head portion 14 is smaller, i.e. more obtuse. In other words: The opening angle α is more obtuse than the opening angle α' of the head portion 14' or than the opening angle α" of the head portion 14". The opening angle α is preferably in the range of 3° to 10°, further preferred 4° to 8°, especially 5° or 6°. The ratio d1:d2 of the inventive head portion 14 is bigger as compared with the conventional head portions 14' and 14".

A specific length L2 is preferably in the range of 18 mm to 22 mm, especially 20 mm. A diameter d1 of the distal tip 35 is preferably in the range of 4.7 mm to 5.2 mm, more preferably 4.8 mm to 5 mm, especially 4.9 mm. A diameter d2, especially at a distance of 20 mm from the distal tip 35, is preferably in the range of 8 mm to 9 mm, especially 8.5 mm.

Figure 19:
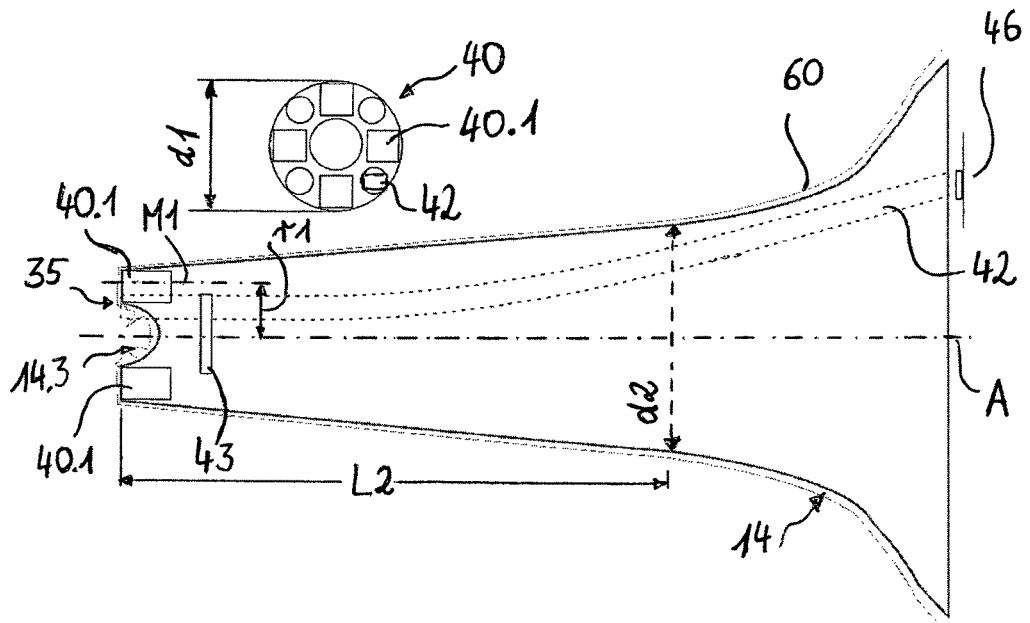
FIG. 19 schematically shows a cross-sectional side view of the head portion of an embodiment of an otoscope according to the present invention as well as a front view on the distal tip of the head portion.

FIG. 19 shows a head portion 14 including at least one light guide or light source 42 and an electronic imaging unit 40 comprising several eccentrically arranged, i.e. radially offset cameras 40.1. Light is guided from one or more light sources 46 via the light guide 42 to the distal tip 35. Along a specific length L2, the head portion 14 has a conical shape. The specific length L2 can be defined as the length along which the head portion 14 can be in contact with the patient's tissue, especially with soft connective tissue confining the outer ear canal, at least partially. The specific length L2 is preferably in the range of 18 mm to 22 mm, especially 20 mm. The diameter d1 of the distal tip 35 is preferably in the range of 4.7 mm to 5.2 mm, more preferably 4.8 mm to 5 mm, especially 4.9 mm. The diameter d2, especially at a distance of 20 mm from the distal tip 35, is preferably in the range of 8 mm to 9 mm, especially 8.5 mm. A probe cover 60 can be provided over the head portion 14. The total length of the head portion is in the range between 26 mm and 34 mm, preferably 28 mm and 32 mm, more preferable 29 mm and 31 mm, especially around 30.3 mm.

The cameras 40.1 are arranged in a radial distance r1 between the longitudinal axis A and a middle axis M1 of the respective camera 40.1. The (eccentric) distance r1, i.e. the radial offset is preferably in the range of 1 mm to 2.8 mm or 1.2 mm to 2.5 mm, more preferable in the range of 1.5 mm to 2 mm, especially about 1.7 mm, 1.8 mm or 1.9 mm. The ratio r1:d1 is preferably in the range of 0.35 to 0.55, especially 0.4, 0.45 or 0.5.

At a distal tip, the head portion 14 exhibits an indentation 14.3. The indentation 14.3 is arranged concentrically with respect to the longitudinal axis A. The indentation 14.3 can be provided with, e.g., a parabolic or cylindrical shape. The indentation 14.3 provides a cavity for accommodating parts of the probe cover 60, in particular a folded or compressed portion of the probe cover 60.

As described in conjunction with FIG. 13, in addition to the cameras 40.1 or in conjunction with the cameras 40.1, an image sensor 43 can be provided.

Figure 20:
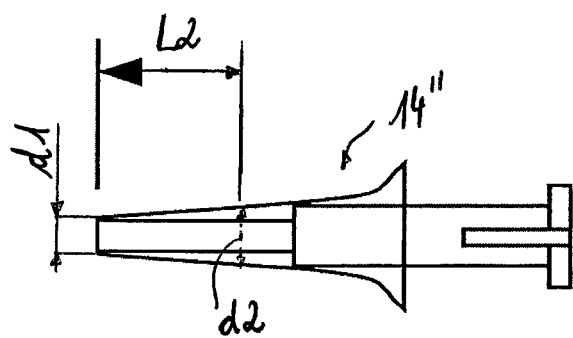
FIG. 20 schematically shows a cross-sectional side view of a head portion for infants of an otoscope of the prior art.
Figure 21:
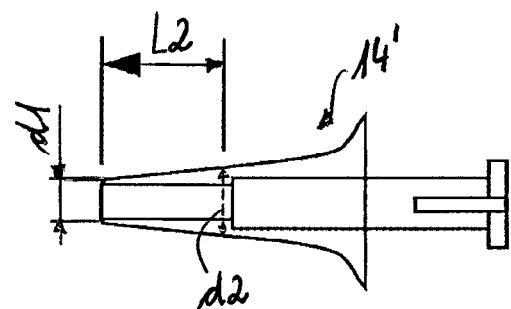
FIG. 21 schematically shows a cross-sectional side view of another head portion of otoscope of the prior art.

In FIGS. 20 and 21, the shape of head portions 14', 14" according to prior art is described schematically, referring to the specific length L2. In FIGS. 20 and 21, the specific length L2 is in the range of about 18 mm to 22 mm, especially 20 mm. In FIG. 20, the diameter d1 is in the range of 3.5 mm to 3.7 mm, especially 3.6 mm, and the diameter d2 (at a longitudinal position from the distal tip of about 20 mm) is about 8.5 mm. In FIG. 21, the diameter d1 is in the range of 4.8 mm to 5.2 mm, especially 5 mm, and the diameter d2 (at a longitudinal position from the distal tip of about 20 mm) is about 9.6 mm.

Figure 22:
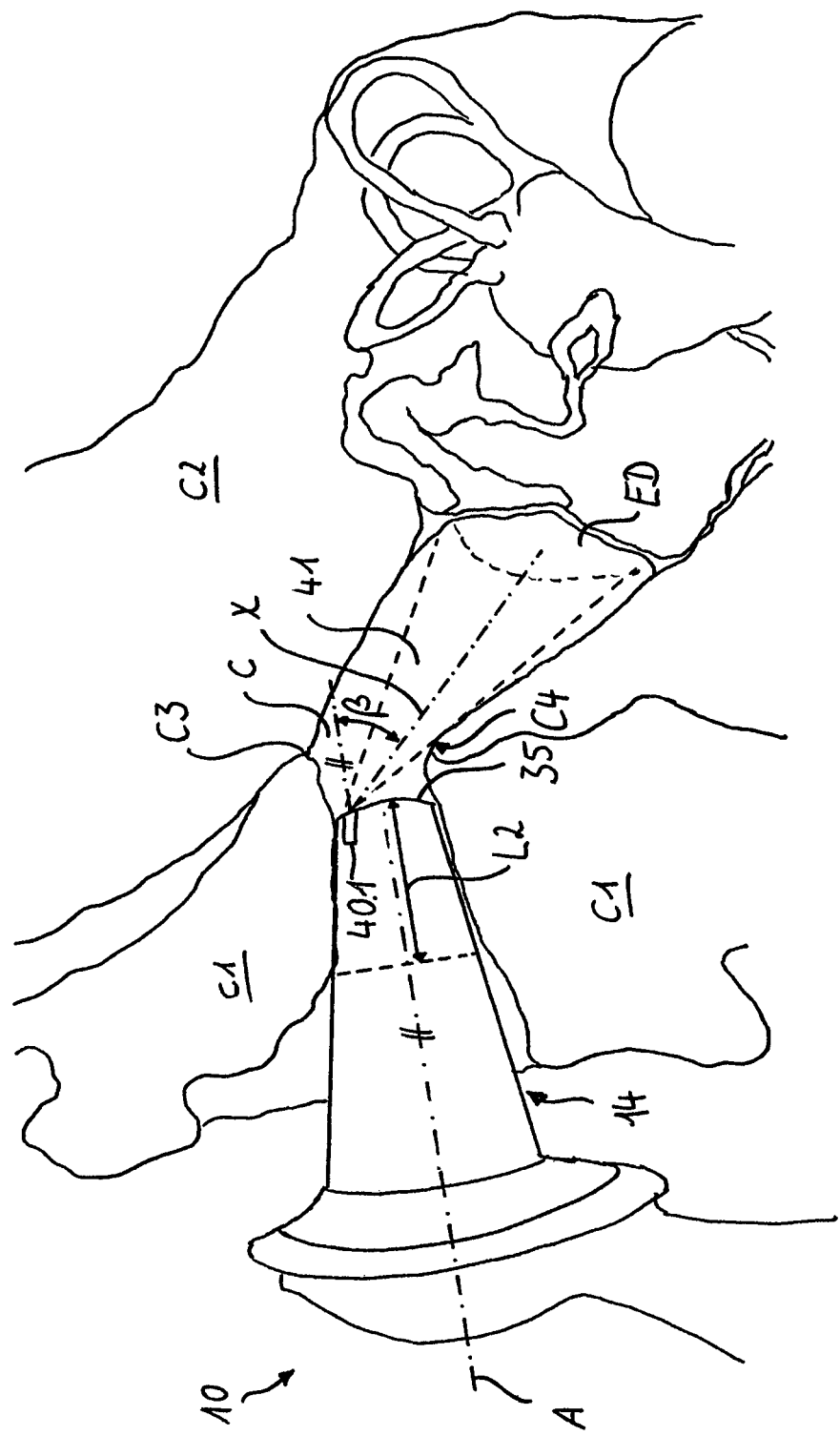
FIG. 22 schematically shows an otoscope according to the present invention, with its head portion introduced into the patient's ear canal.

In FIG. 22, an otoscope 10 with a head portion 14 including an electronic imaging unit comprising a camera 40.1 is shown, wherein the camera 40.1 is positioned eccentrically (i.e. radially offset) with respect to a longitudinal axis A of the head portion 14. The eccentricity (the radial offset) is, e.g., in the range of 1.5 mm to 2 mm. The head portion 14 is introduced in the ear canal C, and the outer surface of the head portion 14 or a probe cover (not shown) is in contact with the soft connective tissue C1. In contrast to the hard bone C2, the soft connective tissue C1 is elastic and can be widened by the head portion 14.

The camera 40.1 has a field of vision 41 which is preferably conical. Geometrically, the field of vision 41 can be describes as a conus with an opening angle in the range of at least 80°, preferably of at least 110°, e.g. 120°. The camera 40.1 preferably is a wide angle color video camera. An optical axis X of the camera 40.1 is arranged at an angle β with respect to the longitudinal axis, allowing the device to "look around the corner" effectively. The angle β preferably is in the range of 20° to 40°. The camera 40.1 is arranged to "look around the corner", in order to scan the eardrum ED. For this purpose, the camera 40.1 is arranged radially offset.

In FIG. 22, the anatomy of an ear canal C with a curvature C4 is shown. The curvature C4, which is typical for a large percentage of different shapes of the ear canal, forms a kind of "corner". As the camera 40.1 is arranged to "look around the corner", it is not required to introduce the distal tip 35 of the head portion 14 as far as a transition area or transition point C3 between soft connective tissue C1 and hard bone C2 confining the ear canal C. In other words: It is not required to introduce the distal tip 35 of the head portion 14 as far as a transition area C3 in which the ear canal C has a curvature C4 or a particularly small radius of curvature. Also, it is not required to introduce the distal tip 35 as far as the hard bone C2, i.e. the bony or osseous part of the ear canal C2. In particular, a distance of at least 10 mm can be kept between the distal tip 35 and the eardrum ED. This facilitates use of the otoscope 10 by laypersons. Furthermore, a mechanical manipulation of "straightening" the ear canal C is not required. In contrast to commonly used otoscopes, application of the inventive otoscope 10 does not necessarily require assistance by a medical practitioner.

As shown in FIG. 22, the diameter of the head portion 14 is defined such that the distal tip of the head portion 14 does not fit into the section of the ear canal C which is confined by hard bone C2. In particular, it has been found that in average (male and female persons), the external ear canal has a diameter of about 4.8 mm±0.5 mm. A summary referring to the average diameters of men can be found in: Salvinelli F, Maurizi M et al.; Scand. Audiol. 1991; 20(4): 253-6.

FIG. 23A shows an ear canal C which has an S-shaped (sigmoid) form with a first curvature C4' and a second curvature C4, the second curvature C4 being closer to the eardrum ED than the first curvature C4'. A head portion 14 of an otoscope 10 is introduced within the ear canal C. In the position shown in FIG. 23A, the second curvature C4 of the ear canal C obstructs any optical line of sight or visual communication of a distal end 18 of the head portion 14 with the eardrum ED.

FIG. 23B shows the ear canal C illustrated in FIG. 23A, wherein the otoscope 10 is introduced within the ear canal C as far as the second curvature C4, i.e. nearly as far as a transition area C3 between soft connective tissue C1 and hard bone C2. In the position shown in FIG. 23B, the otoscope 10 is able to "look around the corner". The "corner" can be defined as the second curvature C4 of the ear canal C.

Likewise as shown in FIG. 22, the diameter of the head portion 14 can be shaped such that it does not fit into the section of the ear canal C which is confined by hard bone C2. FIG. 23B only illustrates or refers to the relative axial position of the head portion 14, but not to any preferred diameter of the head portion 14. In particular, the outer diameter of the head portion 14, especially at the distal tip, preferably is bigger than the inner diameter of the section of the ear canal C which is confined by hard bone C2.

Figure 24B:
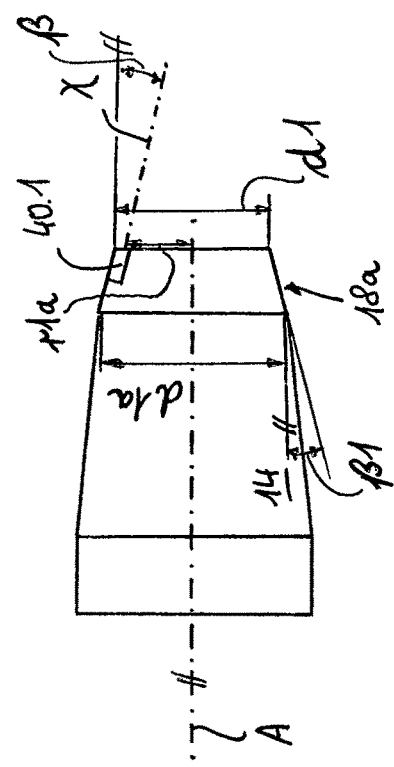
FIG. 24B schematically shows a head portion of an otoscope according to the present invention, the head portion exhibiting a conical distal end.
Figure 24A:
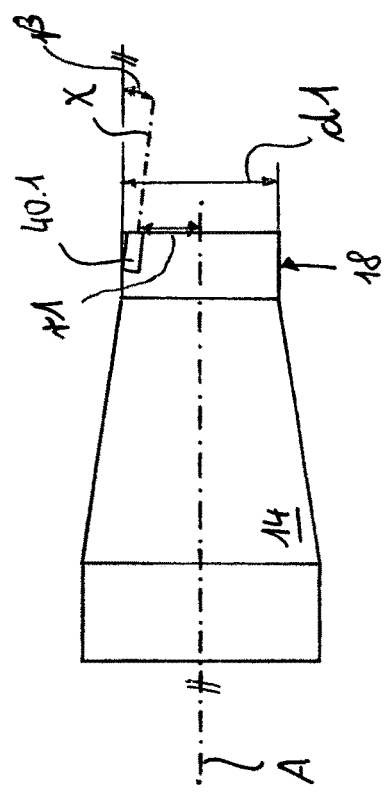
FIG. 24A schematically shows a head portion of an otoscope according to the present invention, the head portion exhibiting a cylindrical distal end.

FIG. 24A shows a head portion 14 exhibiting a distal end 18 or distal tip having a diameter d1. The diameter d1 is in the range of 4.7 mm to 5.2 mm, preferably 4.8 mm to 5 mm, especially 4.9 mm. The distal end 18 has a cylindrical shape. A camera 40.1 is arranged radially offset with a radial offset r1 with respect to a longitudinal axis A of the head portion 14. The camera 40.1 has an optical axis X. The camera 40.1 and its optical axis X are tilted against the longitudinal axis A. The tilt angle β is e.g. in the range of 10° to 30°. The optical axis X is tilted with respect to a lateral surface of the distal end 18. In such an arrangement, the maximum radial offset is restricted due to the tilted arrangement of the camera 40.1 with respect to the lateral surface of the distal end 18. Preferably, the tilt angle is variable.

FIG. 24B shows a head portion 14 exhibiting a distal end 18a or distal tip having a minimum diameter d1. The diameter d1 is in the range of 4.7 mm to 5.2 mm, preferably 4.8 mm to 5 mm, especially 4.9 mm. In contrast to the embodiment shown in FIG. 24A, the distal end 18a has a conical shape. The conical shape can be provided by a conical lateral surface, especially a conical inner lateral surface. In other words: The distal end 18a is not necessarily provided with a conical outer lateral surface having the same conicity as the conical inner lateral surface. A diameter d1a of a proximal border of the distal end 18a is slightly larger than the diameter d1. A camera 40.1 is arranged radially offset with a radial offset r1*a* with respect to a longitudinal axis A of the head portion 14.

The camera 40.1 has an optical axis X. The camera 40.1 and its optical axis X are tilted against the longitudinal axis A. The tilt angle β is e.g. in the range of 10° to 30°. In particular, the ratio d1*a*:d1 is larger than 1 for such an amount that a tilt angle β1 between the longitudinal axis A and a lateral surface of the distal end 18*a* at least approximately corresponds to the tilt angle β of the optical axis X.

As compared with the arrangement shown in FIG. 24A, the radial offset r1*a* can be larger than the radial offset r1, as the camera 40.1 can be arranged closer to the inner lateral surface of the distal end 18*a*. As a high radial offset is favorable for facilitating observation of the eardrum, and as the maximum diameter of the distal tip is limited for anatomical reasons, a conical distal end 18*a* provides an improved visibility. The distal end 18*a* can be provided in the form of a chamfer or bevel.

Figure 25A:
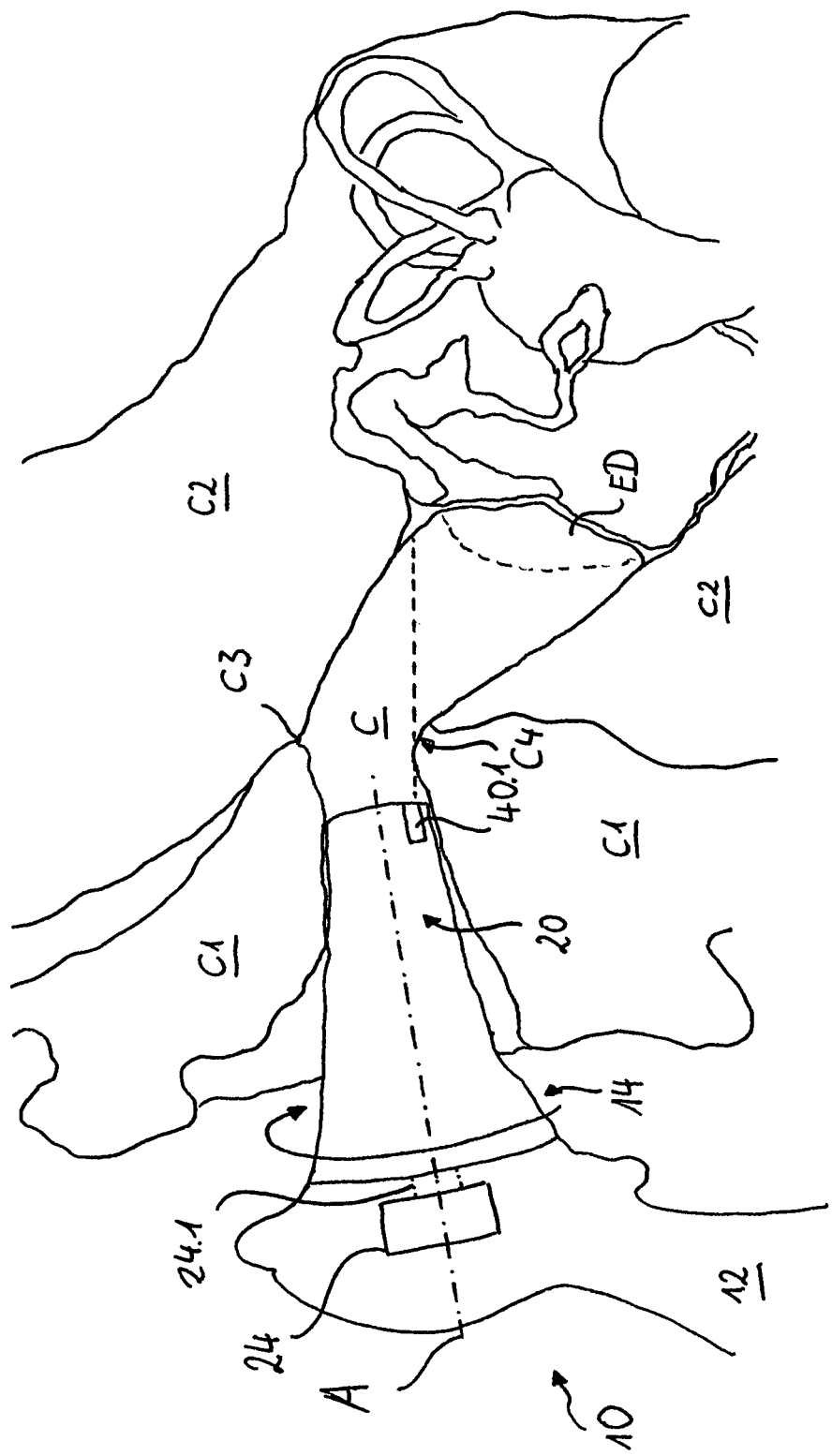
FIG. 25A shows an otoscope according to the present invention, with its head portion introduced into the patient's ear canal, and with a camera positioned in a first position.

FIG. 25A shows an otoscope 10 with a head portion 14 which can be rotated around a longitudinal axis A of the otoscope 10. An electronic imaging unit comprises a camera 40.1 which is positioned radially offset from the longitudinal axis A. The camera 40.1 is positioned at a distal tip of the head portion 14. In a position (first position) as shown in FIG. 25A, the camera 40.1 cannot scan the eardrum ED yet. The camera 40.1 is not in visual communication with the eardrum ED yet. Rather, a curvature C4 of the ear canal C obstructs any optical line of sight or visual communication, as illustrated by the dashed line. In the first position as shown in FIG. 25A, the eardrum ED cannot be seen at all by the camera 40.1. In order to ensure visual communication with the eardrum ED, firstly, the (radial) position of the camera 40.1 within the ear canal C has to be corrected. This can be done by rotating the head portion 14 or a part of the head portion 14 around the longitudinal axis A, especially without further motion, especially rotation, of a handle portion 12 of the otoscope 10. For this purpose, the otoscope 10 is provided with a motion mechanism 24. The motion mechanism 24 is arranged within the handle portion 12. The motion mechanism 24 includes a drive shaft 24.1 which connects the movable portion 20 with the handle portion 12. The movable portion 20 is supported by a bearing 28, as shown in detail in FIG. 26.

Figure 25B:
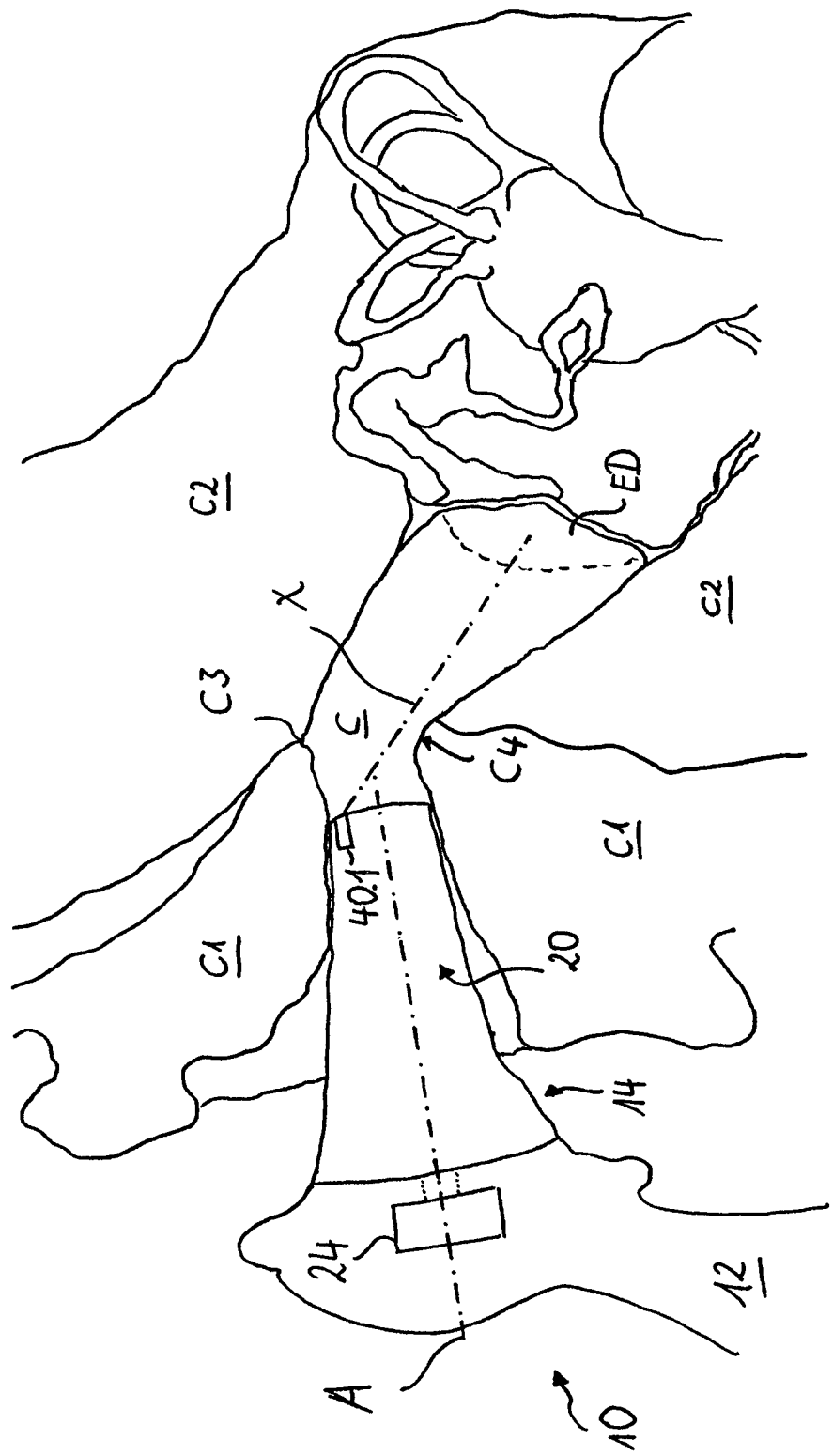
FIG. 25B shows the otoscope according to FIG. 25A, with the camera positioned in a second position.

FIG. 25B shows the camera 40.1 in a position in which an optical axis X of the camera 40.1 can be directed on the eardrum ED, although the distal tip of the head portion 14 is not introduced as far as a transition point C3 between the soft connective tissue C1 and the hard bone C2. The camera 40.1 had been rotated in the second position shown in FIG. 25B.

Rotation of the camera 40.1 can be carried out as described in the following. A movable portion 20 of the head portion 14 can be attached to a servo motor (not shown), e.g. a small standard servo motor (e.g. Modelcraft Micro-Servo MC1811 JR). The servo motor is arranged to turn the movable portion 20, especially by up to 180°. The servo motor has a height of e.g. about 2 cm and can be arranged directly on the axis of the rotating movable portion 20. The servo motor can exhibit a turning part that exceeds a motor housing by some millimeters. The servo motor can be attached to a chassis of the otoscope by means of a metal part which is designed to be firmly held aligned with the movable portion 20 hold by a bearing. One or more light guides (not shown) and a cable (not shown) can be connected to a printed circuit board (not shown). The cable can be directly soldered to the printed circuit board while the light guides can be directly mounted on light sources (not shown).

Figure 26:
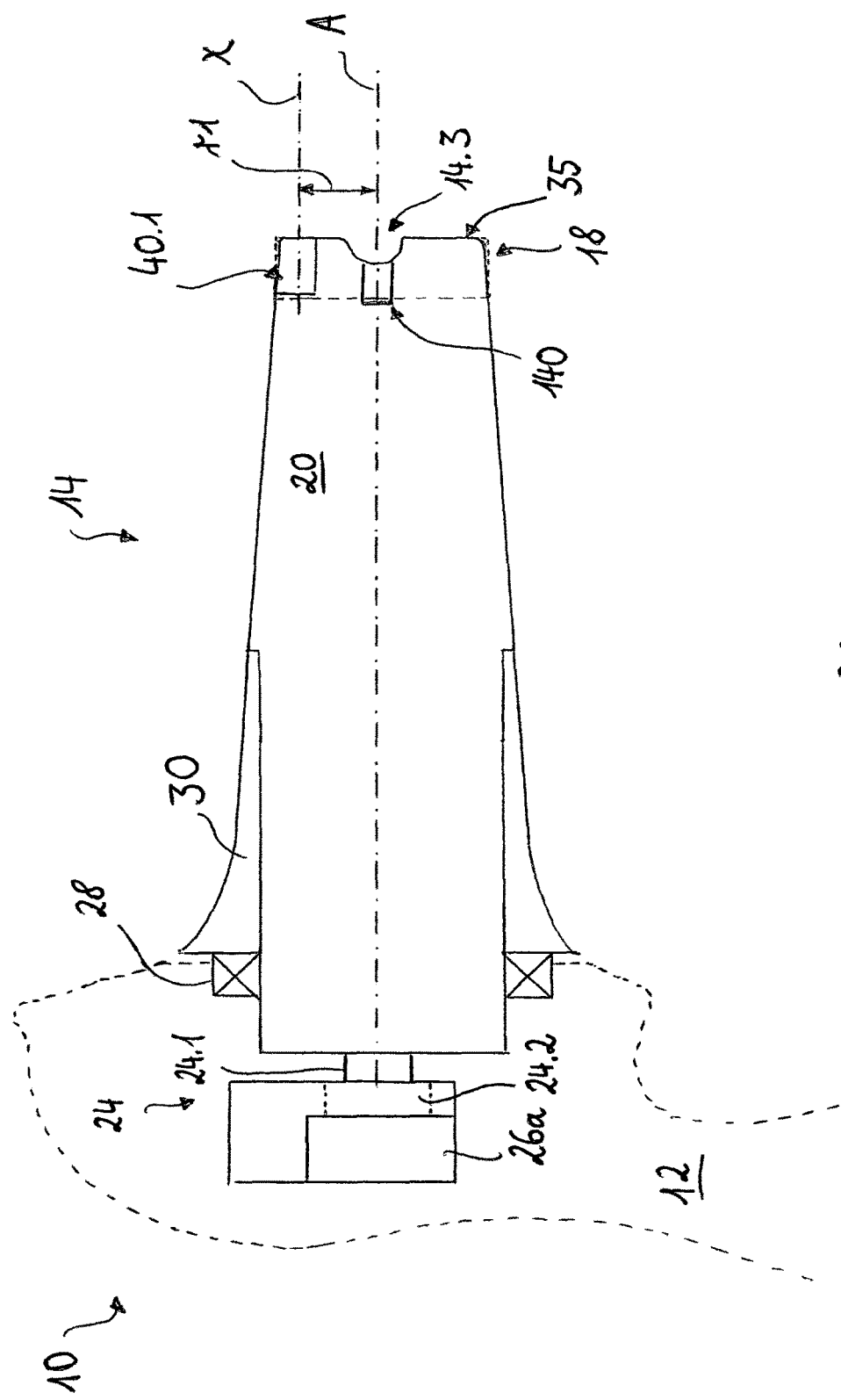
FIG. 26 schematically shows a cross-sectional view of a head portion and of a part of a handle portion of a further embodiment of an otoscope according to the present invention.

FIG. 26 shows an otoscope 10 with a handle portion 12 and a head portion 14. The head portion includes a movable portion 20 and a support structure 30. The movable portion 20 can be rotated by a motion mechanism 24 which is arranged in the handle portion 12. The movable portion 20 can be rotated with respect to the support structure 30. The motion mechanism 24 includes a drive shaft 24.1 which connects the movable portion 20 with the handle portion 12. The motion mechanism 24 includes a brushless motor 26*a* which is connected to the drive shaft 24.1. Optionally, a gear 24.2 is provided between the motor 26*a* and the drive shaft 24.1. The movable portion 20 is supported by the bearing 28 which is supported by the handle portion 12. The support structure 30 is supported by the handle portion 12. The support structure 30 provides a portion of the outer lateral surface of the head portion 14. In other words: The shape of the head portion 14 is partially defined by the support structure 30. In particular, the shape of a proximal portion of the head portion 14 is defined by the support structure 30. The support structure 30 is fixed at the handle portion 12 by means of the bearing 28.

The head portion 14 has a distal end 18 including a distal tip 35, wherein the distal end 18 has concial shape or a cylindrical shape (as indicated by the dashed line). An infrared sensor unit 140 is positioned centrically at the distal end 18. This position is only illustrated as an example. The infrared sensor unit 140 shown in FIG. 26 can be provided in conjunction with the other embodiments of the otoscopes as described in the preceding or following figures also. The distal end 18 is provided with an indentation 14.3 for accommodating a portion of a probe cover (not shown). A camera 40.1 having an optical axis X is arranged radially offset with respect to a longitudinal axis A of the head portion 14, wherein the radial offset r1 of the optical axis X preferably is in a range between 1.5 mm and 2 mm. The camera 40.1 is arranged adjacent to an inner lateral surface of the distal end 18. Preferably, the camera 40.1 is in contact with the inner lateral surface of the distal end 18.

In the FIGS. 25A, 25B and 26, a probe cover is not shown. According to the present invention, a probe cover either can be rotated together with the head portion or can be stationary. Preferably, the probe cover is not rotated, i.e. the probe cover is stationary.

Figure 27:
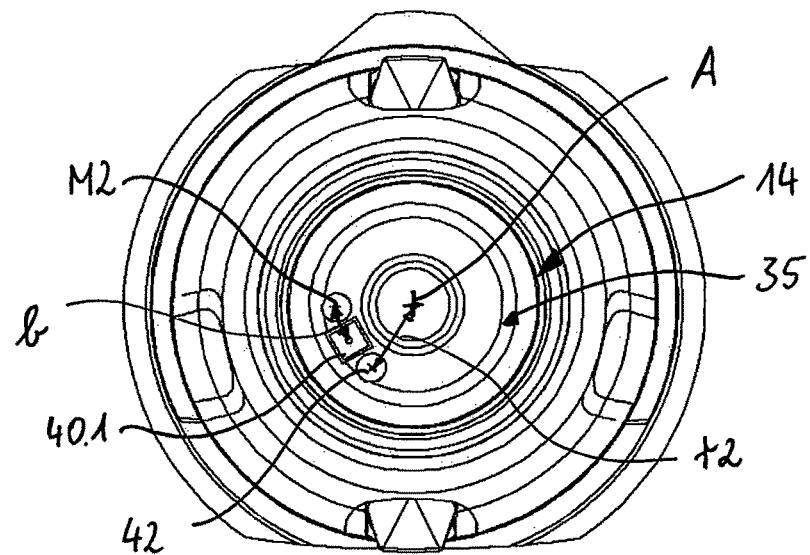
FIG. 27 schematically shows a front view of a head portion of an otoscope according to the present invention, wherein the radial position of light sources and a camera of the otoscope is illustrated.

FIG. 27 shows a head portion 14 accommodating an electronic imaging unit 40 which comprises one single camera 40.1. The camera 40.1 is positioned radially offset with a maximum radial offset at a distal tip 35 of the head portion 14. Two light guides or light sources 42 (e.g. LEDs) are arranged adjacent to the camera 40.1, especially on the same pitch circle as the camera 40.1. The light sources 42 are arranged with a radial offset r2 which corresponds to a radial distance between a longitudinal (middle) axis A of the head portion 14 and a middle axis M2 of the respective light source 42. In particular, the radial offset r2 of the light sources 42 can correspond to the radial offset of the camera 40.1 or, as an alternative, is even larger than the radial offset of the camera 40.1.

Preferably, the camera 40.1 can be rotated by a motion mechanism (not shown), especially together with the light guides 42 or at least the distal ends of the light guides 42. The diameter of the light guides 42 is in a range between 0.2 and 1.5 mm, preferably 0.7 mm and 1.2 mm, especially 1.0 mm. The (eccentric) radial distance or offset r2 is in the range of 1.8 mm to 2.5 mm, preferably 1.9 mm to 2.3 mm, further preferable 2.0 mm to 2.1 mm, depending on the diameter of the light guides 42. The two light guides 42 are arranged adjacent to the camera 40.1 in a distance b to the camera, wherein the distance b corresponds to the length of (a part of) a circular arc of the pitch circle on which the camera 40.1 and the two light guides 42 are arranged. The distance b is measured between a middle axis of the camera 40.1 and the middle axis M2 of the respective light guide 42. Preferably, the distance b is in the range of 0.5 mm to 2 mm, more preferable 0.8 mm to 1.8 mm, especially about 1.5 mm.

Figure 28:
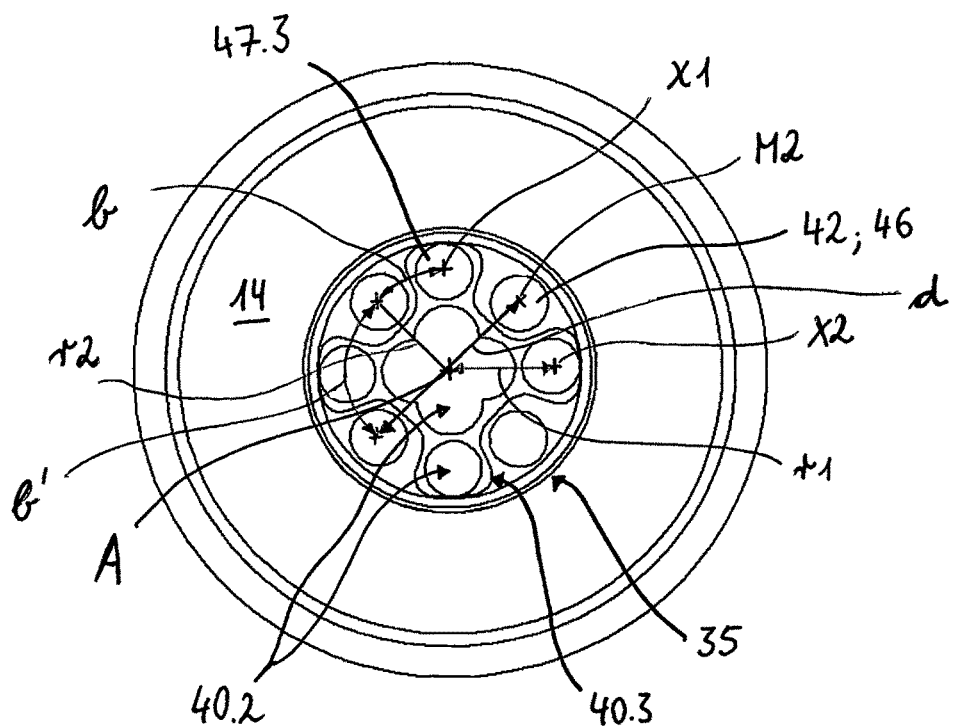
FIG. 28 schematically shows a front view of a head portion of an otoscope according to the present invention, wherein the radial position of light sources and a plurality of optical axes of the otoscope is illustrated.

FIG. 28 shows a head portion 14 with a distal tip 35. An electronic imaging unit 40 is positioned within the distal tip 35. The electronic imaging unit 40 comprises beam splitter optics 40.2 which exhibit a plurality of lenses or optical surfaces 47.3 (especially sixteen lenses or optical surfaces), from which eight lenses are shown in FIG. 28. The beam splitter optics 40.2 provide four different optical paths X1, X2. Each optical path is defined by four optical surfaces. Those or optical surfaces which define an optical path are arranged in the same plane, respectively. Four light guides or light sources 42 or LEDs 46 are arranged between the lenses 47.3, respectively. The light guides 42 or LEDs 46 are arranged adjacent to the lenses 47.3 having the largest radial offset, especially in a distance b to each lens 47.3. The distance b corresponds to the length of a circular arc of a pitch circle on which the lenses 47.3 and the light guides 42 are arranged. The distance b is measured between a middle axis of the respective to the lens 47.3 and a middle axis M2 of the respective light guide 42. Preferably, the distance b is smaller than 2 mm, e.g. 1.5 mm, more preferable smaller than 1.5 mm, e.g. 1.35 mm, further preferable smaller than 1.3 mm, especially between 1 mm and 1.3 mm, depending on the diameter of the light guides 42.

An outer lateral surface of a support 40.3 accommodating the lenses is arranged adjacent to an inner lateral surface of the distal tip 35. The outer lateral surface of the support 40.3 touches the inner lateral surface, in particular at four different sections. The light sources 42 or LEDs 46 are arranged within recesses or grooves 40.3a of the support 40.3.

The light sources 42 are arranged with a radial offset r2 which corresponds to a radial distance between a longitudinal (middle) axis A of the head portion 14 and a middle axis M2 of the respective light source 42. In particular, the radial offset r2 of the light sources 42 can correspond to the radial offset of the camera 40.1 or, as an alternative, is even larger than the radial offset of the camera 40.1. The (eccentric) radial distance or offset r2 is in the range of 1.8 mm to 2.5 mm, preferably 1.9 mm to 2.3 mm, further preferable 2.0 mm to 2.1 mm, depending on the diameter of the light guides 42.

Two of the light sources 42 or LEDs 46 are arranged in a distance b' to each other, respectively. The distance b' corresponds to the length of (a part of) a circular arc of the pitch circle on which the light sources 42 or LEDs 46 are arranged. Preferably, the distance b' is in a range between 5 mm and 3 mm, e.g. 4 mm, more preferable between 3.5 mm and 4.5 mm. With such an arrangement, light can be provided effectively, especially by two of the light guides 42 or LEDs 46 with respect to one of the lenses 47.3. In particular, by means of the arrangement of four light sources 42 in conjunction with four optical axes X1, X2 shown in FIG. 28, an ear canal can be observed substantially independent of the exact position of the respective lens 47.3 or light source 42 or LED 46 within the ear canal.

At least two of the light sources or light guides 42 or LEDs 46 are arranged in a maximum distance d apart from each other. The maximum distance d is measured between the middle axes M2 of the respective light guides 42. Preferably, the maximum distance d is at least 3.5 mm, more preferable at least 4 mm, further preferred in a range between 4.2 mm and 4.6 mm. This relatively large distance d facilitates stereoscopic viewing, especially by emitting light from two points which are most distant from each other, in order to analyse reflected light which is reflected from different directions. This relatively large distance d also facilitates evaluation of depth information, which can be helpful in order to distinguish the eardrum from any objects (e.g. ear wax) within the ear canal.

An LED 46 provides the advantage of short reaction time or high response speed. In other words: LEDs can be effectively used for stereoscopic viewing, as they can be switched on and off within a few milliseconds. LEDs can be actuated undelayed or instantaneously. LED illumination can thus be synchronized with a shutter of the electronic imaging unit, allowing for exposure of individual frames at different illumination conditions.

Figure 29:
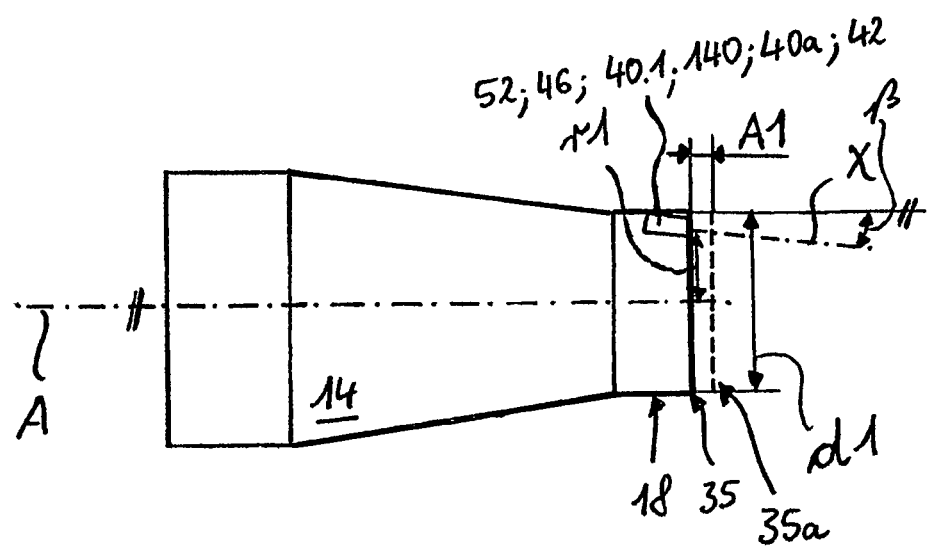
FIG. 29 schematically shows a head portion of an ear inspection device according to the present invention, the head portion exhibiting a cylindrical distal end.

FIG. 29 shows a head portion 14 exhibiting a distal end 18 or distal tip 35 having a diameter d1. The diameter d1 is in the range of 4.7 mm to 5.2 mm, preferably 4.8 mm to 5 mm, especially 4.9 mm. The distal end 18 has a cylindrical shape. At least one camera 40.1 and/or infrared sensor unit 52; 140 and/or light guide 42 or light source 46 and/or mobility sensor unit 40a is arranged radially offset with a radial offset r1 with respect to a longitudinal axis A of the head portion 14. The camera 40.1 or the respective device has an optical axis X. The camera 40.1 and its optical axis X are tilted against the longitudinal axis A. The tilt angle β is e.g. in the range of 10° to 30°. The optical axis X is tilted with respect to a lateral surface of the distal end 18.

The at least one camera 40.1 is arranged at a most distal position, i.e. contacting or providing the distal tip 35. Exemplary, an alternative configuration is shown, the distal tip being provided in a position with a distance A1 (protruding distal tip 35a). The distance A1 is a distance between the most distal front side or front surface of the head portion 14, i.e. the protruding distal tip 35a, and the most distal (optical) component of the camera 40.1 or the infrared sensor unit 52; 140 or the light source 46. Preferably, each device is positioned at a distance A1 of less than 3 mm, preferably less than 2 mm, more preferable less than 1 mm, from the protruding distal tip 35a. This may ensure that a radial offset can provide a most eccentric position of on observation point or illumination point or temperature detection point within the ear canal.

The invention claimed is:

1. An otoscope comprising:
   a handle portion allowing a user to manipulate the otoscope during its application; and
   a head portion exhibiting a substantially tapering form extending along a longitudinal axis of the head portion, wherein the head portion has a proximal end adjacent to the handle portion and a smaller distal end configured to be introduced in an ear canal of a patient's outer ear,
   wherein the otoscope further comprises an optical electronic imaging unit positioned at the distal end of the head portion, wherein the electronic imaging unit exhibits at least one optical axis which is positioned radially offset from the longitudinal axis, and wherein the distal end is configured for accommodating the electronic imaging unit in such a way that the radial offset can be maximum with respect to the diameter of the distal end, and wherein the radial offset is at least factor 0.25 of the radial dimension of the distal end.

2. The otoscope according to claim 1 wherein adjacent to an inner lateral surface of the distal end, the head portion exhibits a cavity for accommodating an optical component of the electronic imaging unit defining the at least one optical axis.

3. The otoscope according to claim 1 wherein the electronic imaging unit comprises a video camera defining an optical axis, preferably a wide angle color video camera, preferably with an angle of at least 80°.

4. The otoscope according to claim 1 wherein the electronic imaging unit comprises a support or housing defining the radial offset of at least one optical axis or accommodating at least one camera or beam splitter optics, wherein the support preferably is in contact with an inner lateral surface of the distal end.

5. The otoscope according to claim 1 wherein a distal tip of the head portion exhibits a diameter of at least 4.7 mm.

6. The otoscope according to claim 1 wherein the otoscope further comprises an infrared sensor unit positioned at the distal end of the head portion.

7. The otoscope according to claim 1 wherein the radial offset is at least factor 0.3 of the radial dimension of the distal end.

8. An otoscope comprising:
a handle portion allowing a user to manipulate the otoscope during its application; and
a head portion exhibiting a substantially tapering form extending along a longitudinal axis of the head portion wherein the head portion has a proximal end adjacent to the handle portion and a smaller distal end configured to be introduced in an ear canal of a patient's outer ear,
wherein the otoscope further comprises an optical electronic imaging unit positioned at the distal end of the head portion, wherein the electronic imaging unit exhibits at least one optical axis which is positioned radially offset from the longitudinal axis, and wherein the distal end is configured for accommodating the electronic imaging unit in such a way that the radial offset can be maximum with respect to the diameter of the distal end, wherein the electronic imaging unit comprises a miniature camera having dimensions of less than 3 mm×3 mm.

9. The otoscope according to claim 8 wherein the miniature camera is a wafer-level camera.

10. The otoscope according to claim 8 wherein the miniature camera has dimensions of less than 2 mm×2 mm.

11. An otoscope comprising:
a handle portion allowing a user to manipulate the otoscope during its application; and
a head portion exhibiting a substantially tapering form extending along a longitudinal axis of the head portion, wherein the head portion has a proximal end adjacent to the handle portion and a smaller distal end configured to be introduced in an ear canal of a patient's outer ear,
wherein the otoscope further comprises an optical electronic imaging unit positioned at the distal end of the head portion, wherein the electronic imaging unit exhibits at least one optical axis which is positioned radially offset from the longitudinal axis and wherein the distal end is configured for accommodating the electronic imaging unit in such a way that the radial offset can be maximum with respect to the diameter of the distal end, wherein the electronic imaging unit comprises at least one camera, the at least one camera having dimensions such that it can be arranged radially offset from the longitudinal axis of the head portion, wherein a radial offset with respect to an optical axis or a middle axis of the camera is in the range of 1 mm to 2.8 mm.

12. The otoscope according to claim 11 wherein the electronic imaging unit comprises three to six cameras.

13. The otoscope according to claim 11 wherein a radial offset with respect to an optical axis or a middle axis of the camera is at least 1.8 mm.

14. An otoscope comprising:
a handle portion allowing a user to manipulate the otoscope during its application; and
a head portion exhibiting a substantially tapering form extending along a longitudinal axis of the head portion, wherein the head portion has a proximal end adjacent to the handle portion and a smaller distal end configured to be introduced in an ear canal of a patient's outer ear,
wherein the otoscope further comprises an optical electronic imaging unit positioned at the distal end of the head portion, wherein the electronic imaging unit exhibits at least one optical axis which is positioned radially offset from the longitudinal axis, and wherein the distal end is configured for accommodating the electronic imaging unit in such a way that the radial offset can be maximum with respect to the diameter of the distal end, wherein the electronic imaging unit exhibits beam splitter optics defining at least two optical axes which are arranged radially offset from the longitudinal axis.

15. An otoscope comprising:
a handle portion allowing a user to manipulate the otoscope during its application; and
a head portion exhibiting a substantially tapering form extending along a longitudinal axis of the head portion, wherein the head portion has a proximal end adjacent to the handle portion and a smaller distal end configured to be introduced in an ear canal of a patient's outer ear,
wherein the otoscope further comprises an optical electronic imaging unit positioned at the distal end of the head portion, wherein the electronic imaging unit exhibits at least one optical axis which is positioned radially offset from the longitudinal axis and wherein the distal end is configured for accommodating the electronic imaging unit in such a way that the radial offset can be maximum with respect to the diameter of the distal end, and
further comprising a motion mechanism configured to allow displacement of the electronic imaging unit or the at least one optical axis or at least one camera of the electronic imaging unit relative to the handle portion.

16. The otoscope according to claim 15 wherein the motion mechanism is configured to allow for at least partial rotation of the electronic imaging unit or the at least one optical axis about an axis of rotation.

17. The otoscope according to claim 16 wherein the electronic imaging unit or the at least one optical axis is tilted against the axis of rotation so as to be continuously directed to a predetermined point on the axis of rotation, the predetermined point having a fixed distance to the electronic imaging unit.

18. The otoscope according to claim 16 wherein the motion mechanism is configured to allow for at least partial rotation of the electronic imaging unit or the at least one optical axis about the longitudinal axis of the head portion.

19. The otoscope according to claim 17, further comprising at least one light source also positioned at the distal end of the head portion.

20. The otoscope according to claim 17 wherein the electronic imaging unit or the at least one optical axis is tilted against the axis of rotation so as to be continuously directed to a predetermined point on the axis of rotation during a rotation by the motion mechanism.

21. The otoscope according to claim 19 wherein the at least one light source is positioned radially offset from the longitudinal axis of the head portion, wherein the radial offset is in the range of 1.8 mm to 2.5 mm.

22. The otoscope according to claim 21 wherein the radial offset is in the range of 1.9 mm to 2.3 mm.

23. The otoscope according to claim 19 wherein the otoscope exhibits at least two light sources or light guides which are arranged in a maximum distance apart from each other, wherein the maximum distance is at least 3.5 mm.

24. The otoscope according to claim 23, wherein the maximum distance is at least 4 mm.

25. The otoscope according to claim 19 wherein the at least one light source is arranged so as to maintain a predetermined distance with respect to the electronic imaging unit or at least one optical axis, even when the electronic imaging unit or the at least one optical axis is displaced by the motion mechanism.

26. The otoscope according to claim 19 wherein the at least one light source is coupled with the motion mechanism such that the motion mechanism allows for at least partial rotation of the at least one light source about an axis of rotation.

27. The otoscope according to claim 26 wherein the at least one light source is coupled with the motion mechanism directly or via the electronic imaging unit.

28. The otoscope according to claim 26 wherein the motion mechanism allows for at least partial rotation of the at least one light source about the longitudinal axis.

29. The otoscope according to claim 19, wherein the at least one light source is positioned at the distal tip of the head portion.

30. The otoscope according to claim 19, wherein the at least one light source comprises a plurality of light sources at the distal end of the head portion.

31. The otoscope according to claim 19, wherein the at least one light source comprises a plurality of light sources at the distal end of the head portion, each of the plurality of light sources being separately controllable.

32. An otoscope comprising:
a handle portion allowing a user to manipulate the otoscope during its application; and
a head portion exhibiting a substantially tapering form extending along a longitudinal axis of the head portion, wherein the head portion has a proximal end adjacent to the handle portion and a smaller distal end configured to be introduced in an ear canal of a patient's outer ear,
wherein the otoscope further comprises an optical electronic imaging unit positioned at the distal end of the head portion, wherein the electronic imaging unit exhibits at least two optical axes which are positioned radially offset from the longitudinal axis, wherein the distal end is configured for accommodating the electronic imaging unit in such a way that the radial offset can be maximum with respect to the diameter of the distal end, and wherein the electronic imaging unit exhibits beam splitter optics defining at least two of the optical axes, the at least two optical axes being arranged concentrically with respect to the longitudinal axis of the head portion.

33. The otoscope according to claim 32 wherein the electronic imaging unit exhibits three or four optical axes, which are positioned radially offset from the longitudinal axis.

34. The otoscope according to claim 32 wherein the electronic imaging unit exhibits beam splitter optics provided as single injection molded part, defining at least two of the optical axes.

35. The otoscope according to claim 32 wherein the at least two optical axes are arranged rotationally symmetrically with respect to the longitudinal axis of the head portion.

36. An otoscope comprising:
a handle portion allowing a user to manipulate the otoscope during its application; and
a head portion exhibiting a substantially tapering form extending along a longitudinal axis of the head portion, wherein the head portion has a proximal end adjacent to the handle portion and a smaller distal end configured to be introduced in an ear canal of a patient's outer ear,
wherein the otoscope further comprises an optical electronic imaging unit positioned at the distal end of the head portion, wherein the electronic imaging unit exhibits one optical axis which is positioned radially offset from the longitudinal axis, wherein the distal end is configured for accommodating the electronic imaging unit in such a way that the radial offset can be maximum with respect to the diameter of the distal end, wherein the electronic imaging unit comprises a miniature camera, the radial offset with respect to the optical axis or a middle axis of the camera being in the range of 1 mm to 2.8 mm and wherein the otoscope comprises a motion mechanism configured to allow displacement of the camera relative to the handle portion.

37. The otoscope according to claim 36 wherein the radial offset with respect to the optical axis or a middle axis of the camera is at least 1.8 mm.

38. The otoscope according to claim 36 wherein the otoscope comprises a motion mechanism configured to allow rotation of the camera relative to the handle portion.

39. An otoscope comprising:
a handle portion allowing a user to manipulate the otoscope during its application; and
a head portion exhibiting a substantially tapering form extending along a longitudinal axis of the head portion, wherein the head portion has a proximal end adjacent to the handle portion and a smaller distal end configured to be introduced in an ear canal of a patient's outer ear,
wherein the otoscope further comprises an optical electronic imaging unit positioned at the distal end of the head portion, wherein the electronic imaging unit exhibits at least two optical axes which are positioned radially offset from the longitudinal axis, wherein the distal end is configured for accommodating the electronic imaging unit in such a way that the radial offset can be maximum with respect to the diameter of the distal end, wherein the electronic imaging unit comprises at least two miniature cameras, the radial offset with respect to the optical axis or a middle axis of the cameras preferably respectively being in the range of 1 mm to 2.8 mm.

40. The otoscope according to claim 39 wherein the electronic imaging unit exhibits three or four optical axes which are positioned radially offset from the longitudinal axis.

41. The otoscope according to claim 39 wherein the electronic imaging unit comprises three or four miniature cameras.

42. An otoscope comprising:
a handle portion allowing a user to manipulate the otoscope during its application; and
a head portion exhibiting a substantially tapering form extending along a longitudinal axis of the head portion, wherein the head portion has a proximal end adjacent to the handle portion and a smaller distal end configured to be introduced in an ear canal of a patient's outer ear,
wherein the otoscope further comprises an optical electronic imaging unit positioned at the distal end of the head portion, wherein the electronic imaging unit exhibits four optical axes which are positioned radially offset from the longitudinal axis, wherein the distal end is configured for accommodating the electronic imaging unit in such a way that the radial offset can be maximum with respect to the diameter of the distal end, wherein the electronic imaging unit further comprises a number of four to eight light sources positioned radially offset from the longitudinal axis at the distal end, wherein at least one light source is correlated to a respective optical axis, and wherein the radial offset of the light sources is in the range of 1 mm to 2.5 mm.

43. The otoscope according to claim 42 wherein the electronic imaging unit comprises four light sources positioned radially offset from the longitudinal axis at the distal end.

44. The otoscope according to one of claim 1, 8, 11, 14, 15, 36, 39 or 42, wherein the optical electronic imaging unit is positioned at a distal tip of the head portion.

* * * * *